(12) United States Patent
Pettersson

(10) Patent No.: US 10,544,103 B2
(45) Date of Patent: Jan. 28, 2020

(54) 5-HT2 ANTAGONISTS

(71) Applicant: ANAMAR AB, Stockholm (SE)

(72) Inventor: Lars Pettersson, Lund (SE)

(73) Assignee: ANAMAR AB, Stockholm (SE)

( * ) Notice: Subject to any disclaimer, the term of this patent is extended or adjusted under 35 U.S.C. 154(b) by 0 days.

(21) Appl. No.: 15/737,125

(22) PCT Filed: Jun. 22, 2016

(86) PCT No.: PCT/EP2016/064446
§ 371 (c)(1),
(2) Date: Dec. 15, 2017

(87) PCT Pub. No.: WO2016/207231
PCT Pub. Date: Dec. 29, 2016

(65) Prior Publication Data
US 2018/0155292 A1 Jun. 7, 2018

(30) Foreign Application Priority Data

Jun. 22, 2015 (EP) .................................... 15173111

(51) Int. Cl.
| C07D 231/06 | (2006.01) |
| C07D 401/04 | (2006.01) |
| C07D 403/04 | (2006.01) |
| C07D 405/04 | (2006.01) |
| C07D 409/04 | (2006.01) |
| C07D 231/54 | (2006.01) |
| A61P 29/00 | (2006.01) |

(52) U.S. Cl.
CPC ............ C07D 231/06 (2013.01); A61P 29/00 (2018.01); C07D 231/54 (2013.01); C07D 401/04 (2013.01); C07D 403/04 (2013.01); C07D 405/04 (2013.01); C07D 409/04 (2013.01)

(58) Field of Classification Search
CPC .. C07D 231/06; C07D 401/04; C07D 403/04; C07D 405/04; C07D 409/04
See application file for complete search history.

(56) References Cited

U.S. PATENT DOCUMENTS

| 4,107,326 A | 8/1978 | Goldman et al. |
| 2009/0062363 A1 | 3/2009 | Kaku et al. |

FOREIGN PATENT DOCUMENTS

| DE | 102005014089 A1 | 9/2006 |
| GB | 1223491 | 2/1971 |
| WO | 0170700 A1 | 9/2001 |
| WO | 2005007157 A1 | 1/2005 |
| WO | 2006072351 A1 | 7/2006 |
| WO | 2007125049 A1 | 11/2007 |
| WO | 2008034863 A2 | 3/2008 |
| WO | 2011012868 A1 | 2/2011 |
| WO | 2013006308 A2 | 1/2013 |

OTHER PUBLICATIONS

Chemical Abstracts Registry No. 641992-12-3, indexed in the Registry file on STN CAS Online on Jan. 27, 2004. (Year: 2004).*
Abd-El Gawad et al., Archives of Pharmacal Research, 2012, 35(5), pp. 807-821 (Year: 2012).*
Berger, M., et al., "The Expanded Biology of Serotonin", Annu. Review Med. 60:355-366 (2009).
Brea, J., et al., "Emerging opportunities and concerns for drug discovery at serotonin 5-5-HT2B receptors", vol. 10: 493-503, Current Topics in Medicinal Chemistry (2010).
Bernatowicz, M.S., et al., "Urethane protected derivatives of 1-Guanylpyrazole for the mild and efficient preparation of guanidines", Tetrahedron Letters, vol. 34(21):3389-3392 (1993).
Cervantes-Duran, C. et al., "Evidence for the participation of peripheral 5-HT2A, 5-HT2B, and 5-HT2C receptors in formalin-induced secondary mechanical allodynia and hyperalgesia", Neuroscience, pp. 1-13 (2012).
Du, X., et al., Synthesis and structure-activity relationship study of potent trypanocidal thio semicarbazone inhibitors of the trypanosomal cysteine protease cruzain, Journal of Medicinal Chemistry, vol. 45:2695-2707 (May 18, 2002).
Ferreras, J.A., et al., "Chemical scaffolds with structural similarities to siderophores of nonribosomal peptide-polyketide origin as novel antimicrobials against *Mycobacterium tuberculosis* and *Yersinia pestis*", Bioorganic & Medicinal Chemistry Letters, vol. 21(21):6533-6537 (Aug. 26, 2011).
Jaffre, F., et al., "Involvement of the serotonin 5-HT2B receptor in cardiac hypertrophy linked to sympathetic stimulation", Circulation, vol. 110(8):969-74 (2004).
Scott, "Nitrogen Systems. Part XIV: The synthesis of 1-guanyl-pyrazolines", Chimia, pp. 148-150 (1956).
Jagrat, M., et al., "Pyrazoline based MAO inhibitors: synthesis, biological evaluation and SAR studies", Bioorganic & Medicinal Chemistry Letters, vol. 21(14):4296-4300 (May 25, 2011).
Poissonnet, J.G., et al., "The emergence of selective 5-HT2B antagonists structures, activities and potential therapeutic applications", Mini-Reviews in Medicinal Chemistry, vol. 4(3):325-330 (2004).
Scott, F.L., et al., "Acylhydrazide transformations", Chemistry & Industry (London, U.K.), pp. 907-908 (Sep. 13, 1952).

(Continued)

Primary Examiner — Laura L Stockton
(74) Attorney, Agent, or Firm — RatnerPrestia

(57) ABSTRACT

Provided are 1-amidino-3-aryl-2-pyrazoline derivatives which exhibit antagonizing activity towards serotonin 5-HT 2B receptors and pharmaceutical compositions containing these derivatives. Also provided is the use of the compounds as a medicament and for the treatment of fibrosis, cardiovascular diseases, pain, IBD, and other inflammatory diseases.

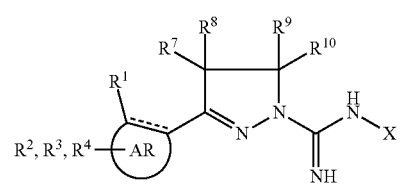

14 Claims, 1 Drawing Sheet

(56) References Cited

OTHER PUBLICATIONS

Thomas M., et al., "Targeting the serotonin pathway for the treatment of pulmonary arterial hypertension", Pharmacology & Therapeutics, vol. 138(3):409-417 (2013).
International Search Report and Written Opinion for International Application No. PCT/EP2016/064446, dated Aug. 5, 2016—9 Pages.
Dees et al., "Platelet-derived Serotonin Links Vascular Disease and Tissue Fibrosis", J. Exp. Med., vol. 208, No. 5, pp. 961-972, May 2011.
Ebrahimkhani et al., "Stimulating Healthy Tissue Regeneration by Targeting the 5-HT2B Receptor in Chronic Liver Disease" Nat. Med.; vol. 17, No. 12, pp. 1668-1673, Nov. 2011.
Fabre et al., "Modulation of Bleomycin-induced Lung Fibrosis by Serotonin Receptor Antagonists in Mice", Eur. Respir. J. 2008, vol. 32, pp. 426-436.
Konigshoff et al., "Increased Expression of 5-Hydroxytryptamine2A/B Receptors in Idiopathic Pulmonary Fibrosis: A Rationale for Therapeutic Intervention", Thorax, 2010, vol. 65, pp. 949-955.
Mann et al., "Serotonin Paracrine Signaling in Tissue Fibrosis", Biochima et Biophysica Acta 1832 (2013) pp. 905-910.
Nebigil et al., "Overexpression of the Serotonin 5-HT2B Receptor in Heart Leads to Abnormal Mitochondrial Function and Cardiac Hypertrophy", Circulation, 2003:vol. 107, pp. 3223-3229.

\* cited by examiner

5-HT2 ANTAGONISTS

CROSS-REFERENCE TO RELATED APPLICATIONS

This is the national phase of International Application No. PCT/EP2016/064446, filed 22 Jun. 2016, which claims priority to European Application No. 15173111.4, filed 22 Jun. 2015.

FIELD OF THE INVENTION

The present invention relates to novel 5-HT$_2$ antagonists. The invention specifically relates to such derivatives which exhibit antagonizing activity towards serotonin 5-HT$_{2B}$ receptors. The present invention also relates to use of said compounds as a medicament and for the treatment of fibrosis, cardiovascular diseases, pain, IBD, and other inflammatory diseases, as well as pharmaceutical compositions comprising one or more of said compounds and methods of treatment.

BACKGROUND OF THE INVENTION

Serotonin (5-Hydroxytryptamine, 5-HT) is a well characterized neurotransmitter and vasoactive amine which has been implicated in common disorders involving central nervous, gastrointestinal, cardiovascular and pulmonary systems (for review see Berger, M. et al., Annu Rev Med. (2009), 60, 355-366). Peripheral 5-HT is mainly synthesized and released by the enterochromaffin cells in the gut. When reaching the blood stream it is sequestered inside platelets. Under normal conditions the level of free 5-HT in plasma is low and strictly regulated by specific 5-HT transporters present on the surface of e.g. platelets as well as by 5-HT degrading enzymes. Upon activation platelets release 5-HT and a local increase in 5-HT concentration is observed. Over the years evidence has gathered that 5-HT has a significant role in the functioning of the mammalian body. For example it has been shown to regulate processes like cardiovascular function, bowel motility and bladder control. 5-HT and the 5-HT receptor system have also been associated with the modulation of pain and more specifically, the 5-HT$_2$ receptors have been shown to play an important role in the inflammatory pain process (Cervantes-Duran C. et al., Neuroscience (2012) 232, 169). Furthermore, several studies have shown that the 5-HT system has an important role in the regulation of inflammation. The exact function of 5-HT on inflammation is poorly recognized though, with only a few and inconsistent published reports.

A greater understanding of 5-HT function has emerged with the characterization of its, at least, 14 different human receptors which are grouped into subfamilies based on their structural and pharmacological differences. Each receptor exhibit unique distribution and shows various preference for different ligands. The receptors are all G protein-coupled receptors, with the exception of the 5-HT$_3$ receptor, which is a ligand-gated ion channel. Several of the 5-HT receptors have been linked to 5-HT's effects in inflammation.

The 5-HT$_2$ receptor family consists of 3 subtypes, 5-HT$_{2A}$, 5-HT$_{2B}$ and 5-HT$_{2C}$. The 5-HT$_2$ receptors share significant sequence homology at the amino acid level and couple to the Gq family of the G proteins. An important role of 5-HT$_2$ receptors in inflammation has been shown in the kaolin/carrageenan-induced rat arthritis model in which the 5-HT$_{2A}$ receptor antagonist ketanserin suppressed oedema formation and hyperalgesia. Also, mianserin, a 5-HT$_{2A/2C}$ receptor antagonist, has been shown to inhibit cytokine production in human RA synovial membrane cultures.

The link between the 5-HT$_{2B}$ receptor and inflammation is less investigated, however, the involvement of 5-HT$_{2B}$ receptor signalling in 5-HT-induced production of IL-1β, IL-6 and TNF-α in mouse cardiac fibroblasts has been shown (Jaffre F. et al., Circulation (2004) 110(8), 969-74). The mRNA expression of the 5-HT$_{2B}$ receptor on inflammatory cells such as macrophages and fibroblasts makes it important to investigate 5-HT$_{2B}$ as target for modulating an inflammatory response in diseases such as rheumatoid arthritis. The use of N-benzylidene aminoguanidines as 5-HT$_{2B}$ receptor antagonist for this purpose has been described in WO2011012868A1.

The 5-HT$_{2B}$ receptor has previously been linked to pulmonary arterial hypertension (PAH) (Thomas M. et al., Pharmacol Ther. (2013) 138(3), 409-17) and the phenotype of the 5-HT$_{2B}$ receptor knock-out mice shows its importance for heart development. It demonstrates that 5-HT via the 5-HT$_{2B}$ receptor regulates differentiation and proliferation of developing and adult heart. Furthermore, over-expression of the 5-HT$_{2B}$ receptor in mice leads to cardiac hypertrophy (Nebigil C. G. et al., Circulation. (2003) 107(25), 3223-9).

In agreement with this, 5-HT and its receptors, 5-HT$_{2A}$ and 5-HT$_{2B}$ in particular, have been implicated in the etiology of several fibrotic disorders including retroperitoneal fibrosis, carcinoid heart disease, systemic sclerosis, liver and lung fibrosis. Fibrosis is actually a feature of many different types of chronic respiratory diseases including IPF, PAH, COPD and asthma. A mechanistic link between fibrosis and 5-HT was first reported in the 1960s for a condition called carcinoid syndrome which is caused by neuroendocrine carcinoid tumours that secrete vast quantities of 5-HT. The syndrome is characterized by tissue fibrosis that particularly affects cardiac valves but also impacts on other organs including lung and skin. Subsequently, agonism on the 5-HT$_{2B}$ receptor has been implicated in fibrosis caused by fenfluramine used in the treatment of obesity and psychiatric disorders. Fibrosis is characterized by enhanced fibroblast/myofibroblast proliferation and activation which results in an altered extracellular matrix deposition which ultimately results in organ failure (Mann, D. A. and Oakley F., Biochim Biophys Acta. (2013) 1832(7), 905-10).

An important mediator of the fibrotic process is transforming growth factor beta, TGF-β. This cytokine modulates a variety of physiological processes through transcriptional regulation. In human lung fibroblasts, TGF-β is well-known for inducing myofibroblast differentiation with increased levels of alpha-SMA in intracellular stress fibers as well as an increased matrix deposition. A lot of evidence support a role of 5-HT in fibrosis although the exact mechanism how 5-HT promotes fibrosis is not defined. 5-HT has been shown to increase the mRNA levels of TGF-β via the 5-HT$_{2B}$ receptor and in models of systemic sclerosis human dermal fibroblasts have a dose-dependent increase of TGF-β mRNA in response to 5-HT as well as an increased expression of the 5-HT$_{2B}$ receptor. This results in an increased mRNA expression of collagen 1a1, collagen 1a2 and fibronectin. The effects of 5-HT on matrix synthesis were blocked by a 5-HT$_{2B}$ receptor antagonist or by transfected 5-HT$_{2B}$ siRNAs. The same study showed that selective 5-HT$_{2B}$ receptor antagonists prevent bleomycin-induced dermal fibrosis in vivo (Dees C., et al., J. Exp. Med. (2011) 208(5), 961-72). In other fibrotic diseases such as liver fibrosis, treatment with 5-HT$_{2B}$ receptor antagonists resulted in attenuated fibrogenesis in an in vivo model of chronic liver disease (Ebrahimkhani, M. R., et al., Nat Med. (2011)

17(12), 1668-73). Further support for 5-HT and fibrosis is found in patients suffering from IPF that have an increased expression of 5-HT$_{2A}$ and 5-HT$_{2B}$ receptors in the fibrotic lung. Another study identified strong fibroblast expression of 5-HT$_{2B}$ receptor in fibroblastic foci in human lung samples from IPF patients. In addition, treatment with Terguride, a 5-HT$_{2A}$ and 5-HT$_{2B}$ receptor antagonist, reduces the expression of type I collagen in TGF-β1 stimulated human lung fibroblasts. This anti-fibrotic effect is also seen after treatment with 5-HT$_{2A}$ and 5-HT$_{2B}$ receptor antagonists in the bleomycin (BLM)-induced lung fibrosis model in mice (Konigshoff M., et al. Thorax. (2010); 65(11), 949-55 and Fabre A., et al. Eur Respir J. (2008) 32(2), 426-36).

5-HT$_{2B}$ Antagonists

Many 5-HT$_{2B}$ antagonists of variable structural classes have been described in the literature, such as in WO2011012868A1. Two recent reviews on the subject enlist such compounds, their intended uses, and their state of development (Poissonnet, G., et al., Mini-Reviews in Medicinal Chemistry (2004), 4(3), 325-330 and Brea, J. et al., Current Topics in Medicinal Chemistry (Sharjah, United Arab Emirates) (2010), 10(5), 493-503). These include the di-ureas SB206553 and SB215505, the piperazine derivative EGIS-7625, the 2-amino-4-naphthyl-pyrimidine MT-500 (RS127445), thioxanthene structures, the ergot derivative terguride, tetrahydro-β-carbolines, the thienopyrimidine PRX-08066, and quinoline derivatives. More recent examples of 5-HT$_{2B}$ antagonists that also contain a guanidine moiety, are disclosed in US2009062363A1.

Structurally related 5-HT$_{2B}$ antagonists are N-benzylidene amminoguanidines, such as N-(2-chloro-3,4-dimethoxybenzylidene-amino)guanidine (WO2011012868A1).

1-Amidino-3-Aryl-2-Pyrazolines

The compound class 1-amidino-3-aryl-2-pyrazolines was first reported in the 1950s describing synthetic preparative methods in which aryl Mannich bases were condensed with aminoguanidine (Scheme 1),

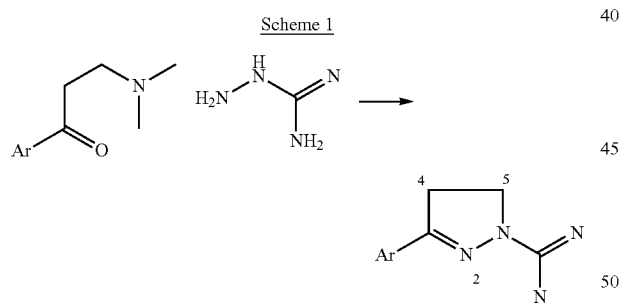

see: Scott, F. L. and Reilly, J., Chemistry & Industry (London, United Kingdom) (1952), 907-8 and Nitrogen systems. XIV. Scott, F. L. and Scott, M. T., Chimia (1958), 12, 148-50. Some derivatives, typically substituted at the 4- or 5-position in the pyrazoline ring and/or at the amidine group, have later been developed into pharmacologically active compounds. These include 4-aryl-N-sulfonamides as CB1-antagonists and potassium channel modulators (WO2001070700 A1 and WO2007125049A1), 4-heterocyclyl derivatives as PAR-1 antagonists (WO2005007157A1), N-sulfonamides as 5-HT$_6$ antagonists (WO2008034863A2), and 5-aryl derivatives as necroptosis inhibitors (Jagtap, P. G., et al., J. Med. Chem. (2007), 50(8), 1886-1895), as MAO-inhibitors (Sahoo, A. et al., Bioorganic & Medicinal Chemistry Letters (2010), 20(1), 132-136 and Jagrat, M. et al., Bioorganic & Medicinal Chemistry Letters (2011), 21(14), 4296-4300), and as antimicrobials (Ferreras, J. A. et al., Bioorganic & Medicinal Chemistry Letters (2011), 21(21), 6533-6537).

Also, the para-substituted 1-amidino-3-aryl-4-methyl-2-pyrazolines below have been reported as anti-inflammatory and analgesic agents, however, with no mode of action described. (Abd-El G., et al. Arch Pharm Res (2012), 35(5), 807-821).

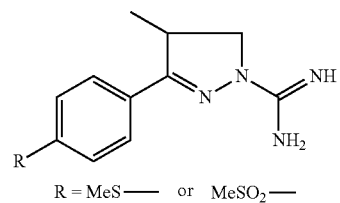

R = MeS— or MeSO$_2$—

SUMMARY OF THE INVENTION

It has been identified that 1-amidino-3-aryl-2-pyrazolines are 5-HT$_{2B}$ receptor antagonists with high potency and/or selectivity. In particular, it has been identified that certain substitution patterns enhance 5-HT$_{2B}$ receptor binding. Specifically, substituents in the ortho-position of the aromatic moiety may confer an enhanced 5-HT$_{2B}$ receptor binding affinity and thus an enhanced antagonistic potency. Furthermore, the compounds of the present invention, due to the presence of the pyrazoline ring, cannot undergo light induced cis/trans-isomerization of the benzyl imine double-bond, a characteristic of the above mentioned N-benzylidene-aminoguanidine compounds.

One objective problem of the present invention is to develop new 1-amidino-3-aryl-pyrazolines as antagonists of the serotonin 5-HT$_{2B}$ receptors for the treatment of diseases, such as fibrosis, cardiovascular diseases, pain, IBD, and other inflammatory diseases.

DETAILED DESCRIPTION OF THE INVENTION

The present invention relates to a compound of the general formula I

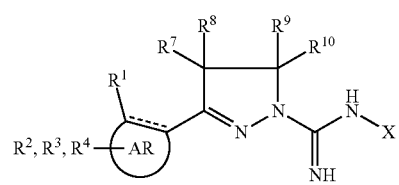

DEFINITIONS

Figure 1:
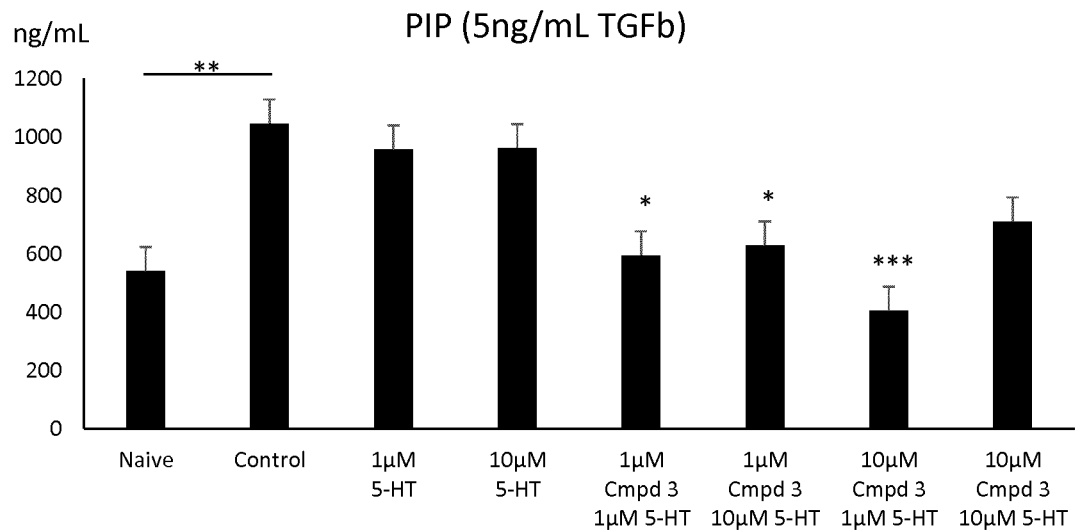
FIG. 1 provides a histogram with data showing effects by a compound of the invention on collagen production in normal human lung fibroblasts, suggesting an anti-fibrotic role.

The phrase "5-10 membered mono- or bicyclic aromatic or heteroaromatic ring system containing 0-4 heteroatoms independently selected from N, O, and S" represents, but is not limited to, pyrrolyl, pyrazolyl, imidazolyl, triazolyl, tetrazolyl, furanyl, thiophenyl, isoxazolyl, oxazolyl, oxadiazolyl, dioxazolyl, thiazolyl, phenyl, pyridyl, pyridazinyl, pyrimidinyl, pyrazinyl, triazinyl, naphthyl, indolyl, isoindolyl, indazolyl, benzimidazolyl, benzotriazolyl, purinyl, quinolinyl, isoquinolinyl, quinazolinyl, quinoxalinyl, naphthyridine, phthalazinyl, pteridinyl, benzofuranyl, iso benzofuranyl, benzothiophenyl, isobenzothiophenyl, benzoxazolyl, benzisoxazolyl, furopyridinyl, oxazolopyridinyl, benzothiazolyl, benzisothiazolyl, thienopyridine, ethylenedioxyphenyl or methylenedioxyphenyl. It is understood that only one of the rings is aromatic when the ring system is methylenedioxyphenyl or ethylenedioxyphenyl.

The term "alkyl" represents a linear or branched alkyl group having the number of carbon atoms specifically indicated, e.g. $C_1$-$C_{10}$ one, two, three, four, five, six, seven, eight, nine or ten carbon atoms, including, but not limited to methyl, ethyl, n-propyl, isopropyl, n-butyl, isobutyl, sec-butyl, tert-butyl, pentyl, isopentyl, hexyl, heptyl, octyl, nonyl-, decyl-, 2-methylbutyl, 1-methylbutyl, 1-ethylpropyl, 1,2-dimethylpropyl, neo-pentyl, 1,1-dimethylpropyl, 4-methylpentyl, 3-pethylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl.

The term "$C_1$-$C_{15}$ alkyl" represents any saturated, linear or branched alkyl group containing 1-15 carbons, including, but not limited to methyl, ethyl, n-propyl, iso-propyl, n-butyl, iso-butyl, neo-butyl, tert-butyl, pentyl, hexyl, heptyl, octyl, nonyl, decyl, undecyl, dodecyl, tridecyl, tetradecyl, or pentadecyl and isomers thereof.

The term "$C_1$-$C_{16}$ alkyl" represents any saturated, linear or branched alkyl group containing 1-16 carbons, including, but not limited to methyl, ethyl, n-propyl, iso-propyl, n-butyl, iso-butyl, neo-butyl, tert-butyl, pentyl, hexyl, heptyl, octyl, nonyl, decyl, undecyl, dodecyl, tridecyl, tetradecyl, pentadecyl, or hexadecyl and isomers thereof.

The term "$C_1$-$C_{12}$ alkyl" represents any saturated, linear or branched alkyl group containing 1-12 carbons, including, but not limited to methyl, ethyl, n-propyl, iso-propyl, n-butyl, iso-butyl, neo-butyl, tert-butyl, pentyl, hexyl, heptyl, octyl, nonyl, decyl, undecyl, or dodecyl and isomers thereof.

The term "$C_1$-$C_6$ alkyl" represents any saturated, linear or branched alkyl group containing 1-6 carbons, including, but not limited to methyl, ethyl, n-propyl, iso-propyl, n-butyl, iso-butyl, neo-butyl, tert-butyl, pentyl and hexyl and isomers thereof.

The term "$C_3$-$C_5$ cycloalkyl" represents cyclopropyl, cyclobutyl or cyclopentyl.

The term "$C_3$-$C_6$ cycloalkyl" represents cyclopropyl, cyclobutyl, cyclopentyl, and cyclohexyl.

The term "$C_1$-$C_3$ haloalkyl" represents methyl substituted with 1-3 halogen atoms, ethyl substituted with 1-5 halogen atoms, or n-propyl or isopropyl substituted with 1-7 halogen atoms.

The term "fluoroalkyl" represents an alkyl group as defined supra, substituted with one or more fluorine atoms.

The term "$C_1$-$C_4$ fluoroalkyl" represents fluoroalkyl group as defined supra, with 1 to 4 carbon atoms. Examples of $C_1$-$C_4$ fluoroalkyl groups include ethyl substituted with 1-5 fluorine atoms, n-propyl or isopropyl substituted with 1-7 fluorine atoms, and butyl substituted with 1 to 9 fluorine atoms, and isomers thereof.

The term "fluoromethyl" represents a methyl group with 1 to all hydrogen atoms substituted with fluorine atoms. Examples of fluoromethyl include monofluoromethyl, difluoromethyl and trifluoromethyl.

The term "$C_1$-$C_{16}$ acyl" represents an alkyl as defined supra in which the carbon bound to the rest of the compound is a carbonyl carbon i.e. instead of two of the hydrogen atoms, the carbon has a double bound oxygen. Examples of $C_1$-$C_{16}$ acyl groups include —C(O)CH$_3$, —CO(CH$_2$)$_n$CH$_3$, wherein n are integers from 1 to 14.

In one aspect of the invention, there is provided a compound of the general formula I

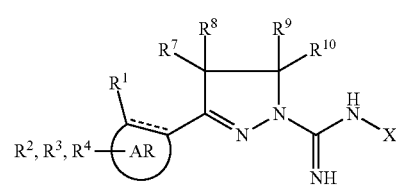

I wherein

AR represents a 5-10 membered mono- or bicyclic aromatic or heteroaromatic ring system containing 0-4 heteroatoms independently selected from N, O, and S;

$R^1$ is selected from $C_1$-$C_6$ alkyl, $C_3$-$C_5$ cycloalkyl, $C_1$-$C_3$ haloalkyl, OR$^5$, OC(O)R$^5$, OC(O)OR$^5$, OC(O)NR$^5$R$^6$, SR$^5$, S(O)R$^5$, S(O)$_2$R$^5$, S(O)$_2$OR$^5$, S(O)$_2$NR$^5$R$^6$, NR$^5$R$^6$, NR$^5$C(O)R$^6$, NR$^5$C(O)NR$^6$R$^6$, C(O)R$^5$, C(O)OR$^5$, C(O)NR$^5$R$^6$, NR$^5$C(O)OR$^6$, F, Cl, Br, I, CN, phenyl, 4-fluorophenyl, 4-chlorophenyl, and 4-methoxyphenyl; or R$^1$ is part of said ring system when said ring system is bicyclic;

$R^2$, $R^3$, and $R^4$ are independently selected from R$^5$, OR$^5$, OC(O)R$^5$, OC(O)OR$^5$, OC(O)NR$^5$R$^6$, SR$^5$, S(O)R$^5$, S(O)$_2$R$^5$, S(O)$_2$OR$^5$, S(O)$_2$NR$^5$R$^6$, NR$^5$R', NR$^5$C(O)R', NR$^5$C(O)NR$^6$R$^6$, C(O)R$^5$, C(O)OR$^5$, C(O)NR$^5$R$^6$, NR$^5$C(O)OR$^6$, F, Cl, Br, I, CN, 4-fluorophenyl, 4-chlorophenyl, and 4-methoxyphenyl, wherein R$^2$, R$^3$, and R$^4$ are positioned independently in any of the free positions of the mono- or bicyclic aromatic or heteroaromatic ring system;

$R^5$ and $R^6$ are independently selected from hydrogen, $C_1$-$C_{16}$ alkyl, $C_3$-$C_5$ cycloalkyl, phenyl, benzyl, and $C_1$-$C_3$ haloalkyl;

$R^7$, $R^8$, $R^9$, and $R^{10}$ are independently selected from hydrogen, methyl, ethyl, n-propyl, iso-propyl, and n-butyl; or being selected such that R$^8$ and R$^9$ are connected to form a 4-, 5-, 6-, or 7-membered ring;

X is selected from hydrogen, $C_1$-$C_{16}$ alkyl, $C_3$-$C_6$ cycloalkyl, $C_1$-$C_{16}$ acyl CN, $C_1$-$C_4$ fluoroalkyl, phenyl, benzyl, hydroxy, methoxy, ethoxy, C(O)OCH$_2$CH$_3$, 2-phenylethyl and benzyloxy, wherein said phenyl, 2-phenylethyl and benzyl groups are optionally mono-, di- or tri-substituted by substituents independently selected from $C_1$-$C_6$ alkyl, $C_1$-$C_6$ alkoxy, $C_1$-$C_6$ fluoroalkyl, F, Cl, Br, and I; and pharmaceutically acceptable salts, prodrugs, tautomers, and stereoisomers thereof.

In one embodiment of this aspect, there is provided a compound of Formula I, wherein AR represents a 5-10 membered mono- or bicyclic aromatic or heteroaromatic ring system containing 0-4 heteroatoms independently selected from N, O, and S;

$R^1$ is selected from $C_1$-$C_6$ alkyl, $C_3$-$C_5$ cycloalkyl, $C_1$-$C_3$ haloalkyl, $OR^5$, $OC(O)R^5$, $OC(O)OR^5$, $OC(O)NR^5R^6$, $SR^5$, $S(O)R^5$, $S(O)_2R^5$, $S(O)_2OR^5$, $S(O)_2NR^5R^6$, $NR^5R^6$, $NR^5C(O)R^6$, $NR^5C(O)NR^6R^6$, $C(O)R^5$, $C(O)OR^5$, $C(O)NR^5R^6$, $NR^5C(O)OR^6$, F, Cl, Br, I, CN, phenyl, 4-fluorophenyl, 4-chlorophenyl, and 4-methoxyphenyl; or $R^1$ is part of said ring system when said ring system is bicyclic;

$R^2$, $R^3$, and $R^4$ are independently selected from $R^5$, $OR^5$, $OC(O)R^5$, $OC(O)OR^5$, $OC(O)NR^5R^6$, $SR^5$, $S(O)R^5$, $S(O)_2R^5$, $S(O)_2OR^5$, $S(O)_2NR^5R^6$, $NR^5R'$, $NR^5C(O)R'$, $NR^5C(O)NR^6R^6$, $C(O)R^5$, $C(O)OR^5$, $C(O)NR^5R^6$, $NR^5C(O)OR^6$, F, Cl, Br, I, CN, 4-fluorophenyl, 4-chlorophenyl, and 4-methoxyphenyl, wherein $R^2$, $R^3$, and $R^4$ are positioned independently in any of the free positions of the mono- or bicyclic aromatic or heteroaromatic ring system;

$R^5$ and $R^6$ are independently selected from hydrogen, $C_1$-$C_{15}$ alkyl, $C_3$-$C_5$ cycloalkyl, phenyl, and $C_1$-$C_3$ haloalkyl;

$R^7$, $R^8$, $R^9$, and $R^{10}$ are independently selected from hydrogen, methyl, ethyl, n-propyl, iso-propyl, and n-butyl; or being selected such that $R^8$ and $R^9$ are connected to form a 4-, 5-, 6-, or 7-membered ring;

X is selected from hydrogen, methyl, ethyl, n-propyl, iso-propyl, n-butyl, iso-butyl, neo-butyl, tert-butyl, cyclopropyl, cyclopentyl, $CF_3$, $CF_2CF_3$, phenyl, benzyl, hydroxy, methoxy, ethoxy, 2-phenylethyl and benzyloxy, wherein said phenyl, 2-phenylethyl and benzyl groups are optionally mono- or di-substituted by substituents independently selected from methyl, ethyl, methoxy, ethoxy, iso-propyloxy, F, and Cl.

In one embodiment of this aspect, there is provided a compound of Formula I, wherein

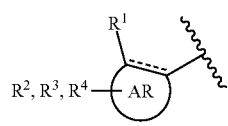

represents

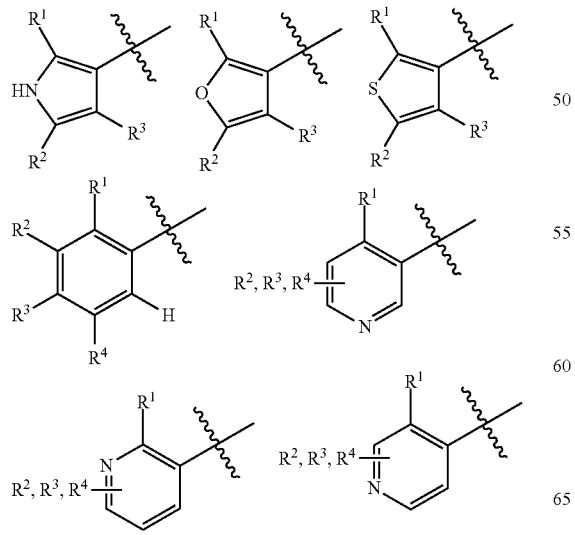

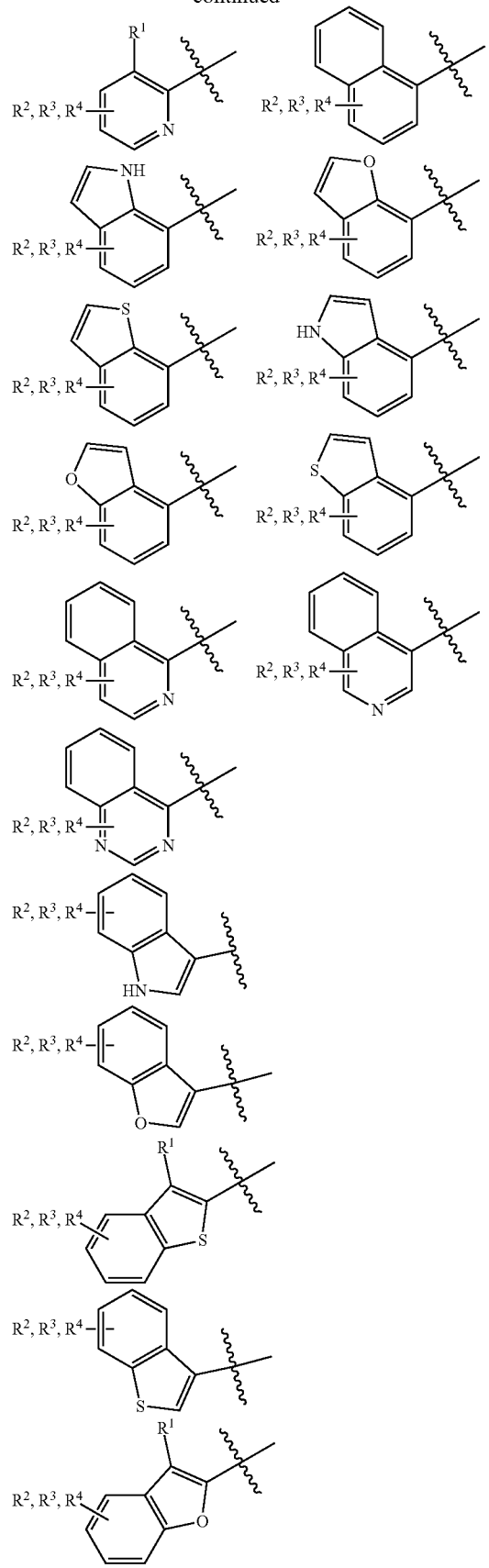

wherein

R$^1$ is selected from methyl, ethyl, iso-propyl, cyclopropyl, CF$_3$, hydroxy, methoxy, ethoxy, iso-propoxy, benzyloxy, OC(O)OCH$_2$CH$_3$, OCF$_3$, SCH$_3$, S(O)$_2$CH$_3$, OC(O)OR$^5$, OC(O)R$^5$, NHCH$_3$, N(CH$_3$)$_2$, NHC(O)H, NHC(O)CH$_3$, NHC(O)NH$_2$, NHC(O)NHCH$_3$, NHC(O)N(CH$_3$)$_2$, C(O)CH$_3$, C(O)N(CH$_3$)$_2$, Cl, Br, I, CN, and phenyl;

R$^2$ is selected from hydrogen, methyl, ethyl, iso-propyl, cyclopropyl, CF$_3$, hydroxy, methoxy, ethoxy, iso-propoxy, OCF$_3$, SCH$_3$, S(O)$_2$CH$_3$, NH$_2$, NHCH$_3$, N(CH$_3$)$_2$, NHC(O)H, NHC(O)CH$_3$, NHC(O)NH$_2$, NHC(O)NHCH$_3$, NHC(O)N(CH$_3$)$_2$, C(O)CH$_3$, C(O)N(CH$_3$)$_2$, F, Cl, Br, I, CN, and phenyl;

R$^3$ is selected from hydrogen, methyl, ethyl, iso-propyl, cyclopropyl, CF$_3$, ethoxy, iso-propoxy, OCF$_3$, SCH$_3$, S(O)$_2$CH$_3$, NH$_2$, NHCH$_3$, N(CH$_3$)$_2$, NHC(O)H, NHC(O)CH$_3$, NHC(O)NH$_2$, NHC(O)NHCH$_3$, NHC(O)N(CH$_3$)$_2$, C(O)CH$_3$, C(O)N(CH$_3$)$_2$, F, Cl, Br, I, CN, and phenyl;

R$^4$ is selected from hydrogen, methyl, ethyl, iso-propyl, cyclopropyl, CF$_3$, hydroxy, methoxy, ethoxy, iso-propoxy, OCF$_3$, SCH$_3$, S(O)$_2$CH$_3$, NH$_2$, NHCH$_3$, N(CH$_3$)$_2$, NHC(O)H, NHC(O)CH$_3$, NHC(O)NH$_2$, NHC(O)NHCH$_3$, NHC(O)N(CH$_3$)$_2$, C(O)CH$_3$, C(O)N(CH$_3$)$_2$, F, Br, I, CN, and phenyl;

R$^5$ represents C$_1$-C$_{15}$ alkyl or phenyl;

R$^7$, R$^8$, R$^9$, and R$^{10}$ are independently selected from hydrogen and methyl; or being selected such that R$^8$ and R$^9$ are connected to form a 5-, or 6-membered ring; and X is selected from hydrogen, C$_1$-C$_{12}$ alkyl, C$_3$-C$_6$ cycloalkyl, C$_1$-C$_4$ fluoroalkyl, phenyl, 2-phenylethyl, benzyl, C(O)OCH$_2$CH$_3$, and hydroxy; wherein said phenyl, 2-phenylethyl, and benzyl are optionally mono- or di-substituted by substituents independently selected from methyl, ethyl, methoxy, F, and Cl, with the proviso that when R$^7$ is methyl and having the configuration as shown in formula Ib, Ib

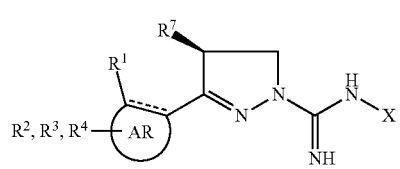

R$^3$ is not hydrogen; and when X, R$^3$, R$^7$ and R$^8$ are simultaneously hydrogen, R$^1$ is not methoxy.

In one embodiment of this aspect, there is provided a compound of Formula I, wherein

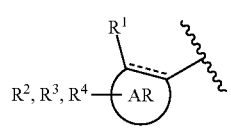

is selected from the group

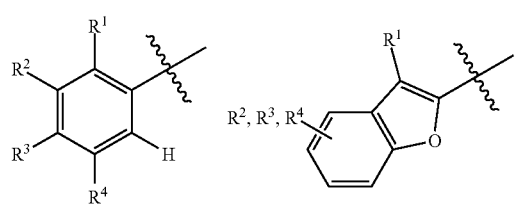

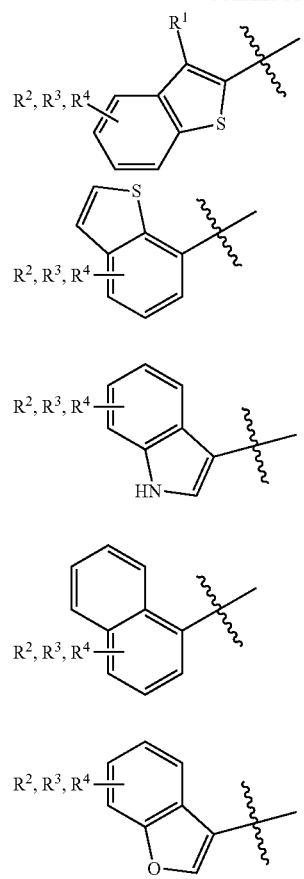

In one embodiment of this aspect, there is provided a compound of Formula I, wherein R$^1$ is selected from C$_1$-C$_3$-alkyl, fluoromethyl, hydroxy, methoxy, benzyloxy, OC(O)OCH$_2$CH$_3$, Cl, and Br;

R$^2$ is selected from hydrogen, F, and Cl;

R$^3$ is selected from hydrogen, fluoromethyl, and F; and

R$^4$ is selected from hydrogen, and F.

In one embodiment of this aspect, there is provided a compound of Formula I, wherein X is selected from hydrogen, C$_1$-C$_{12}$ alkyl, C$_3$-C$_6$ cycloalkyl, phenyl, C$_1$-C$_4$ fluoroalkyl, benzyl, 2-phenylethyl, C(O)OCH$_2$CH$_3$, and hydroxyl, wherein said phenyl, 2-phenylethyl, and benzyl are optionally mono- or di-substituted with substituents independently selected from methyl, fluoromethyl, methoxy, F, and Cl.

High 5-HT$_{2B}$ receptor binding may be obtained with a large variety in the X position in compounds of the invention, as determined in example 120.

In one embodiment of this aspect, there is provided a compound of Formula I, wherein

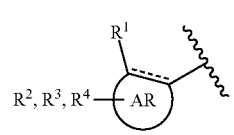

is selected from the group

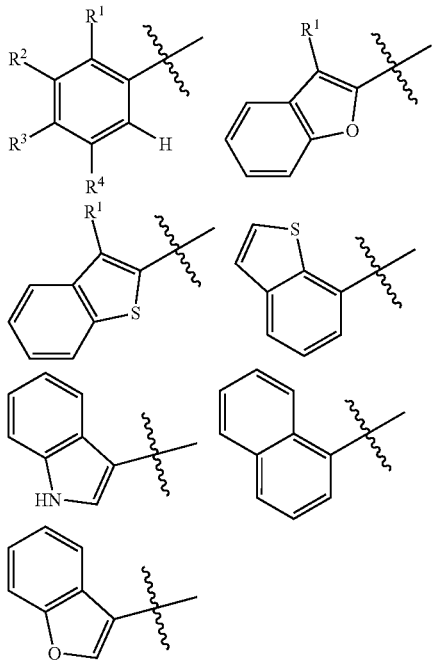

wherein

R¹ is selected from methyl, isopropyl, CF₃, hydroxy, methoxy, benzyloxy, OC(O)OCH₂CH₃, Cl, and Br;

R² is selected from hydrogen, F, and Cl;

R³ is selected from hydrogen, CF₃, and F;

R⁴ is selected from hydrogen, and F;

R⁷, R⁸, R⁹, and R¹⁰ are independently selected from hydrogen, and methyl; or being selected such that R⁸ and R⁹ are connected to form a 5-membered ring;

X is selected from hydrogen, methyl, butyl, hexyl, dodecyl, cyclohexyl, cyclopropyl, phenyl, 2,2,3,3,4,4,4-heptafluorobut-1-yl, 2,2,2-trifluoroeth-1-yl, 4-trifluoromethylphenyl, 4-fluorophenyl, 2-chlorophenyl, 4-chlorophenyl, 4-methoxyphenyl, benzyl, CHCH₃C₆H₅, 4-chlorobenzyl, 4-fluorobenzyl, 2-chlorobenzyl, 2,4-dichlorobenzyl, 3,4-dichlorobenzyl, 4-methoxybenzyl, 3,5-dimethoxybenzyl, 3,4-dimethoxybenzyl, 3-chloro-4-methoxybenzyl, 2-phenylethyl, C(O)OCH₂CH₃, and hydroxy, with the proviso that when R⁷ is methyl and having the configuration as shown in formula Ib, Ib

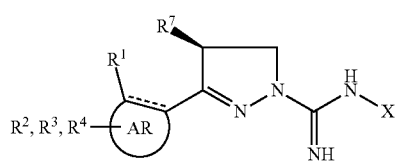

R³ is not hydrogen; and when X, R³, R⁷ and R⁸ are simultaneously hydrogen, R¹ is not methoxy.

In one embodiment of this aspect, there is provided a compound of Formula I, wherein

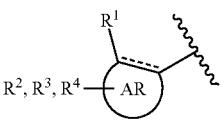

is selected from the group

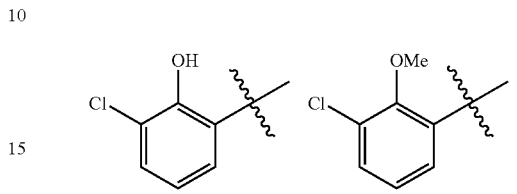

In one embodiment of this aspect, there is provided a compound of Formula I, wherein

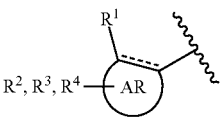

represents

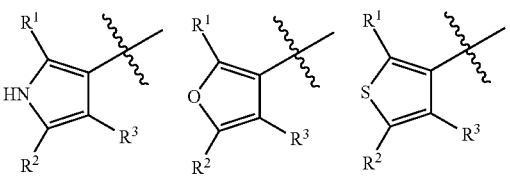

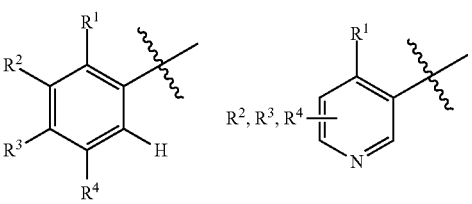

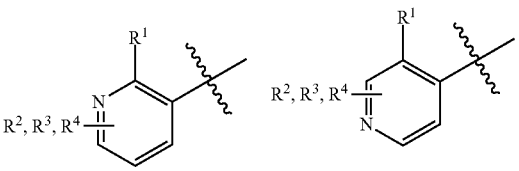

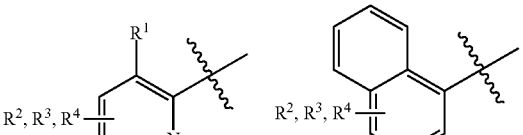

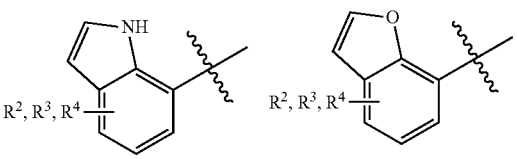

-continued

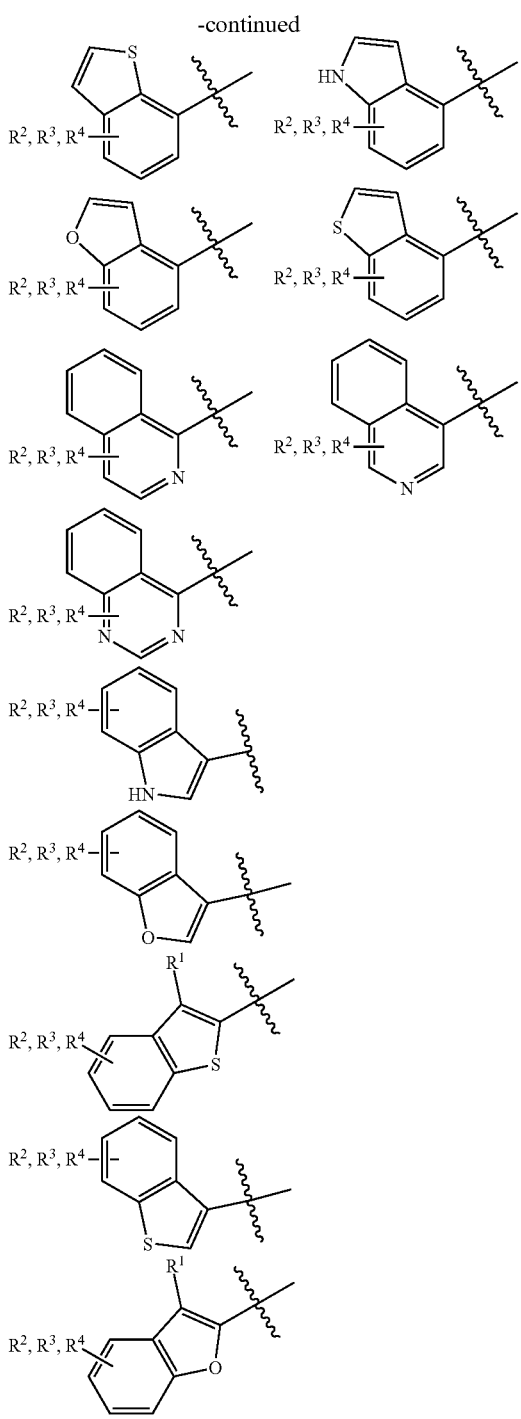

wherein

R¹ is selected from methyl, ethyl, iso-propyl, cyclopropyl, $CF_3$, hydroxy, methoxy, ethoxy, iso-propoxy, $OCF_3$, $SCH_3$, $S(O)_2CH_3$, $OC(O)OR^5$, $OC(O)R^5$, $NHCH_3$, $N(CH_3)_2$, $NHC(O)H$, $NHC(O)CH_3$, $NHC(O)NH_2$, $NHC(O)NHCH_3$, $NHC(O)N(CH_3)_2$, $C(O)CH_3$, $C(O)N(CH_3)_2$, Cl, Br, I, CN, and phenyl, benzyloxy;

R² is selected from hydrogen, methyl, ethyl, iso-propyl, cyclopropyl, $CF_3$, hydroxy, methoxy, ethoxy, iso-propoxy, $OCF_3$, $SCH_3$, $S(O)_2CH_3$, $NH_2$, $NHCH_3$, $N(CH_3)_2$, $NHC(O)H$, $NHC(O)CH_3$, $NHC(O)NH_2$, $NHC(O)NHCH_3$, $NHC(O)N(CH_3)_2$, $C(O)CH_3$, $C(O)N(CH_3)_2$, F, Cl, Br, I, CN, and phenyl;

R³ is selected from hydrogen, methyl, ethyl, iso-propyl, cyclopropyl, $CF_3$, ethoxy, iso-propoxy, $OCF_3$, $SCH_3$, $S(O)_2CH_3$, $NH_2$, $NHCH_3$, $N(CH_3)_2$, $NHC(O)H$, $NHC(O)CH_3$, $NHC(O)NH_2$, $NHC(O)NHCH_3$, $NHC(O)N(CH_3)_2$, $C(O)CH_3$, $C(O)N(CH_3)_2$, F, Cl, Br, I, CN, and phenyl;

R⁴ is selected from hydrogen, methyl, ethyl, iso-propyl, cyclopropyl, $CF_3$, hydroxy, methoxy, ethoxy, iso-propoxy, $OCF_3$, $SCH_3$, $S(O)_2CH_3$, $NH_2$, $NHCH_3$, $N(CH_3)_2$, $NHC(O)H$, $NHC(O)CH_3$, $NHC(O)NH_2$, $NHC(O)NHCH_3$, $NHC(O)N(CH_3)_2$, $C(O)CH_3$, $C(O)N(CH_3)_2$, F, Br, I, CN, and phenyl;

R⁵ represents $C_1$-$C_{15}$ alkyl or phenyl;

R⁷, R⁸, R⁹, and R¹⁰ are independently selected from hydrogen and methyl; or being selected such that R⁸ and R⁹ are connected to form a 5-, or 6-membered ring; and X is selected from hydrogen, methyl, ethyl, n-propyl, iso-propyl, cyclopropyl, cyclopentyl, $CF_3$, $CF_2CF_3$, phenyl, 2-phenylethyl, benzyl, and hydroxy; wherein said phenyl, 2-phenylethyl, and benzyl is optionally mono- or di-substituted by substituents independently selected from methyl, ethyl, methoxy, F, and Cl, with the proviso that when R⁹ is methyl and having the configuration as shown in formula Ib,

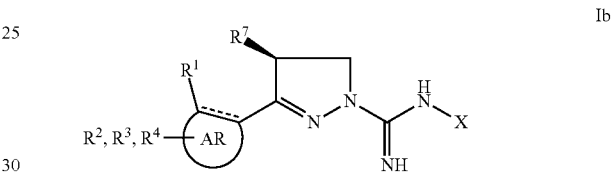

Ib

R³ is not hydrogen; and
when X, R³, R⁷ and R⁸ are simultaneously hydrogen, R¹ is not methoxy.

In one embodiment of this aspect, there is provided a compound of Formula I, wherein

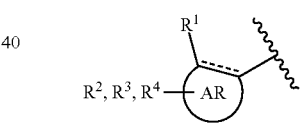

is selected from the group

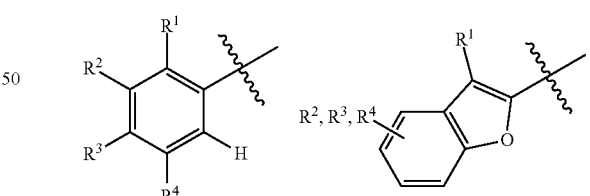

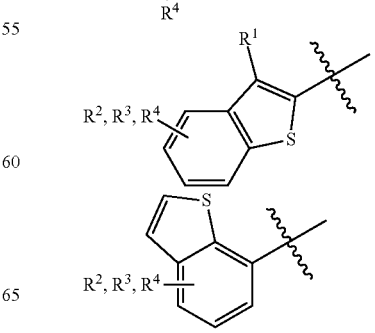

-continued

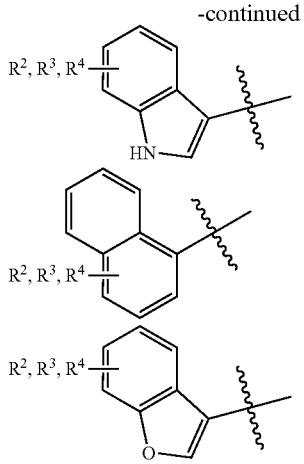

In one embodiment of this aspect, there is provided a compound of Formula I, wherein $R^1$ is selected from $C_1$-$C_3$-alkyl, fluoromethyl, hydroxy, methoxy, Cl, and Br;
$R^2$ is selected from hydrogen, F, and Cl;
$R^3$ is selected from hydrogen, fluoromethyl, and F; and
$R^4$ is selected from hydrogen and F.

In one embodiment of this aspect, there is provided a compound of Formula I, wherein

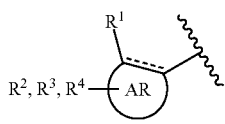

is selected from the group

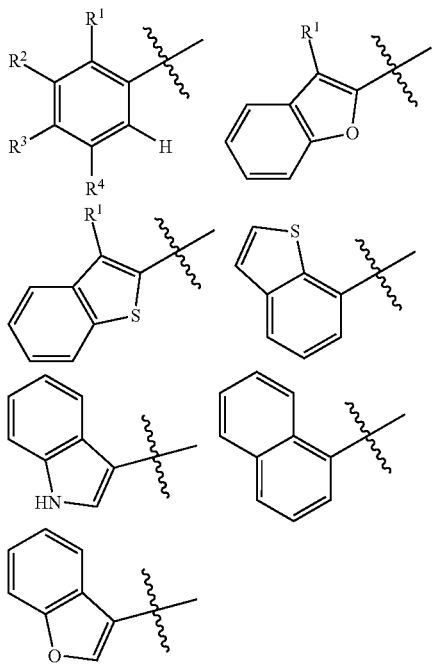

wherein
$R^1$ is selected from methyl, iso-propyl, $CF_3$, hydroxy, methoxy, Cl, and Br;

$R^2$ is selected from hydrogen, F, and Cl;
$R^3$ is selected from hydrogen, $CF_3$, and F;
$R^4$ is selected from hydrogen, and F;
$R^7$, $R^8$, $R^9$, and $R^{10}$ are independently selected from hydrogen, and methyl; or being selected such that $R^8$ and $R^9$ are connected to form a 5-membered ring;
X is selected from hydrogen, methyl, benzyl, $CHCH_3C_6H_5$, 4-chlorobenzyl, 2-chlorobenzyl, 2,4-dichlorobenzyl, 3,4-dichlorobenzyl, 4-methoxybenzyl, 3,5-dimethoxybenzyl, 3,4-dimethoxybenzyl, 3-chloro-4-methoxybenzyl, 2-phenylethyl, and hydroxyl,
with the proviso that when $R^7$ is methyl and having the configuration as shown in formula Ib, Ib

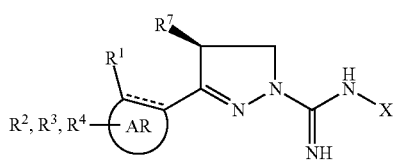

$R^3$ is not hydrogen; and
when X, $R^3$, $R^7$ and $R^8$ are simultaneously hydrogen, $R^1$ is not methoxy.

In one embodiment of this aspect, there is provided a compound of Formula I, wherein
$R^7$ is hydrogen or methyl; and
$R^8$, $R^9$, and $R^{10}$ are hydrogen.

In one embodiment of this aspect, there is provided a compound of Formula I, wherein X is benzyl. It is to be understood that said benzyl is optionally mono- or di-substituted by substituents independently selected from methyl, ethyl, methoxy, ethoxy, iso-propyloxy, F, and Cl.

In one embodiment of this aspect, there is provided a compound of Formula I, wherein
$R^7$ is methyl; and
$R^8$, $R^9$, and $R^{10}$ are hydrogen.

In one embodiment of this aspect, there is provided a compound of Formula I, wherein
$R^7$ is methyl and having the configuration as shown in formula Ia Ia

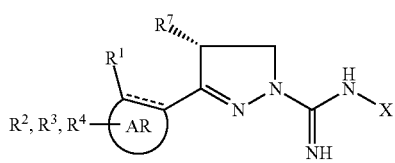

In one embodiment of this aspect, there is provided a compound of Formula I, said compound being selected from:
3-(2-Methoxyphenyl)-4,5-dihydro-1H-pyrazole-1-carboximidamide;
3-(2-Hydroxyphenyl)-4,5-dihydro-1H-pyrazole-1-carboximidamide;
3-(2-Bromophenyl)-4,5-dihydro-1H-pyrazole-1-carboximidamide;
3-(2-Chlorophenyl)-4,5-dihydro-1H-pyrazole-1-carboximidamide;
3-(2-Methylphenyl)-4,5-dihydro-1H-pyrazole-1-carboximidamide;

3-(2,5-Difluorophenyl)-4,5-dihydro-1H-pyrazole-1-carboximidamide;
3-(2-Isopropylphenyl)-4,5-dihydro-1H-pyrazole-1-carboximidamide;
3-(Naphthalen-1-yl)-4,5-dihydro-1H-pyrazole-1-carboximidamide;
3-(Benzo[b]thiophen-7-yl)-4,5-dihydro-1H-pyrazole-1-carboximidamide;
3-(2-Fluorophenyl)-4,5-dihydro-1H-pyrazole-1-carboximidamide;
3-(2-(Trifluoromethyl)phenyl)-4,5-dihydro-1H-pyrazole-1-carboximidamide;
3-(Benzofuran-3-yl)-4,5-dihydro-1H-pyrazole-1-carboximidamide;
3-(2-Hydroxyphenyl)-4-methyl-4,5-dihydro-1H-pyrazole-1-carboximidamide;
3-(2-Methoxyphenyl)-4-methyl-4,5-dihydro-1H-pyrazole-1-carboximidamide;
3-(2-Chlorophenyl)-N-methyl-4,5-dihydro-1H-pyrazole-1-carboximidamide;
3-(2-Hydroxyphenyl)-N-methyl-4,5-dihydro-1H-pyrazole-1-carboximidamide;
N-Benzyl-3-(2-chlorophenyl)-4,5-dihydro-1H-pyrazole-1-carboximidamide;
N-Benzyl-3-(2-hydroxyphenyl)-4,5-dihydro-1H-pyrazole-1-carboximidamide;
5-methyl-3-(naphthalen-1-yl)-4,5-dihydro-1H-pyrazole-1-carboximidamide;
3-(2-Chlorophenyl)-5-methyl-4,5-dihydro-1H-pyrazole-1-carboximidamide;
3-(2,6-Difluorophenyl)-5-methyl-4,5-dihydro-1H-pyrazole-1-carboximidamide;
3-(2-Chlorophenyl)-5-ethyl-4,5-dihydro-1H-pyrazole-1-carboximidamide;
5-Methyl-3-(3-methylbenzofuran-2-yl)-4,5-dihydro-1H-pyrazole-1-carboximidamide;
5-Methyl-3-(3-methylbenzo[b]thiophen-2-yl)-4,5-dihydro-1H-pyrazole-1-carboximidamide;
3-(2-Chlorophenyl)-4,5,6,6a-tetrahydrocyclopenta[c]pyrazole-1(3aH)-carboximidamide;
3-(2-Aminophenyl)-4,5-dihydro-1H-pyrazole-1-carboximidamide;
3-(2-Hydroxyphenyl)-4,4-dimethyl-4,5-dihydro-1H-pyrazole-1-carboximidamide;
3-(2-Chloro-6-methoxyphenyl)-4,5-dihydro-1H-pyrazole-1-carboximidamide;
3-(2-Chloro-6-hydroxyphenyl)-4,5-dihydro-1H-pyrazole-1-carboximidamide;
(S)-3-(2-Hydroxyphenyl)-4-methyl-4,5-dihydro-1H-pyrazole-1-carboximidamide;
(R)-3-(2-Hydroxyphenyl)-4-methyl-4,5-dihydro-1H-pyrazole-1-carboximidamide;
(S)-3-(2-Hydroxyphenyl)-4-methyl-4,5-dihydro-1H-pyrazole-1-carboximidamide;
(R)-3-(2-Hydroxyphenyl)-4-methyl-4,5-dihydro-1H-pyrazole-1-carboximidamide;
3-(2-Methoxyphenyl)-N,4-dimethyl-4,5-dihydro-1H-pyrazole-1-carboximidamide;
3-(2-Hydroxyphenyl)-N,4-dimethyl-4,5-dihydro-1H-pyrazole-1-carboximidamide;
N-Benzyl-3-(2-methoxyphenyl)-4-methyl-4,5-dihydro-1H-pyrazole-1-carboximidamide;
N-Benzyl-3-(2-hydroxyphenyl)-4-methyl-4,5-dihydro-1H-pyrazole-1-carboximidamide;
N-Hydroxy-3-(2-methoxyphenyl)-4-methyl-4,5-dihydro-1H-pyrazole-1-carboximidamide;
N-Hydroxy-3-(2-hydroxyphenyl)-4-methyl-4,5-dihydro-1H-pyrazole-1-carboximidamide;
3-(5-Fluoro-2-methoxyphenyl)-4-methyl-4,5-dihydro-1H-pyrazole-1-carboximidamide
3-(5-Fluoro-2-hydroxyphenyl)-4-methyl-4,5-dihydro-1H-pyrazole-1-carboximidamide;
3-(3-Fluoro-2-methoxyphenyl)-4-methyl-4,5-dihydro-1H-pyrazole-1-carboximidamide;
3-(3-Fluoro-2-hydroxyphenyl)-4-methyl-4,5-dihydro-1H-pyrazole-1-carboximidamide;
3-(4-Fluoro-2-methoxyphenyl)-4-methyl-4,5-dihydro-1H-pyrazole-1-carboximidamide;
3-(4-Fluoro-2-hydroxyphenyl)-4-methyl-4,5-dihydro-1H-pyrazole-1-carboximidamide;
3-(5-Chloro-2-methoxyphenyl)-4-methyl-4,5-dihydro-1H-pyrazole-1-carboximidamide;
3-(5-Chloro-2-hydroxyphenyl)-4-methyl-4,5-dihydro-1H-pyrazole-1-carboximidamide;
3-(3-Chloro-2-methoxyphenyl)-4-methyl-4,5-dihydro-1H-pyrazole-1-carboximidamide;
3-(3-Chloro-2-hydroxyphenyl)-4-methyl-4,5-dihydro-1H-pyrazole-1-carboximidamide;
N-(4-Chlorobenzyl)-3-(2-hydroxyphenyl)-4-methyl-4,5-dihydro-1H-pyrazole-1-carboximidamide;
N-(2-Chlorobenzyl)-3-(2-hydroxyphenyl)-4-methyl-4,5-dihydro-1H-pyrazole-1-carboximidamide;
N-(2,4-Dichlorobenzyl)-3-(2-hydroxyphenyl)-4-methyl-4,5-dihydro-1H-pyrazole-1-carboximidamide;
N-(3,4-Dichlorobenzyl)-3-(2-hydroxyphenyl)-4-methyl-4,5-dihydro-1H-pyrazole-1-carboximidamide;
3-(2-Hydroxyphenyl)-N-(4-methoxybenzyl)-4-methyl-4,5-dihydro-1H-pyrazole-1-carboximidamide;
N-(3,4-Dimethoxybenzyl)-3-(2-hydroxyphenyl)-4-methyl-4,5-dihydro-1H-pyrazole-1-carboximidamide;
N-(3,5-Dimethoxybenzyl)-3-(2-hydroxyphenyl)-4-methyl-4,5-dihydro-1H-pyrazole-1-carboximidamide;
N-(3-chloro-4-methoxybenzyl)-3-(2-hydroxyphenyl)-4-methyl-4,5-dihydro-1H-pyrazole-1-carboximidamide;
3-(2-Hydroxyphenyl)-4-methyl-N—((R)-1-phenylethyl)-4,5-dihydro-1H-pyrazole-1-carboximidamide;
3-(2-Hydroxyphenyl)-4-methyl-N—((S)-1-phenylethyl)-4,5-dihydro-1H-pyrazole-1-carboximidamide;
3-(2-hydroxyphenyl)-4-methyl-N-phenethyl-4,5-dihydro-1H-pyrazole-1-carboximidamide;
3-(2,4-Dimethoxyphenyl)-4-methyl-4,5-dihydro-1H-pyrazole-1-carboximidamide;
3-(2,4-Dihydroxyphenyl)-4-methyl-4,5-dihydro-1H-pyrazole-1-carboximidamide;
3-(2-Methoxy-4-(trifluoromethyl)phenyl)-4-methyl-4,5-dihydro-1H-pyrazole-1-carboximidamide;
3-(2-Hydroxy-4-(trifluoromethyl)phenyl)-4-methyl-4,5-dihydro-1H-pyrazole-1-carboximidamide;
3-(1H-Indol-3-yl)-4-methyl-4,5-dihydro-1H-pyrazole-1-carboximidamide; and
4-Methyl-3-(quinolin-4-yl)-4,5-dihydro-1H-pyrazole-1-carboximidamide.

In one embodiment of this aspect, there is provided a compound of Formula I, said compound being selected from:
3-(2-Hydroxyphenyl)-4,5-dihydro-1H-pyrazole-1-carboximidamide;
3-(2-Bromophenyl)-4,5-dihydro-1H-pyrazole-1-carboximidamide;
3-(2-Chlorophenyl)-4,5-dihydro-1H-pyrazole-1-carboximidamide;
3-(2-Methylphenyl)-4,5-dihydro-1H-pyrazole-1-carboximidamide;

3-(2-Isopropylphenyl)-4,5-dihydro-1H-pyrazole-1-carboximidamide;
3-(Naphthalen-1-yl)-4,5-dihydro-1H-pyrazole-1-carboximidamide;
3-(Benzo[b]thiophen-7-yl)-4,5-dihydro-1H-pyrazole-1-carboximidamide;
3-(2-(Trifluoromethyl)phenyl)-4,5-dihydro-1H-pyrazole-1-carboximidamide;
3-(Benzofuran-3-yl)-4,5-dihydro-1H-pyrazole-1-carboximidamide;
3-(2-Hydroxyphenyl)-4-methyl-4,5-dihydro-1H-pyrazole-1-carboximidamide;
3-(2-Methoxyphenyl)-4-methyl-4,5-dihydro-1H-pyrazole-1-carboximidamide;
3-(2-Chlorophenyl)-N-methyl-4,5-dihydro-1H-pyrazole-1-carboximidamide;
3-(2-Hydroxyphenyl)-N-methyl-4,5-dihydro-1H-pyrazole-1-carboximidamide;
N-Benzyl-3-(2-chlorophenyl)-4,5-dihydro-1H-pyrazole-1-carboximidamide;
N-Benzyl-3-(2-hydroxyphenyl)-4,5-dihydro-1H-pyrazole-1-carboximidamide;
5-methyl-3-(naphthalen-1-yl)-4,5-dihydro-1H-pyrazole-1-carboximidamide;
4-Methyl-3-(naphthalen-1-yl)-4,5-dihydro-1H-pyrazole-1-carboximidamide;
3-(2-Chlorophenyl)-5-methyl-4,5-dihydro-1H-pyrazole-1-carboximidamide;
5-Methyl-3-(3-methylbenzofuran-2-yl)-4,5-dihydro-1H-pyrazole-1-carboximidamide;
5-Methyl-3-(3-methylbenzo[b]thiophen-2-yl)-4,5-dihydro-1H-pyrazole-1-carboximidamide;
3-(2-Chlorophenyl)-4,5,6,6a-tetrahydrocyclopenta[c]pyrazole-1(3aH)-carboximidamide;
(R)-3-(2-Hydroxyphenyl)-4-methyl-4,5-dihydro-1H-pyrazole-1-carboximidamide;
3-(2-Methoxyphenyl)-N,4-dimethyl-4,5-dihydro-1H-pyrazole-1-carboximidamide;
3-(2-Hydroxyphenyl)-N,4-dimethyl-4,5-dihydro-1H-pyrazole-1-carboximidamide;
N-Benzyl-3-(2-methoxyphenyl)-4-methyl-4,5-dihydro-1H-pyrazole-1-carboximidamide;
N-Benzyl-3-(2-hydroxyphenyl)-4-methyl-4,5-dihydro-1H-pyrazole-1-carboximidamide;
N-Hydroxy-3-(2-methoxyphenyl)-4-methyl-4,5-dihydro-1H-pyrazole-1-carboximidamide;
N-Hydroxy-3-(2-hydroxyphenyl)-4-methyl-4,5-dihydro-1H-pyrazole-1-carboximidamide;
3-(5-Fluoro-2-methoxyphenyl)-4-methyl-4,5-dihydro-1H-pyrazole-1-carboximidamide
3-(5-Fluoro-2-hydroxyphenyl)-4-methyl-4,5-dihydro-1H-pyrazole-1-carboximidamide;
3-(3-Fluoro-2-methoxyphenyl)-4-methyl-4,5-dihydro-1H-pyrazole-1-carboximidamide;
3-(3-Fluoro-2-hydroxyphenyl)-4-methyl-4,5-dihydro-1H-pyrazole-1-carboximidamide;
3-(4-Fluoro-2-methoxyphenyl)-4-methyl-4,5-dihydro-1H-pyrazole-1-carboximidamide;
3-(4-Fluoro-2-hydroxyphenyl)-4-methyl-4,5-dihydro-1H-pyrazole-1-carboximidamide;
3-(5-Chloro-2-hydroxyphenyl)-4-methyl-4,5-dihydro-1H-pyrazole-1-carboximidamide;
3-(3-Chloro-2-methoxyphenyl)-4-methyl-4,5-dihydro-1H-pyrazole-1-carboximidamide;
3-(3-Chloro-2-hydroxyphenyl)-4-methyl-4,5-dihydro-1H-pyrazole-1-carboximidamide;
N-(4-Chlorobenzyl)-3-(2-hydroxyphenyl)-4-methyl-4,5-dihydro-1H-pyrazole-1-carboximidamide;
N-(2-Chlorobenzyl)-3-(2-hydroxyphenyl)-4-methyl-4,5-dihydro-1H-pyrazole-1-carboximidamide;
N-(2,4-Dichlorobenzyl)-3-(2-hydroxyphenyl)-4-methyl-4,5-dihydro-1H-pyrazole-1-carboximidamide;
N-(3,4-Dichlorobenzyl)-3-(2-hydroxyphenyl)-4-methyl-4,5-dihydro-1H-pyrazole-1-carboximidamide;
3-(2-Hydroxyphenyl)-N-(4-methoxybenzyl)-4-methyl-4,5-dihydro-1H-pyrazole-1-carboximidamide;
N-(3,4-Dimethoxybenzyl)-3-(2-hydroxyphenyl)-4-methyl-4,5-dihydro-1H-pyrazole-1-carboximidamide;
N-(3,5-Dimethoxybenzyl)-3-(2-hydroxyphenyl)-4-methyl-4,5-dihydro-1H-pyrazole-1-carboximidamide;
N-(3-chloro-4-methoxybenzyl)-3-(2-hydroxyphenyl)-4-methyl-4,5-dihydro-1H-pyrazole-1-carboximidamide;
3-(2-Hydroxyphenyl)-4-methyl-N—((R)-1-phenylethyl)-4,5-dihydro-1H-pyrazole-1-carboximidamide;
3-(2-Hydroxyphenyl)-4-methyl-N—((S)-1-phenylethyl)-4,5-dihydro-1H-pyrazole-1-carboximidamide;
3-(2-hydroxyphenyl)-4-methyl-N-phenethyl-4,5-dihydro-1H-pyrazole-1-carboximidamide;
3-(2-Methoxy-4-(trifluoromethyl)phenyl)-4-methyl-4,5-dihydro-1H-pyrazole-1-carboximidamide;
3-(2-Hydroxy-4-(trifluoromethyl)phenyl)-4-methyl-4,5-dihydro-1H-pyrazole-1-carboximidamide;
3-(1H-Indol-3-yl)-4-methyl-4,5-dihydro-1H-pyrazole-1-carboximidamide.

In one embodiment of this aspect, there is provided a compound of Formula I, said compound being selected from:
4-Methyl-3-(naphthalen-1-yl)-4,5-dihydro-1H-pyrazole-1-carboximidamide;
(S)-3-(3-chloro-2-hydroxyphenyl)-4-methyl-4,5-dihydro-1H-pyrazole-1-carboximidamide;
(R)-3-(3-chloro-2-hydroxyphenyl)-4-methyl-4,5-dihydro-1H-pyrazole-1-carboximidamide;
N-Benzyl-3-(3-chloro-2-methoxyphenyl)-4-methyl-4,5-dihydro-1H-pyrazole-1-carboximidamide;
N-Benzyl-3-(3-chloro-2-hydroxyphenyl)-4-methyl-4,5-dihydro-1H-pyrazole-1-carboximidamide;
(R)—N-Benzyl-3-(3-chloro-2-hydroxyphenyl)-4-methyl-4,5-dihydro-1H-pyrazole-1-carboximidamide;
(S)—N-Benzyl-3-(3-chloro-2-hydroxyphenyl)-4-methyl-4,5-dihydro-1H-pyrazole-1-carboximidamide;
N-Butyl-3-(3-chloro-2-methoxyphenyl)-4-methyl-4,5-dihydro-1H-pyrazole-1-carboximidamide;
N-Butyl-3-(3-chloro-2-hydroxyphenyl)-4-methyl-4,5-dihydro-1H-pyrazole-1-carboximidamide;
3-(3-Chloro-2-methoxyphenyl)-N-hexyl-4-methyl-4,5-dihydro-1H-pyrazole-1-carboximidamide;
3-(3-Chloro-2-hydroxyphenyl)-N-hexyl-4-methyl-4,5-dihydro-1H-pyrazole-1-carboximidamide;
3-(3-Chloro-2-methoxyphenyl)-N-dodecyl-4-methyl-4,5-dihydro-1H-pyrazole-1-carboximidamide;
3-(3-Chloro-2-hydroxyphenyl)-N-dodecyl-4-methyl-4,5-dihydro-1H-pyrazole-1-carboximidamide;
3-(3-Chloro-2-methoxyphenyl)-N-cyclohexyl-4-methyl-4,5-dihydro-1H-pyrazole-1-carboximidamide;
3-(3-Chloro-2-hydroxyphenyl)-N-cyclohexyl-4,5-dihydro-1H-pyrazole-1-carboximidamide;
3-(3-Chloro-2-methoxyphenyl)-N-cyclopropyl-4-methyl-4,5-dihydro-1H-pyrazole-1-carboximidamide;
3-(3-Chloro-2-hydroxyphenyl)-N-cyclopropyl-4-methyl-4,5-dihydro-1H-pyrazole-1-carboximidamide;
3-(3-Chloro-2-methoxyphenyl)-4-methyl-N-phenyl-4,5-dihydro-1H-pyrazole-1-carboximidamide;

3-(3-Chloro-2-hydroxyphenyl)-4-methyl-N-phenyl-4,5-dihydro-1H-pyrazole-1-carboximidamide;
3-(3-Chloro-2-methoxyphenyl)-N-cyano-4-methyl-4,5-dihydro-1H-pyrazole-1-carboximidamide;
3-(3-Chloro-2-hydroxyphenyl)-N-cyano-4-methyl-4,5-dihydro-1H-pyrazole-1-carboximidamide;
N-(2,2,3,3,4,4,4-Heptafluorobutyl)-3-(2-methoxyphenyl)-4-methyl-4,5-dihydro-1H-pyrazole-1-carboximidamide;
N-(2,2,3,3,4,4,4-Heptafluorobutyl)-3-(2-hydroxyphenyl)-4-methyl-4,5-dihydro-1H-pyrazole-1-carboximidamide;
3-(2-Methoxyphenyl)-4-methyl-N-(2,2,2-trifluoroethyl)-4,5-dihydro-1H-pyrazole-1-carboximidamide;
3-(2-Hydroxyphenyl)-4-methyl-N-(2,2,2-trifluoroethyl)-4,5-dihydro-1H-pyrazole-1-carboximidamide;
3-(2-Methoxyphenyl)-4-methyl-N-phenyl-4,5-dihydro-1H-pyrazole-1-carboximidamide;
3-(2-Hydroxyphenyl)-4-methyl-N-phenyl-4,5-dihydro-1H-pyrazole-1-carboximidamide;
3-(2-Methoxyphenyl)-4-methyl-N-(4-(trifluoromethyl)phenyl)-4,5-dihydro-1H-pyrazole-1-carboximidamide;
3-(2-Hydroxyphenyl)-4-methyl-N-(4-(trifluoromethyl)phenyl)-4,5-dihydro-1H-pyrazole-1-carboximidamide;
N-(4-Fluorophenyl)-3-(2-methoxyphenyl)-4-methyl-4,5-dihydro-1H-pyrazole-1-carboximidamide;
N-(4-Fluorophenyl)-3-(2-hydroxyphenyl)-4-methyl-4,5-dihydro-1H-pyrazole-1-carboximidamide;
N-(4-Chlorophenyl)-3-(2-methoxyphenyl)-4-methyl-4,5-dihydro-1H-pyrazole-1-carboximidamide;
N-(4-Chlorophenyl)-3-(2-hydroxyphenyl)-4-methyl-4,5-dihydro-1H-pyrazole-1-carboximidamide;
3-(2-(Benzyloxy)phenyl)-N-(4-methoxyphenyl)-4-methyl-4,5-dihydro-1H-pyrazole-1-carboximidamide;
3-(2-Hydroxyphenyl)-N-(4-methoxyphenyl)-4-methyl-4,5-dihydro-1H-pyrazole-1-carboximidamide;
3-(3-Chloro-2-methoxyphenyl)-N-(2,2,3,3,4,4,4-heptafluorobutyl)-4-methyl-4,5-dihydro-1H-pyrazole-1-carboximidamide;
3-(3-Chloro-2-hydroxyphenyl)-N-(2,2,3,3,4,4,4-heptafluorobutyl)-4-methyl-4,5-dihydro-1H-pyrazole-1-carboximidamide;
3-(3-Chloro-2-methoxyphenyl)-N-(4-fluorophenyl)-4-methyl-4,5-dihydro-1H-pyrazole-1-carboximidamide;
3-(3-Chloro-2-hydroxyphenyl)-N-(4-fluorophenyl)-4-methyl-4,5-dihydro-1H-pyrazole-1-carboximidamide;
3-(3-Chloro-2-methoxyphenyl)-N-(4-chlorophenyl)-4-methyl-4,5-dihydro-1H-pyrazole-1-carboximidamide;
3-(3-Chloro-2-hydroxyphenyl)-N-(4-chlorophenyl)-4-methyl-4,5-dihydro-1H-pyrazole-1-carboximidamide;
3-(3-Chloro-2-methoxyphenyl)-4-methyl-N-(4-(trifluoromethyl)phenyl)-4,5-dihydro-1H-pyrazole-1-carboximidamide;
3-(3-Chloro-2-hydroxyphenyl)-4-methyl-N-(4-(trifluoromethyl)phenyl)-4,5-dihydro-1H-pyrazole-1-carboximidamide;
3-(3-Chloro-2-methoxyphenyl)-N-(2-chlorophenyl)-4-methyl-4,5-dihydro-1H-pyrazole-1-carboximidamide;
3-(3-Chloro-2-hydroxyphenyl)-N-(2-chlorophenyl)-4-methyl-4,5-dihydro-1H-pyrazole-1-carboximidamide;
3-(3-Chloro-2-methoxyphenyl)-N-(4-fluorobenzyl)-4-methyl-4,5-dihydro-1H-pyrazole-1-carboximidamide;
3-(3-Chloro-2-hydroxyphenyl)-N-(4-fluorobenzyl)-4-methyl-4,5-dihydro-1H-pyrazole-1-carboximidamide;
Ethyl((3-(3-chloro-2-((ethoxycarbonyl)oxy)phenyl)-4-methyl-4,5-dihydro-1H-pyrazol-1-yl)(imino)methyl)carbamate;
Ethyl ((3-(3-chloro-2-hydroxyphenyl)-4-methyl-4,5-dihydro-1H-pyrazol-1-yl)(imino)methyl)carbamate.

In one embodiment of this aspect, there is provided a compound of Formula I, said compound being selected from:
4-Methyl-3-(naphthalen-1-yl)-4,5-dihydro-1H-pyrazole-1-carboximidamide;
3-(2-Hydroxyphenyl)-4,5-dihydro-1H-pyrazole-1-carboximidamide;
3-(2-Bromophenyl)-4,5-dihydro-1H-pyrazole-1-carboximidamide;
3-(2-Chlorophenyl)-4,5-dihydro-1H-pyrazole-1-carboximidamide;
3-(2-Methylphenyl)-4,5-dihydro-1H-pyrazole-1-carboximidamide;
3-(2-Isopropylphenyl)-4,5-dihydro-1H-pyrazole-1-carboximidamide;
3-(Naphthalen-1-yl)-4,5-dihydro-1H-pyrazole-1-carboximidamide;
3-(Benzo[b]thiophen-7-yl)-4,5-dihydro-1H-pyrazole-1-carboximidamide;
3-(2-(Trifluoromethyl)phenyl)-4,5-dihydro-1H-pyrazole-1-carboximidamide;
3-(Benzofuran-3-yl)-4,5-dihydro-1H-pyrazole-1-carboximidamide;
3-(2-Hydroxyphenyl)-4-methyl-4,5-dihydro-1H-pyrazole-1-carboximidamide;
3-(2-Methoxyphenyl)-4-methyl-4,5-dihydro-1H-pyrazole-1-carboximidamide;
3-(2-Chlorophenyl)-N-methyl-4,5-dihydro-1H-pyrazole-1-carboximidamide;
3-(2-Hydroxyphenyl)-N-methyl-4,5-dihydro-1H-pyrazole-1-carboximidamide;
N-Benzyl-3-(2-chlorophenyl)-4,5-dihydro-1H-pyrazole-1-carboximidamide;
N-Benzyl-3-(2-hydroxyphenyl)-4,5-dihydro-1H-pyrazole-1-carboximidamide;
5-methyl-3-(naphthalen-1-yl)-4,5-dihydro-1H-pyrazole-1-carboximidamide;
3-(2-Chlorophenyl)-5-methyl-4,5-dihydro-1H-pyrazole-1-carboximidamide;
5-Methyl-3-(3-methylbenzofuran-2-yl)-4,5-dihydro-1H-pyrazole-1-carboximidamide;
5-Methyl-3-(3-methylbenzo[b]thiophen-2-yl)-4,5-dihydro-1H-pyrazole-1-carboximidamide;
3-(2-Chlorophenyl)-4,5,6,6a-tetrahydrocyclopenta[c]pyrazole-1(3aH)-carboximidamide;
(R)-3-(2-Hydroxyphenyl)-4-methyl-4,5-dihydro-1H-pyrazole-1-carboximidamide;
3-(2-Methoxyphenyl)-N,4-dimethyl-4,5-dihydro-1H-pyrazole-1-carboximidamide;
3-(2-Hydroxyphenyl)-N,4-dimethyl-4,5-dihydro-1H-pyrazole-1-carboximidamide;
N-Benzyl-3-(2-methoxyphenyl)-4-methyl-4,5-dihydro-1H-pyrazole-1-carboximidamide;
N-Benzyl-3-(2-hydroxyphenyl)-4-methyl-4,5-dihydro-1H-pyrazole-1-carboximidamide;
N-Hydroxy-3-(2-methoxyphenyl)-4-methyl-4,5-dihydro-1H-pyrazole-1-carboximidamide;
N-Hydroxy-3-(2-hydroxyphenyl)-4-methyl-4,5-dihydro-1H-pyrazole-1-carboximidamide;
3-(5-Fluoro-2-methoxyphenyl)-4-methyl-4,5-dihydro-1H-pyrazole-1-carboximidamide
3-(5-Fluoro-2-hydroxyphenyl)-4-methyl-4,5-dihydro-1H-pyrazole-1-carboximidamide;
3-(3-Fluoro-2-methoxyphenyl)-4-methyl-4,5-dihydro-1H-pyrazole-1-carboximidamide;
3-(3-Fluoro-2-hydroxyphenyl)-4-methyl-4,5-dihydro-1H-pyrazole-1-carboximidamide;

3-(4-Fluoro-2-methoxyphenyl)-4-methyl-4,5-dihydro-1H-pyrazole-1-carboximidamide;
3-(4-Fluoro-2-hydroxyphenyl)-4-methyl-4,5-dihydro-1H-pyrazole-1-carboximidamide;
3-(5-Chloro-2-hydroxyphenyl)-4-methyl-4,5-dihydro-1H-pyrazole-1-carboximidamide;
3-(3-Chloro-2-methoxyphenyl)-4-methyl-4,5-dihydro-1H-pyrazole-1-carboximidamide;
3-(3-Chloro-2-hydroxyphenyl)-4-methyl-4,5-dihydro-1H-pyrazole-1-carboximidamide;
N-(4-Chlorobenzyl)-3-(2-hydroxyphenyl)-4-methyl-4,5-dihydro-1H-pyrazole-1-carboximidamide;
N-(2-Chlorobenzyl)-3-(2-hydroxyphenyl)-4-methyl-4,5-dihydro-1H-pyrazole-1-carboximidamide;
N-(2,4-Dichlorobenzyl)-3-(2-hydroxyphenyl)-4-methyl-4,5-dihydro-1H-pyrazole-1-carboximidamide;
N-(3,4-Dichlorobenzyl)-3-(2-hydroxyphenyl)-4-methyl-4,5-dihydro-1H-pyrazole-1-carboximidamide;
3-(2-Hydroxyphenyl)-N-(4-methoxybenzyl)-4-methyl-4,5-dihydro-1H-pyrazole-1-carboximidamide;
N-(3,4-Dimethoxybenzyl)-3-(2-hydroxyphenyl)-4-methyl-4,5-dihydro-1H-pyrazole-1-carboximidamide;
N-(3,5-Dimethoxybenzyl)-3-(2-hydroxyphenyl)-4-methyl-4,5-dihydro-1H-pyrazole-1-carboximidamide;
N-(3-chloro-4-methoxybenzyl)-3-(2-hydroxyphenyl)-4-methyl-4,5-dihydro-1H-pyrazole-1-carboximidamide;
3-(2-Hydroxyphenyl)-4-methyl-N—((R)-1-phenylethyl)-4,5-dihydro-1H-pyrazole-1-carboximidamide;
3-(2-Hydroxyphenyl)-4-methyl-N—((S)-1-phenylethyl)-4,5-dihydro-1H-pyrazole-1-carboximidamide;
3-(2-hydroxyphenyl)-4-methyl-N-phenethyl-4,5-dihydro-1H-pyrazole-1-carboximidamide;
3-(2-Methoxy-4-(trifluoromethyl)phenyl)-4-methyl-4,5-dihydro-1H-pyrazole-1-carboximidamide;
3-(2-Hydroxy-4-(trifluoromethyl)phenyl)-4-methyl-4,5-dihydro-1H-pyrazole-1-carboximidamide;
3-(1H-Indol-3-yl)-4-methyl-4,5-dihydro-1H-pyrazole-1-carboximidamide;
(S)-3-(3-chloro-2-hydroxyphenyl)-4-methyl-4,5-dihydro-1H-pyrazole-1-carboximidamide;
(R)-3-(3-chloro-2-hydroxyphenyl)-4-methyl-4,5-dihydro-1H-pyrazole-1-carboximidamide;
N-Benzyl-3-(3-chloro-2-methoxyphenyl)-4-methyl-4,5-dihydro-1H-pyrazole-1-carboximidamide;
N-Benzyl-3-(3-chloro-2-hydroxyphenyl)-4-methyl-4,5-dihydro-1H-pyrazole-1-carboximidamide;
(R)—N-Benzyl-3-(3-chloro-2-hydroxyphenyl)-4-methyl-4,5-dihydro-1H-pyrazole-1-carboximidamide;
(S)—N-Benzyl-3-(3-chloro-2-hydroxyphenyl)-4-methyl-4,5-dihydro-1H-pyrazole-1-carboximidamide;
N-butyl-3-(3-chloro-2-methoxyphenyl)-4-methyl-4,5-dihydro-1H-pyrazole-1-carboximidamide;
N-Butyl-3-(3-chloro-2-hydroxyphenyl)-4-methyl-4,5-dihydro-1H-pyrazole-1-carboximidamide;
3-(3-Chloro-2-methoxyphenyl)-N-hexyl-4-methyl-4,5-dihydro-1H-pyrazole-1-carboximidamide;
3-(3-Chloro-2-hydroxyphenyl)-N-hexyl-4-methyl-4,5-dihydro-1H-pyrazole-1-carboximidamide;
3-(3-Chloro-2-methoxyphenyl)-N-dodecyl-4-methyl-4,5-dihydro-1H-pyrazole-1-carboximidamide;
3-(3-Chloro-2-hydroxyphenyl)-N-dodecyl-4-methyl-4,5-dihydro-1H-pyrazole-1-carboximidamide;
3-(3-Chloro-2-methoxyphenyl)-N-cyclohexyl-4-methyl-4,5-dihydro-1H-pyrazole-1-carboximidamide;
3-(3-Chloro-2-hydroxyphenyl)-N-cyclohexyl-4-methyl-4,5-dihydro-1H-pyrazole-1-carboximidamide;
3-(3-Chloro-2-methoxyphenyl)-N-cyclopropyl-4-methyl-4,5-dihydro-1H-pyrazole-1-carboximidamide;
3-(3-Chloro-2-hydroxyphenyl)-N-cyclopropyl-4-methyl-4,5-dihydro-1H-pyrazole-1-carboximidamide;
3-(3-Chloro-2-methoxyphenyl)-4-methyl-N-phenyl-4,5-dihydro-1H-pyrazole-1-carboximidamide;
3-(3-Chloro-2-hydroxyphenyl)-4-methyl-N-phenyl-4,5-dihydro-1H-pyrazole-1-carboximidamide;
3-(3-Chloro-2-hydroxyphenyl)-N-cyano-4-methyl-4,5-dihydro-1H-pyrazole-1-carboximidamide;
N-(2,2,3,3,4,4,4-Heptafluorobutyl)-3-(2-methoxyphenyl)-4-methyl-4,5-dihydro-1H-pyrazole-1-carboximidamide;
N-(2,2,3,3,4,4,4-Heptafluorobutyl)-3-(2-hydroxyphenyl)-4-methyl-4,5-dihydro-1H-pyrazole-1-carboximidamide;
3-(2-Methoxyphenyl)-4-methyl-N-(2,2,2-trifluoroethyl)-4,5-dihydro-1H-pyrazole-1-carboximidamide;
3-(2-Hydroxyphenyl)-4-methyl-N-(2,2,2-trifluoroethyl)-4,5-dihydro-1H-pyrazole-1-carboximidamide;
3-(2-Methoxyphenyl)-4-methyl-N-phenyl-4,5-dihydro-1H-pyrazole-1-carboximidamide;
3-(2-Hydroxyphenyl)-4-methyl-N-phenyl-4,5-dihydro-1H-pyrazole-1-carboximidamide;
3-(2-Methoxyphenyl)-4-methyl-N-(4-(trifluoromethyl)phenyl)-4,5-dihydro-1H-pyrazole-1-carboximidamide;
3-(2-Hydroxyphenyl)-4-methyl-N-(4-(trifluoromethyl)phenyl)-4,5-dihydro-1H-pyrazole-1-carboximidamide;
N-(4-Fluorophenyl)-3-(2-methoxyphenyl)-4-methyl-4,5-dihydro-1H-pyrazole-1-carboximidamide;
N-(4-Fluorophenyl)-3-(2-hydroxyphenyl)-4-methyl-4,5-dihydro-1H-pyrazole-1-carboximidamide;
N-(4-Chlorophenyl)-3-(2-methoxyphenyl)-4-methyl-4,5-dihydro-1H-pyrazole-1-carboximidamide;
N-(4-Chlorophenyl)-3-(2-hydroxyphenyl)-4-methyl-4,5-dihydro-1H-pyrazole-1-carboximidamide;
3-(2-(Benzyloxy)phenyl)-N-(4-methoxyphenyl)-4-methyl-4,5-dihydro-1H-pyrazole-1-carboximidamide;
3-(2-Hydroxyphenyl)-N-(4-methoxyphenyl)-4-methyl-4,5-dihydro-1H-pyrazole-1-carboximidamide;
3-(3-Chloro-2-methoxyphenyl)-N-(2,2,3,3,4,4,4-heptafluorobutyl)-4-methyl-4,5-dihydro-1H-pyrazole-1-carboximidamide;
3-(3-Chloro-2-hydroxyphenyl)-N-(2,2,3,3,4,4,4-heptafluorobutyl)-4-methyl-4,5-dihydro-1H-pyrazole-1-carboximidamide;
3-(3-Chloro-2-methoxyphenyl)-N-(4-fluorophenyl)-4-methyl-4,5-dihydro-1H-pyrazole-1-carboximidamide;
3-(3-Chloro-2-hydroxyphenyl)-N-(4-fluorophenyl)-4-methyl-4,5-dihydro-1H-pyrazole-1-carboximidamide;
3-(3-Chloro-2-methoxyphenyl)-N-(4-chlorophenyl)-4-methyl-4,5-dihydro-1H-pyrazole-1-carboximidamide;
3-(3-Chloro-2-hydroxyphenyl)-N-(4-chlorophenyl)-4-methyl-4,5-dihydro-1H-pyrazole-1-carboximidamide;
3-(3-Chloro-2-methoxyphenyl)-4-methyl-N-(4-(trifluoromethyl)phenyl)-4,5-dihydro-1H-pyrazole-1-carboximidamide;
3-(3-Chloro-2-hydroxyphenyl)-4-methyl-N-(4-(trifluoromethyl)phenyl)-4,5-dihydro-1H-pyrazole-1-carboximidamide;
3-(3-Chloro-2-methoxyphenyl)-N-(2-chlorophenyl)-4-methyl-4,5-dihydro-1H-pyrazole-1-carboximidamide;
3-(3-Chloro-2-hydroxyphenyl)-N-(2-chlorophenyl)-4-methyl-4,5-dihydro-1H-pyrazole-1-carboximidamide;
3-(3-Chloro-2-methoxyphenyl)-N-(4-fluorobenzyl)-4-methyl-4,5-dihydro-1H-pyrazole-1-carboximidamide;
3-(3-Chloro-2-hydroxyphenyl)-N-(4-fluorobenzyl)-4-methyl-4,5-dihydro-1H-pyrazole-1-carboximidamide;

Ethyl((3-(3-chloro-2-((ethoxycarbonyl)oxy)phenyl)-4-methyl-4,5-dihydro-1H-pyrazol-1-yl)(imino)methyl)carbamate;

Ethyl ((3-(3-chloro-2-hydroxyphenyl)-4-methyl-4,5-dihydro-1H-pyrazol-1-yl)(imino)methyl)carbamate.

In another aspect of the invention, there is provided a compound of the general formula I

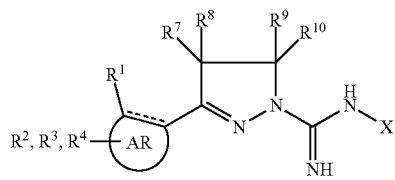

I wherein

AR represents a 5-10 membered mono- or bicyclic aromatic or heteroaromatic ring system containing 0-4 heteroatoms independently selected from N, O, and S;

$R^1$ is selected from $C_1$-$C_6$ alkyl, $C_3$-$C_5$ cycloalkyl, $C_1$-$C_3$ haloalkyl, $OR^5$, $OC(O)R^5$, $OC(O)OR^5$, $OC(O)NR^5R^6$, $SR^5$, $S(O)R^5$, $S(O)_2R^5$, $S(O)_2OR^5$, $S(O)_2NR^5R^6$, $NR^5R^6$, $NR^5C(O)R^6$, $NR^5C(O)NR^6R^6$, $C(O)R^5$, $C(O)OR^5$, $C(O)NR^5R^6$, $NR^5C(O)OR^6$, F, Cl, Br, I, CN, phenyl, 4-fluorophenyl, 4-chlorophenyl, and 4-methoxyphenyl; or $R^1$ is part of said ring system when said ring system is bicyclic;

$R^2$, $R^3$, and $R^4$ are independently selected from $R^5$, $OR^5$, $OC(O)R^5$, $OC(O)OR^5$, $OC(O)NR^5R^6$, $SR^5$, $S(O)R^5$, $S(O)_2R^5$, $S(O)_2OR^5$, $S(O)_2NR^5R^6$, $NR^5R'$, $NR^5C(O)R'$, $NR^5C(O)NR^6R^6$, $C(O)R^5$, $C(O)OR^5$, $C(O)NR^5R^6$, $NR^5C(O)OR^6$, F, Cl, Br, I, CN, 4-fluorophenyl, 4-chlorophenyl, and 4-methoxyphenyl, wherein $R^2$, $R^3$, and $R^4$ are positioned independently in any of the free positions of the mono- or bicyclic aromatic or heteroaromatic ring system;

$R^5$ and $R^6$ are independently selected from hydrogen, $C_1$-$C_{15}$ alkyl, $C_3$-$C_5$ cycloalkyl, phenyl, and $C_1$-$C_3$ haloalkyl;

$R^7$, $R^8$, $R^9$, and $R^{10}$ are independently selected from hydrogen, methyl, ethyl, n-propyl, iso-propyl, and n-butyl; or being selected such that $R^8$ and $R^9$ are connected to form a 4-, 5-, 6-, or 7-membered ring;

X is selected from hydrogen, methyl, ethyl, n-propyl, iso-propyl, n-butyl, iso-butyl, neo-butyl, tert-butyl, cyclopropyl, cyclopentyl, $CF_3$, $CF_2CF_3$, phenyl, benzyl, hydroxy, methoxy, ethoxy, 2-phenylethyl and benzyloxy, wherein said phenyl, 2-phenylethyl and benzyl groups are optionally mono- or di-substituted by substituents independently selected from methyl, ethyl, methoxy, ethoxy, iso-propyloxy, F, and Cl; and pharmaceutically acceptable salts, prodrugs, tautomers, and stereoisomers thereof.

In one embodiment of this aspect, there is provided a compound of Formula I, wherein

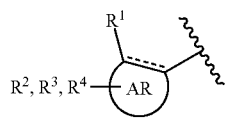

represents

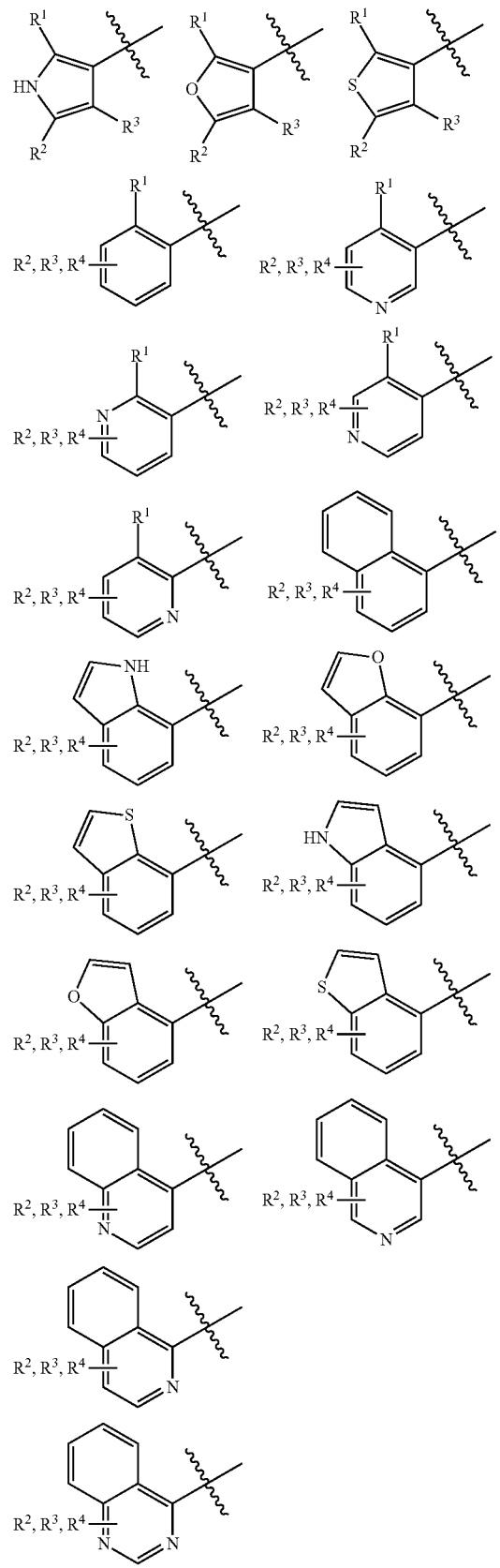

-continued

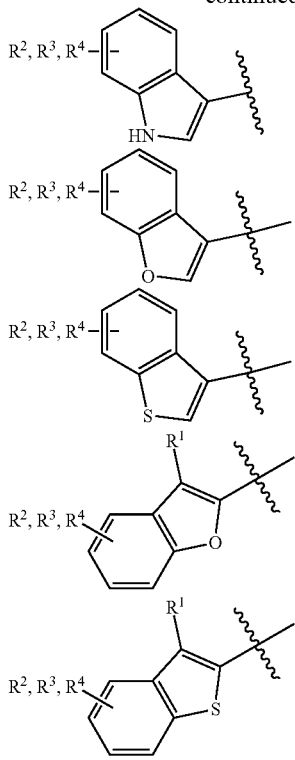

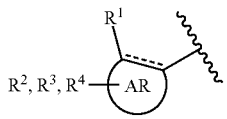

is selected from the group

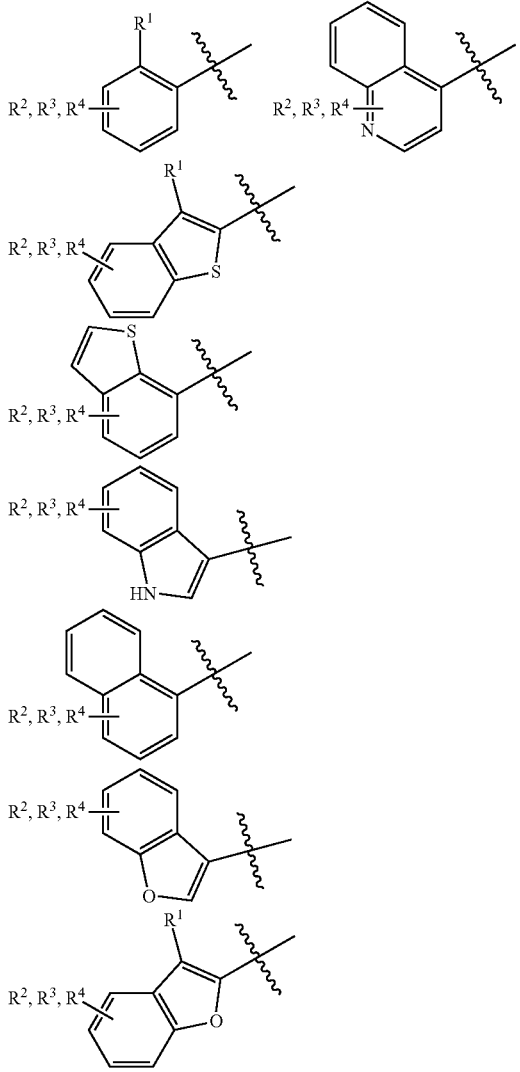

wherein

R², R³, and R⁴ are positioned independently in any of the free positions of the mono- or bicyclic aromatic or heteroaromatic ring system;

R¹ is selected from methyl, ethyl, iso-propyl, cyclopropyl, $CF_3$, hydroxy, methoxy, ethoxy, iso-propoxy, $OCF_3$, $SCH_3$, $S(O)_2CH_3$, $OC(O)OR^5$, $OC(O)R^5$, $NH_2$, $NHCH_3$, $N(CH_3)_2$, $NHC(O)H$, $NHC(O)CH_3$, $NHC(O)NH_2$, $NHC(O)NHCH_3$, $NHC(O)N(CH_3)_2$, $C(O)CH_3$, $C(O)N(CH_3)_2$, F, Cl, Br, I, CN, and phenyl;

R², R³, and R⁴ are independently selected from hydrogen, methyl, ethyl, iso-propyl, cyclopropyl, $CF_3$, hydroxy, methoxy, ethoxy, iso-propoxy, $OCF_3$, $SCH_3$, $S(O)_2CH_3$, $NH_2$, $NHCH_3$, $N(CH_3)_2$, $NHC(O)H$, $NHC(O)CH_3$, $NHC(O)NH_2$, $NHC(O)NHCH_3$, $NHC(O)N(CH_3)_2$, $C(O)CH_3$, $C(O)N(CH_3)_2$, F, Cl, Br, I, CN, and phenyl;

R⁵ represents $C_1$-$C_{15}$ alkyl or phenyl;

R⁷, R⁸, R⁹, and R¹⁰ are independently selected from hydrogen, methyl and ethyl; or being selected such that R⁸ and R⁹ are connected to form a 5-, or 6-membered ring; and X is selected from hydrogen, methyl, ethyl, n-propyl, iso-propyl, cyclopropyl, cyclopentyl, $CF_3$, $CF_2CF_3$, phenyl, 2-phenylethyl, benzyl, and hydroxy; wherein said phenyl, 2-phenylethyl, and benzyl is optionally mono- or di-substituted by substituents independently selected from methyl, ethyl, methoxy, F, and Cl.

In one embodiment of this aspect, there is provided a compound of Formula I, wherein AR is selected from phenyl, naphtyl, benzothiophenyl, quinolinyl, indolyl and benzofuranyl.

In one embodiment of this aspect, there is provided a compound of Formula I, wherein wherein R¹ is selected from methyl, iso-propyl, $CF_3$, hydroxy, methoxy, $NH_2$, F, Cl, and Br;

R², R³, and R⁴ are independently selected from hydrogen, $CF_3$, hydroxy, methoxy, F, and Cl;

R⁷, R⁸, R⁹, and R¹⁰ are independently selected from hydrogen, methyl and ethyl; or being selected such that R⁸ and R⁹ are connected to form a 5-membered ring;

X is selected from hydrogen, methyl, benzyl, $CHCH_3C_6H_5$, 4-chlorobenzyl, 2-chlorobenzyl, 2,4-dichlorobenzyl, 3,4-dichlorobenzyl, 4-methoxybenzyl, 3,5-dimethoxybenzyl, 3,4-dimethoxybenzyl, 3-chloro-4-methoxybenzyl, 2-phenylethyl, and hydroxy.

In one embodiment of this aspect, there is provided a compound of Formula I, wherein

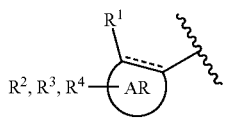

is selected from the group

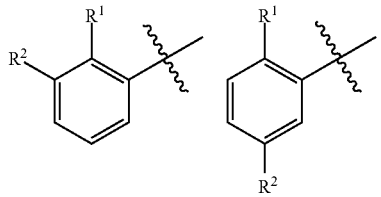

wherein
R¹ is selected from methyl, iso-propyl, CF$_3$, hydroxy, methoxy, NH$_2$, F, Cl, and Br;
R² is selected from hydrogen, CF$_3$, hydroxy, methoxy, F, and Cl.

In one embodiment of this aspect, there is provided a compound of Formula I, wherein

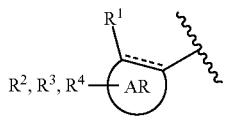

is selected from the group

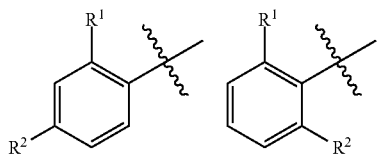

wherein
R¹ is selected from methyl, iso-propyl, CF$_3$, hydroxy, methoxy, NH$_2$, F, Cl, and Br; and
R² is selected from hydrogen and F.

In one embodiment of this aspect, there is provided a compound of Formula I, wherein

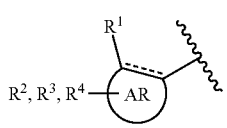

is selected from the group

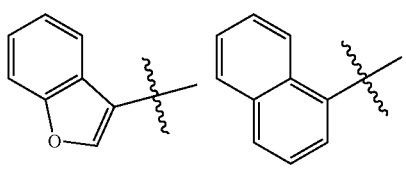

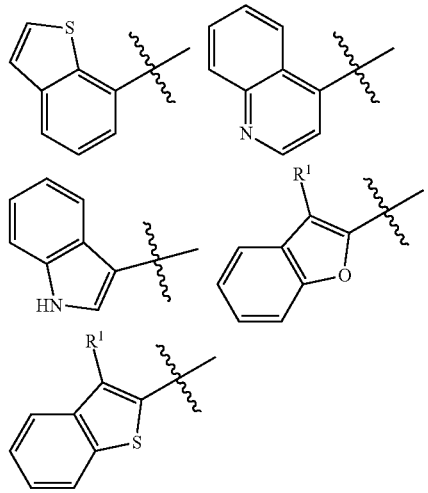

wherein
R¹ is selected from methyl, iso-propyl, CF$_3$, hydroxy, methoxy, NH$_2$, F, Cl, and Br.

In one embodiment of this aspect, there is provided a compound of Formula I, wherein

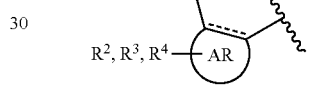

represents

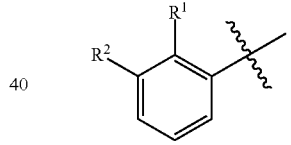

wherein R¹ is selected from methyl, iso-propyl, CF$_3$, hydroxy, methoxy, NH$_2$, F, Cl, Br, OC(O)CH$_3$, OC(O)Ph, OC(O) (CH$_2$)$_{14}$CH$_2$, OC(O)CH(CH$_3$)$_2$ and OC(O) OCH$_2$CH$_3$; and
R² is selected from hydrogen, F, Cl and Br.

In another aspect of the invention there is provided a compound of formula I for use as a medicament.

In another aspect of the invention there is provided a compound of formula I, for use in treatment of fibrosis, cardiovascular diseases, pain, IBD, or other inflammatory diseases. Typically, fibrosis is selected from systemic sclerosis, skin fibrosis, liver fibrosis, heart fibrosis, kidney fibrosis, intestinal fibrosis, lung fibrosis including idiopathic pulmonary fibrosis (IPF) and fibrosis associated with pulmonary arterial hypertension (PAH), and fibrosis associated with transplantation, surgery, stenosis, or keloid scarring. Typically, said cardiovascular disease is selected from atherosclerosis and hypertension. Typically, said pain is selected from migraine and pain associated with inflammatory diseases. Typically, said IBD is selected from Crohn's disease and ulcerous colitis.

In another aspect of the invention there is provided a compound of formula I, for use in treatment of inflammatory joint diseases including RA and OA.

In another aspect of the invention there is provided use of a compound of formula I, in the manufacture of a medicament useful in treatment of fibrosis, cardiovascular diseases, pain, IBD or other inflammatory diseases. Typically, said fibrosis is selected from systemic sclerosis, skin fibrosis, liver fibrosis, heart fibrosis, kidney fibrosis, intestinal fibrosis, lung fibrosis including idiopathic pulmonary fibrosis (IPF) and fibrosis associated with pulmonary arterial hypertension (PAH), and fibrosis associated with transplantation, surgery, stenosis, or keloid scarring. Typically, said cardiovascular disease is selected from atherosclerosis and hypertension. Typically, said pain is selected from migraine and pain associated with inflammatory diseases. Typically, said IBD is selected from Crohn's disease and ulcerous colitis.

In another aspect of the invention there is provided use of a compound of formula I, in the manufacture of a medicament useful in treatment of inflammatory joint diseases including RA and OA.

In another aspect of the invention there is provided a method of treating fibrosis, cardiovascular diseases, pain, IBD, or other inflammatory diseases comprising administering a therapeutically effective amount of a compound of Formula I to a patient in need thereof. Typically, said fibrosis is selected from systemic sclerosis, skin fibrosis, liver fibrosis, heart fibrosis, kidney fibrosis, intestinal fibrosis, lung fibrosis including idiopathic pulmonary fibrosis (IPF) and fibrosis associated with pulmonary arterial hypertension (PAH), and fibrosis associated with transplantation, surgery, stenosis, or keloid scarring. Typically, said cardiovascular diseases are selected from atherosclerosis and hypertension. Typically, said pain is selected from migraine and pain associated with inflammatory diseases. Typically, said IBD is selected from Crohn's disease and ulcerous colitis.

In another aspect of the invention there is provided a method of treating inflammatory joint diseases including RA and OA, comprising administering a therapeutically effective amount of a compound of formula I to a patient in need thereof.

In another aspect of the invention there is provided a pharmaceutical composition comprising a compound according to Formula I, admixed with one or more pharmaceutically acceptable excipients or carriers. Typically, said excipients are selected from the group comprising filling agents, lubricants, flavours, colourings, sweetenings, buffers, acidifying agents, diluents, and preservatives. Typically, said compositions are administered orally, by oral inhalation, intramuscularly, intravenously, intraperitoneally, or subcutaneously, via implants, rectally, intranasally, or transdermally; preferably orally.

The compounds of the invention may be used in the prophylaxis and treatment as such, or preferably in a form of a pharmaceutical composition. While it is possible for the active ingredient to be administered alone, it is preferable for it to be present in a pharmaceutical formulation or composition. Accordingly, the invention provides a pharmaceutical formulation comprising a compound according to the invention, and a pharmaceutically acceptable diluent, excipient or carrier (collectively referred to herein as "carrier" materials). Pharmaceutical compositions of the invention may take the form of a pharmaceutical formulation as described below. Thus, the present invention relates to a pharmaceutical composition containing at least one compound of formula I together with conventional excipients.

Exemplary compositions for oral administration include suspensions (including nanosuspensions) which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose, and/or lactose and/or other excipients, binders, extenders, disintegrants, diluents, and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes, and the like. Disintegrators include without limitation starch, methylcellulose, agar, bentonite, xanthan gum, and the like. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose, and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g. Gantrez), and agents to control release such as polyacrylic copolymer (e.g. Carbopol 934). Lubricants, glidants, flavors, coloring agents, and stabilizers may also be added for ease of fabrication and use. Lubricants used in these dosage forms include sodium oleate, sodium stearate, magnesium stearate, sodium benzoate, sodium acetate, sodium chloride, and the like. For oral administration in liquid form, the oral drug components can be combined with any oral, non-toxic, pharmaceutically acceptable inert carrier such as ethanol, glycerol, water, and the like.

The pharmaceutical formulations according to the invention include those suitable for oral, parenteral [including subcutaneous, intradermal, intramuscular, intravenous (bolus or infusion), and intraarticular], inhalation (including fine particle dusts or mists which may be generated by means of various types of metered dose pressurized aerosols), nebulizers or insufflators, rectal, intraperitoneal, and topical (including dermal, buccal, sublingual, and intraocular) administration, although the most suitable route may depend upon, for example, the condition and disorder of the recipient.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions (including nanosuspensions) or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally. Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

The compounds of the present invention can also be administered in the form of liposome delivery systems, such as small unilamellar vesicles, large unilamellar vesicles, and multilamellar vesicles. Liposomes can be formed from a variety of phospholipids, 1,2-dipalmitoylphosphatidylcholine, phosphatidyl ethanolamine (cephaline), phosphatidylserine, phosphatidylinositol, diphosphatidylglycerol (cardiolipin) or phosphatidylcholine (lecithin).

Formulations for parenteral administration include aqueous and non-aqueous sterile injection solutions which may contain anti-oxidants, buffers, bacteriostats, and solutes which render the formulation isotonic with the blood of the intended recipient; and aqueous and non-aqueous sterile suspensions (including nanosuspensions) which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules, and tablets of the kind previously described. Exemplary compositions for parenteral administration include injectable solutions or suspensions which can contain, for example, suitable non-toxic, parenterally acceptable diluents or solvents, such as polyethylene glycol, ethanol, 1,3-butanediol, water, Ringer's solution, an isotonic sodium chloride solution, or other suitable dispersing or wetting and suspending agents, including synthetic mono- or diglycerides, and fatty acids, including oleic acid, polysorbates, and Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In another aspect of the invention there is provided a pharmaceutical composition comprising a compound of general formula (I) and an additional therapeutic agent.

Compounds of general formula (I) may be administered as the sole pharmaceutical agent or in combination with one or more additional therapeutic agents where the combination causes no unacceptable adverse effects. This pharmaceutical combination includes administration of a single pharmaceutical dosage formulation which contains a compound of general formula (I) and one or more additional therapeutic agents, as well as administration of the compound of general formula (I) and each additional therapeutic agent in its own separate pharmaceutical dosage formulation. For example, a compound of general formula (I) and a therapeutic agent may be administered to the patient together in a single oral dosage composition such as a tablet or capsule, or each agent may be administered in separate dosage formulations.

Where separate dosage formulations are used, the compound of general formula (I) and one or more additional therapeutic agents may be administered at essentially the same time (e.g. concurrently) or at separately staggered times (e.g. sequentially).

In particular, the compounds of the present invention may be used in fixed or separate combination with effectors of nuclear receptors, transcription factors, G protein coupled receptors, ion channels, integrins, kinases, or enzymes.

In particular, the compounds of the present invention may be used in fixed or separate combination with: glucocorticoid receptor agonists e.g. triamcinolone, prednisone, prednisolone or budesonide; mineralocorticoid receptor antagonists e.g. spironolactone, eplerenone or canrenone; PPAR agonists e.g. rosiglitazone, GFT 505, saroglitazar, pioglitazone or farglitazar; FXR agonists e.g. obeticholic acid, Px 102 or ursodeoxycholic acid; PXR agonists e.g. pregnenolone 16α-carbonitrile; NR4A1 agonists e.g. cytosporone B; Nrf2 activators e.g. bardoxolone methyl; WNT/β-catenin inhibitors e.g. ICG-001; chemokine antagonists e.g. bindarit; LPA antagonists e.g. BMS 986020 or SAR 100842; prostacyclin analogues e.g. (+/−) beraprost sodium, iloprost or treprostinil; AT1 receptor antagonists e.g. losartan; ETA receptor antagonists e.g. atrasentan, ambrisentan, bosentan or macitentan; CCR5 antagonists e.g. maraviroc; CCR2 antagonists e.g. RS-504393; CXCR4 antagonists e.g. AMD3100; PAR1 inhibitors e.g. SCH 79797; S1P ligands e.g. fingolimod (FTY720); PTGER agonists e.g. (R)-rutaprost (prodrug); PTGFR antagonists e.g. AL-8810; LXA4 agonists e.g. BML-111; RXFP1 agonists; 5-HT2A or 5-HT2B receptor antagonists e.g. sarpogrelate; P2X7 antagonists e.g. A-438079; KCa3.1/IKCa1 blockers e.g. TRAM-34; T-type Ca2+ Channel blockers e.g. efonidipine; Na—K—Cl cotransporter inhibitors e.g. torsemide; αVβ6 integrin inhibitors e.g. CWHM 12; αVβ1 integrin inhibitors e.g. c8; Galectin 3 antagonists e.g. TD139; TGF-β or p38 inhibitors e.g. pirfenidone or F-351; tyrosine kinase inhibitors e.g. nintedanib, imatinib or nilotinib; kinase inhibitors e.g. sorafenib, dasatinib, baricitinib or tanzisertib; PI3K-mTOR inhibitors e.g. GSK2126458; MK2 inhibitors e.g. MMI 0100; IGFII antagonists e.g. PXS 64 or PXS 25; PKCδ inhibitors e.g. rottlerin; p38 MAPK inhibitors e.g. SB239063 or FR-167653; RHO kinase inhibitors e.g. Y-27632; FAK inhibitors e.g. PF-562271; ALK5 inhibitors e.g. SB-431542; SMAD3 inhibitors e.g. SIS-3; TGFβ1 inhibiting peptides e.g. disitertide; PDE inhibitors e.g. pentoxifylline or CTP 499; PDE5 inhibitors e.g. sildenafil; NADPH oxidase inhibitors e.g. GKT 137831; TAFI inhibitors e.g. UK 396,082; cathepsin B inhibitors e.g. VBY 376; caspase inhibitors e.g. emricasan; LOXL2 inhibitors e.g. β-aminopropionitrile; TGM2 antagonists e.g. NTU281; prolyl hydroxylase inhibitors e.g. HOE 077 or pyridine-2,4-dicarboxylate; inhibitors of BMP1 or BMP1-like proteinases e.g. UK-421045; neutrophil elastases e.g. ONO-5046; EPRS inhibitors e.g. halofuginone; TNKS1 inhibitors e.g. XAV939; ACE inhibitors e.g. enalapril; ATX inhibitors e.g. GWJ-A-23; AT1 receptor antagonists e.g. losartan; 5LO inhibitors e.g. zileuton; HMG-CoA reductase inhibitors (statins) e.g. atorvastatin, fluvastatin, lovastatin, pitavastatin, pravastatin, rosuvastatin or simvastatin; PAI1 antagonists e.g. TM5275; FKBP12 binders e.g. sirolimus; S100A9 binders e.g. paquinimod; methyl transfer cofactor e.g. ademetionine; immunomodulatory compounds e.g. thalidomide or pomalidomide; mitochondria-targeted antioxidants e.g. mitoquinone; vitamin derivatives e.g. pyridoxamine or α-tocopherol; purine antagonists e.g. azathioprine; ROS scavengers or anti-oxidants e.g. N-acetylcysteine, alpha lipoic acid or α-tocopherol; microtubules disrupters e.g. colchicine; copper chelators e.g. D-penicillamine; alkylators e.g. cyclophosphamide; HSP47 expression inhibitors or BET inhibitors e.g. (+) JQ-1; or interferon γ-1b.

The present invention will now be described in more detail by the following examples, which are included in order to disclose certain embodiments of the invention, but not in any way to limit the scope of the invention.

Preparation of Compounds of the Invention

The novel compounds of the present invention can be prepared by known methods described in organic chemistry textbooks (e.g. March's Advanced Organic Chemistry: Reactions, Mechanisms, and Structure, 7th Edition, Wiley) or in the literature (see e.g. WO2006/072351 and Du, X. et al. J. Med. Chem. 2002, 45, 2695-2707). Thus, the 2-pyrazoline ring can be formed by reacting aromatic Mannich bases with hydrazine to give 3-Ar-2-pyrazolines (b), with hydrazine derivatives such as aminoguanidines, $H_2NNHC(NH)NHX$ (X=H, alkyl, benzyl, phenyl, or OH) to give 1-amidino-3-Ar-2-pyrazolines (d), or with semicarbazides, $H_2NNHC(S)NHX$, to give the corresponding thiocarbonyl derivatives (c), which can be transformed to the final products (d) (Scheme 2). The ring-forming condensation reactions using hydrazine or hydrazine derivatives are typically performed in polar solvents at elevated temperatures, e.g. in alcohols such as MeOH or EtOH at reflux temperatures.

The 3-Ar-2-pyrazolines (b) can be further reacted in one or several steps with reagents that provide the amidino-group to give the 1-amidino-3-aryl-2-pyrazolines (d). Methods described in the literature are e.g. reactions with MeSC(NH)NHX, or its salts, at elevated temperature in pyridine or with amidino-pyrazole or with di-Boc-protected amidino-pyrazole in THF at room temperature followed by deprotection by TFA (Bernatowicz, M. S. et al. Tetrahedron Letters, Vol. 34, No. 21, 3389-3392, 1993). In other methods the thiocarbonyl derivatives (c) are first generated by reaction with e.g. iso-thiocyanates, XN=C=S, protected iso-thiocyanate (e.g. BzNCS, cleaved by basic hydrolysis), or other forms of activated thiocarbonyl derivatives, e.g. imidazolyl-based reagents. This is followed by activation by S-methylation, e.g. using MeI, and reaction with an amine ($H_2N$—X) to give the final 1-amidino-3-aryl-2-pyrazolines (d). See also Scheme 5 for the analogous preparation of the hydrazine starting materials.

In reaction sequences where "—NHX" is included in both the substrate and the reagent, at least one "—NHX" is —NH$_2$.

Scheme 2

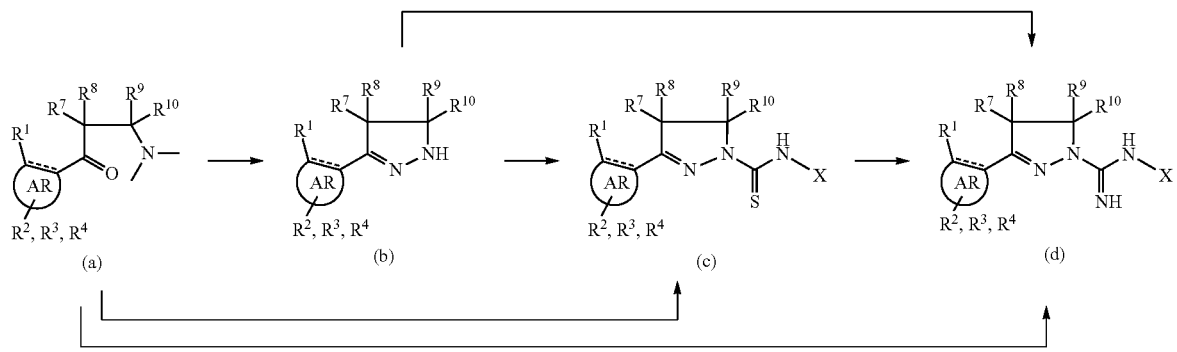

Alternatively, aryl-vinylketones (e) can be used as starting materials in the reactions with the hydrazine derivatives (Scheme 3).

Scheme 3

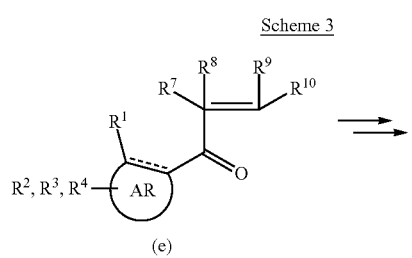

This allows for a broader range of the pyrazoline ring substitution pattern for the R9 and R10 substituents.

Another method (WO2013/006308A2), suitable for 4,4-R7,R8-disubstituted 1-amidino-3-Ar-2-pyrazolines (k) is to react aryl-allylketones containing a leaving-group (LG) in the β-position other than amino groups, such as halo or tosylate, with hydrazine or hydrazine derivatives analogous to the reactions above (Scheme 4).

Scheme 4

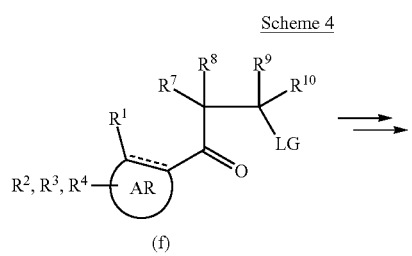

-continued

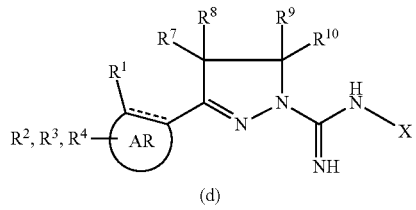

The hydrazine derivatives H$_2$NNHC(NH)NHX and H$_2$NNHC(S)NHX (X is as defined in general formula I) are either commercially available or can be prepared by known methods, see e.g. U.S. Pat. No. 4,107,326. Thus, thiosemicarbazides, which can be prepared by reacting hydrazine with iso-thiocyanates, XN=C=S, can be activated by S-methylation and further reacted with amines (XNH$_2$) or ammonia to give the aminoguanidine derivatives H$_2$NNHC(NH)NHX (Scheme 5). In these reactions the three N-groups (H$_2$NNH—, —NHX, and =NH) are interchangeable, e.g. hydrazine can be reacted with an S-methylated urea derivative MeSC(NH)NHX.

Scheme 5

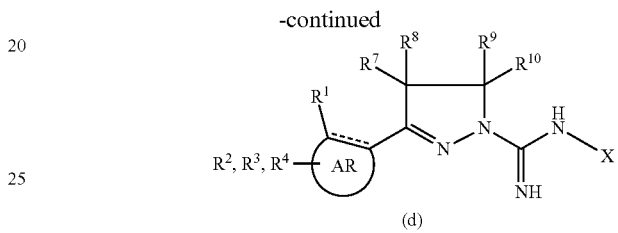

The aromatic starting materials used in the reaction with hydrazine derivatives are either commercially available or can be prepared by several methods described in the literature. The aromatic Mannich-bases (a) can be prepared from alkyl-arylketones in Mannich-type reactions using formaldehyde or an equivalent reagent, such as 1,3-dioxolane, and a dialkylamine or its salt, e.g. dimethylammonium iodide, or alternatively using a preformed iminium species, such as the Eschenmoser salt H$_2$CNMe$_2$I.

Several synthetic routes, which can be found in organic chemistry textbooks (e.g. March's Advanced Organic Chemistry: Reactions, Mechanisms, and Structure, 7th Edition, Wiley), exist for the preparation of aryl-vinylketones, some of which are listed below:

aldol-condensations of arylketones with aldehydes or ketones;

elimination of amine from N-alkylated Mannich-bases;

elimination reactions via other functionalized arylketones, such as bromo or seleno derivatives;

addition or substitution reactions with alkenyl or alkynyl nucleophiles to aromatic carbonyl compounds (e.g. aldehydes or Weinreb-amides) optionally followed by reduction of α,β-triple bonds and/or oxidation of benzylic alcohols;

Wittig-type reactions, eg. Wadsworth-Horner-Eommons reactions;

Friedel-Crafts acylation or Fries rearrangements;

metal-catalyzed acylations of aromatic precursors, e.g. Suzuki reaction using arylboronic acids and acyl chlorides; and, reaction of aromatic acyl derivatives with nucleophilic alkenes.

Yet another method (WO2013/006308A2) for the preparation of 3-Ar-2-pyrazolines is the metal-catalyzed coupling of a 3-halo-2-pyrazoline (h) with arylboronic acid derivatives (g) (Scheme 6).

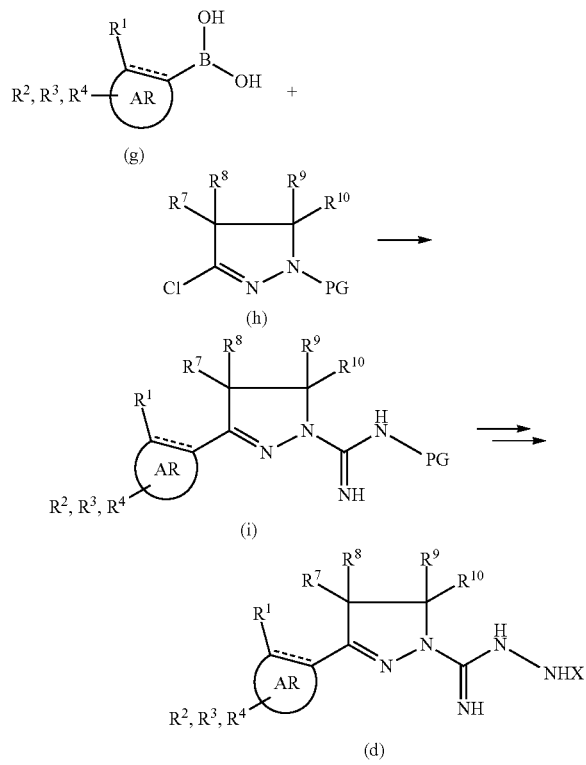

The 3-halo-2-pyrazoline can be prepared by condensation of hydrazine with acrylic starting materials to give a 3-oxo-pyrazolidine, the salt of which is chlorinated and then optionally reacted at NH with an electrophilic reagent, such as a protecting group (PG) reagent or reagents that provide the amidino-group.

In the preparative examples column chromatography separations were performed using Merck $SiO_2$ 60 (0.040-0.063 mm) silica gel. NMR spectra were recorded on Varian Mercury or on Bruker UltraShield machines (frequencies and solvents as indicated). The chemical names of the compounds were generated using Chemdraw (Cambridge-soft).

Example 1

3-(2-Methoxyphenyl)-4,5-dihydro-1H-pyrazole-1-carboximidamide Exemplified by its Hydrochloride Salt

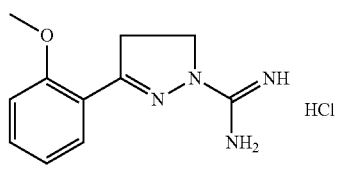 [SMILES: COc1ccccc1C1=NN(C(=N)N)CC1 ; Cl]

3-(Dimethylamino)-1-(2-methoxyphenyl)propan-1-one

Three drops (ca 70 mg) of HCl (aq. conc.) was added to a mixture of 2-hydroxy-acetophenone (1.36 g, 10.0 mmol), 1,3-dioxolane (2.96 g, 40.0 mmol), and dimethylamine hydrochloride (1.02 g, 12.5 mmol). The reaction mixture was stirred at 90° C. in a sealed vial for 3.5 h. After cooling, the reaction mixture was diluted with water (15 mL) and then washed with EtOAc (2×5 mL). The product was extracted with EtOAc (2×10 mL) after addition of aq. NaOH (2 M, 10 mL) and the organic phase was then dried ($Na_2SO_4$) and concentrated at reduced pressure to give the crude product (1.98 g, 96%), which was used without further purification in the next step.

$^1$H NMR ($CDCl_3$, 400 MHz) δ: 2.27 (s, 6H), 2.70 (t, 2H), 3.18 (t, 2H), 3.90 (s, 3H), 6.96 (d, 1H), 7.00 (t, 1H), 7.45 (t, 1H), 7.68 (d, 1H).

3-(2-Methoxyphenyl)-4,5-dihydro-1H-pyrazole-1-carboximidamide Hydrochloride

Aminoguanidine hydrochloride (111 mg, 1.00 mmol) was added to a solution of 3-(dimethylamino)-1-(2-methoxyphenyl)propan-1-one (207 mg, 1.00 mmol) in EtOH (96%, 2 mL). The reaction mixture was stirred at reflux temperature for 2 h and the solvent was then allowed to evaporate. The residue was purified by silica column chromatography (EtOAc:MeOH:AcOH, 100:0:1, 66:33:1). The eluted product was precipitated by addition of EtOAc, collected by filtration and washed with EtOAc and pentane to give the title compound as an off-white solid (60 mg, 24%).

$^1$H NMR ($CD_3OD$, 400 MHz) δ: 3.61 (t, 2H), 3.86 (s, 3H), 3.97 (t, 2H), 6.98 (t, 1H), 7.08 (d, 1H), 7.43 (t, 1H), 7.91 (d, 1H).

The following compounds in Examples 2-16 were prepared from the corresponding acetophenone derivatives by the same method as described above.

Comparative Example 2

3-Phenyl-4,5-dihydro-1H-pyrazole-1-carboximidamide Exemplified by its Hydrochloride Salt

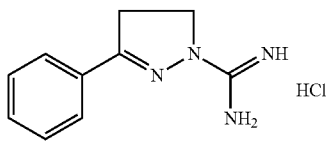 [SMILES: N=C(N)N1CCC(c2ccccc2)=N1 ; Cl]

$^1$H NMR (CD$_3$OD, 400 MHz) δ: 3.58 (t, 2H), 4.08 (t, 2H), 7.44-7.53 (m, 3H), 7.88 (d, 2H).

Example 3

3-(2-Hydroxyphenyl)-4,5-dihydro-1H-pyrazole-1-carboximidamide Exemplified by its Hydrochloride Salt

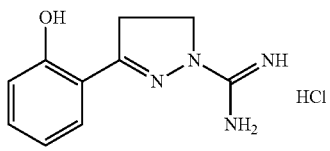 [SMILES: N=C(N)N1CCC(c2ccccc2O)=N1 ; Cl]

$^1$H NMR (CD$_3$OD, 400 MHz) δ: 3.68 (t, 2H), 4.02 (t, 2H), 6.94-7.00 (m, 2H), 7.38 (t, 1H), 7.59 (d, 1H).

Example 4

3-(2-Bromophenyl)-4,5-dihydro-1H-pyrazole-1-carboximidamide Exemplified by its 2,2,2-trifluoro-acetate Salt

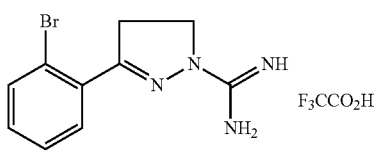

Isolated as TFA-salt after purification by HPLC (C$_{18}$/MeCN/H$_2$O/1% TFA).
$^1$H NMR ((CD$_3$)$_2$SO, 400 MHz) δ: 3.60 (t, 2H), 4.04 (t, 2H), 7.43 (t, 1H), 7.51 (t, 1H), 7.73-7.79 (m, 6H).

Example 5

3-(2-Chlorophenyl)-4,5-dihydro-1H-pyrazole-1-carboximidamide Exemplified by its 2,2,2-trifluoro-acetate Salt

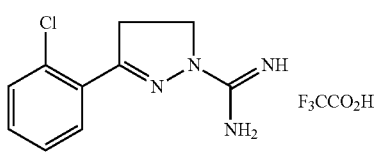

Isolated as TFA-salt after purification by HPLC (C$_{18}$/MeCN/H$_2$O/1% TFA).
$^1$H NMR ((CD$_3$)$_2$SO, 400 MHz) δ: 3.61 (t, 2H), 4.04 (t, 2H), 7.46 (t, 1H), 7.52 (t, 1H), 7.59 (d, 1H), 7.85 (s, 4H), 7.88 (d, 1H).

Example 6

3-(2-Methylphenyl)-4,5-dihydro-1H-pyrazole-1-carboximidamide Exemplified by its 2,2,2-trifluoro-acetate Salt

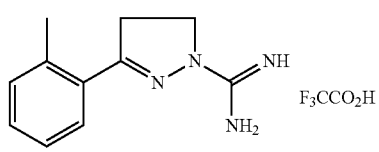

Isolated as TFA-salt after purification by HPLC (C$_{18}$/MeCN/H$_2$O/1% TFA).
$^1$H NMR ((CD$_3$)$_2$SO, 400 MHz) δ: 2.56 (s, 3H), 3.54 (t, 2H), 3.96 (t, 2H), 7.31-7.39 (m, 3H), 7.57 (d, 1H), 7.78 (s, 4H).

Example 7

3-(2,5-Difluorophenyl)-4,5-dihydro-1H-pyrazole-1-carboximidamide Exemplified by its 2,2,2-trifluoro-acetate Salt

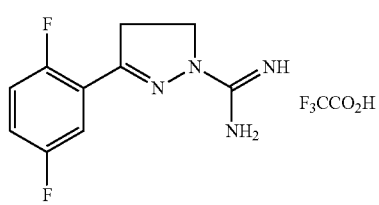

Isolated as TFA-salt after purification by HPLC (C$_{18}$/MeCN/H$_2$O/1% TFA).
$^1$H NMR ((CD$_3$)$_2$SO, 400 MHz) δ: 3.52 (t, 2H), 4.00 (t, 2H), 7.42 (t, 2H), 7.87 (s, 4H), 8.01 (m, 1H).

Example 8

3-(2-Isopropylphenyl)-4,5-dihydro-1H-pyrazole-1-carboximidamide Exemplified by its 2,2,2-trifluoro-acetate Salt

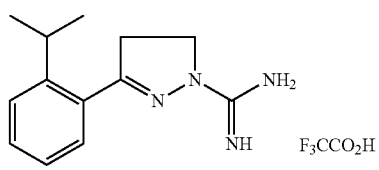

Isolated as TFA-salt after purification by HPLC (C$_{18}$/MeCN/H$_2$O/1% TFA).

$^1$H NMR ((CD$_3$)$_2$SO, 400 MHz) δ: 1.20 (d, 6H), 3.50 (t, 2H), 3.52 (m, 1H), 3.99 (t, 2H), 7.30 (t, 1H), 7.43-7.50 (m, 3H), 7.67 (s, 4H).

Example 9

3-(Naphthalen-1-yl)-4,5-dihydro-1H-pyrazole-1-carboximidamide Exemplified by its Hydrochloride Salt

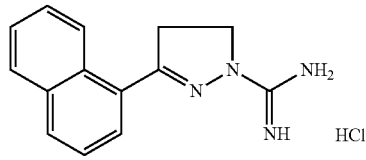 [SMILES: N=C(N)N1CCC(c2cccc3ccccc23)=N1 ; Cl]

$^1$H NMR (CD$_3$OD, 400 MHz) δ: 3.77 (t, 2H), 4.09 (t, 2H), 7.55-7.61 (m, 2H), 7.66 (t, 1H), 7.82 (d, 1H), 7.96 (d, 1H), 8.03 (d, 1H), 9.04 (d, 1H).

Example 10

3-(Benzo[b]thiophen-7-yl)-4,5-dihydro-1H-pyrazole-1-carboximidamide Exemplified by its Hydrochloride Salt

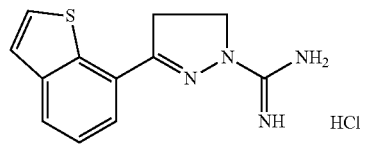 [SMILES: N=C(N)N1CCC(c2cccc3ccsc23)=N1 ; Cl]

$^1$H NMR (CD$_3$OD, 400 MHz) δ: 3.74 (t, 2H), 4.11 (t, 2H), 7.50-7.7.57 (m, 2H), 7.67-7.75 (m, 2H), 8.05 (d, 1H).

Example 11

3-(2-Fluorophenyl)-4,5-dihydro-1H-pyrazole-1-carboximidamide Exemplified by its Hydrochloride Salt

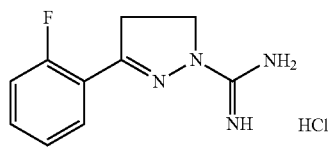 [SMILES: N=C(N)N1CCC(c2ccccc2F)=N1 ; Cl]

$^1$H NMR (CD$_3$OD, 400 MHz) δ: 3.64 (t, 2H), 4.07 (t, 2H), 7.24 (dd, 1H), 7.29 (t, 1H), 7.54 (m, 1H), 8.07 (t, 1H).

Comparative Example 12

3-(Naphthalen-2-yl)-4,5-dihydro-1H-pyrazole-1-carboximidamide Exemplified by its Hydrochloride Salt

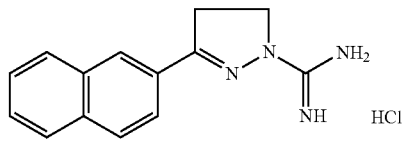 [SMILES: N=C(N)N1CCC(c2ccc3ccccc3c2)=N1 ; Cl]

$^1$H NMR (CD$_3$OD, 400 MHz) δ: 3.65 (t, 2H), 4.08 (t, 2H), 7.57 (m, 2H), 7.85-7.97 (m, 3H), 8.11 (d, 1H), 8.19 (s, 1H).

Example 13

3-(2-(Trifluoromethyl)phenyl)-4,5-dihydro-1H-pyrazole-1-carboximidamide Exemplified by its Hydrochloride Salt

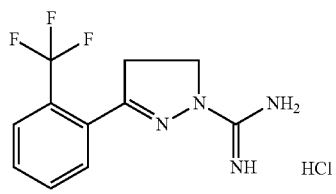 [SMILES: N=C(N)N1CCC(c2ccccc2C(F)(F)F)=N1 ; Cl]

$^1$H NMR (CD$_3$OD, 400 MHz) δ: 3.55 (t, 2H), 4.12 (t, 2H), 7.68-7.7.78 (m, 3H), 7.86 (d, 1H).

Example 14

3-(Benzofuran-3-yl)-4,5-dihydro-1H-pyrazole-1-carboximidamide Exemplified by its Hydrochloride Salt

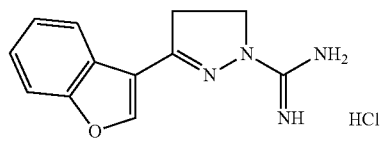 [SMILES: N=C(N)N1CCC(c2coc3ccccc23)=N1 ; Cl]

$^1$H NMR (CD$_3$OD, 400 MHz) δ: 3.59 (t, 2H), 4.05 (t, 2H), 7.41 (m, 2H), 7.58 (d, 1H), 8.32 (s, 1H), 8.33 (d, 1H).

Comparative Example 15

3-(4-Methoxyphenyl)-4,5-dihydro-1H-pyrazole-1-carboximidamide Exemplified by its 2,2,2-trifluoroacetate Salt

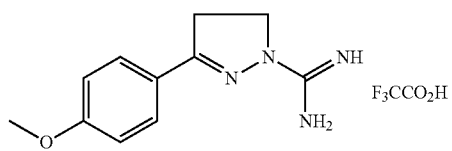

¹H NMR ((CD₃)₂SO, 400 MHz) δ: 3.46 (t, 2H), 3.83 (s, 3H), 3.97 (t, 2H), 7.05 (d, 2H), 7.66 (s, 4H), 7.81 (d, 2H).

Comparative Example 16

3-(3,4-Dimethoxyphenyl)-4,5-dihydro-1H-pyrazole-1-carboximidamide Exemplified by its 2,2,2-trifluoroacetate Salt

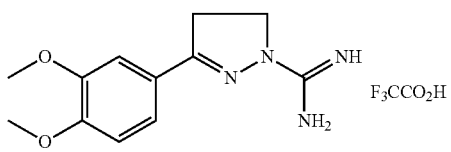

¹H NMR ((CD₃)₂SO, 400 MHz) δ: 3.46 (t, 2H), 3.82 (s, 3H), 3.82 (s, 3H), 3.98 (t, 2H), 7.05 (d, 1H), 7.29 (d, 1H), 7.55 (s, 1H), 7.71 (s, 4H).

Example 17

3-(2-Hydroxyphenyl)-4-methyl-4,5-dihydro-1H-pyrazole-1-carboximidamide Exemplified by its Hydrochloride Salt

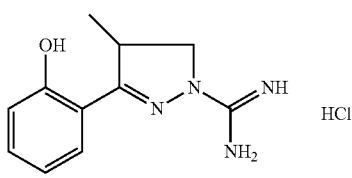 [SMILES: CC1CN(C(=N)N)N=C1c1ccccc1O ; Cl]

3-(Dimethylamino)-1-(2-hydroxyphenyl)-2-methyl-propan-1-one

Prepared by the method described in Example 1 using 1-(2-hydroxyphenyl)propan-1-one as starting material (yield 1.49 g, 77%).

¹H NMR (CDCl₃, 400 MHz) δ: 1.23 (d, 3H), 2.25 (s, 6H), 2.34 (dd, 1H), 2.85 (dd, 1H), 3.74 (m, 1H), 6.91 (t, 1H), 6.99 (d, 1H), 7.47 (t, 1H), 7.81 (d, 1H).

3-(2-Hydroxyphenyl)-4-methyl-4,5-dihydro-1H-pyrazole-1-carboximidamide Hydrochloride Prepared by the method described in Example 1. Recrystallized from MeOH-Et₂O to give 767 mg (30%) of the title compound.

¹H NMR (CD₃OD, 400 MHz) δ: 1.33 (d, 3H), 3.76 (dd, 1H), 4.11 (t, 1H), 4.23 (m, 1H), 6.96 (t, 1H), 6.98 (d, 1H), 7.36 (t, 1H), 7.65 (d, 1H).

The following compounds were prepared from the corresponding arylketone derivatives by the same method as described above.

Example 18

3-(2-Methoxyphenyl)-4-methyl-4,5-dihydro-1H-pyrazole-1-carboximidamide Exemplified by its 2,2,2-trifluoroacetate Salt

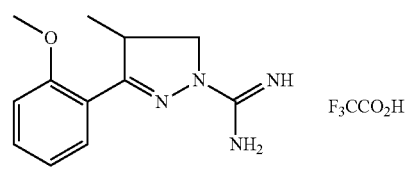

Isolated as TFA-salt after purification by HPLC (C₁₈/MeCN/H₂O/1% TFA).

¹H NMR ((CD₃)₂SO, 400 MHz) δ: 1.10 (d, 3H), 3.61 (m, 1H), 3.86 (s, 3H), 4.04-4.21 (m, 2H), 7.03 (t, 1H), 7.16 (d, 1H), 7.50 (t, 1H), 7.76 (m, 5H).

Example 19

3-(2-Chlorophenyl)-N-methyl-4,5-dihydro-1H-pyrazole-1-carboximidamide Exemplified by its Hydroiodide Salt

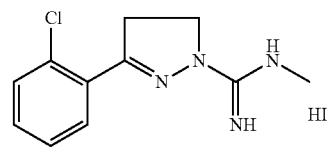

N-Methylhydrazinecarboximidamide Hydroiodide

MeI (17.03 g, 120 mmol) was added to a solution of hydrazine-carbothioamide (9.11 g, 100 mmol) in MeOH (40 mL). The reaction mixture was stirred at 60° C. for 1 h. Some of the solvent (ca 10 mL) was then evaporated to remove any residual MeI. After cooling, a solution of MeNH₂ in MeOH (15.0 mL, 9.8 M, 147 mmol) was added and the reaction mixture was stirred overnight at 60-70° C. and then concentrated at reduced pressure. The residue was crystallized from i-PrOH (40 mL), collected by filtration, washed with i-PrOH (10 mL), EtOAc (10 mL), and pentane (10 mL) to give the title compound (16.13 g, 75%) as off-white crystals.

¹H NMR (CD₃OD, 400 MHz) δ: 2.86 (s, 3H)

3-(2-Chlorophenyl)-N-methyl-4,5-dihydro-1H-pyrazole-1-carboximidamide Hydroiodide Prepared by the method described for Example 1 using N-methylhydrazinecarboximidamide hydroiodide and 1-(2-chlorophenyl)ethanone as starting materials.

¹H NMR ((CD₃)₂SO, 400 MHz) δ: 2.88 (s, 3H), 3.60 (t, 2H), 4.02 (t, 2H), 7.42-7.63 (m, 3H), 7.89 (d, 1H), 8.00 (s, 3H).

Example 20

3-(2-Hydroxyphenyl)-N-methyl-4,5-dihydro-1H-pyrazole-1-carboximidamide Exemplified by its 2,2,2-trifluoroacetate Salt

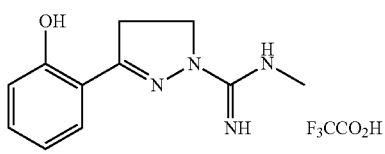

Prepared by the method described above.
$^1$H NMR ((CD$_3$)$_2$SO, 400 MHz) δ: 2.88 (d, 3H), 3.57 (t, 2H), 3.93 (t, 2H), 6.94 (t, 1H), 6.98 (d, 1H), 7.36 (t, 1H), 7.68 (d, 1H), 7.96 (s, 1H), 8.12 (s, 1H), 9.70 (s, 1H).

Example 21

N-Benzyl-3-(2-chlorophenyl)-4,5-dihydro-1H-pyrazole-1-carboximidamide

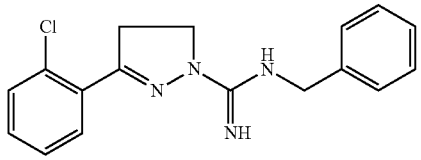 [SMILES: N=C(NCc1ccccc1)N1CCC(c2ccccc2Cl)=N1]

N-Benzylhydrazinecarboximidamide Hydroiodide

MeI (1.703 g, 12 mmol) was added to a solution of hydrazine-carbothioamide (911 mg, 10 mmol) in MeOH (10 mL). The reaction mixture was stirred in a sealed vial at 60° C. for 75 min and then in opened vial at 70° C. for 20 min. After cooling, PhCH$_2$NH$_2$ (1.07 g, 10 mmol) was added and the reaction mixture was stirred overnight at 55° C. and then concentrated at reduced pressure to give an oil. The product was crystallized by dropwise addition of Et$_2$O with vigorous stirring and was collected by filtration to give the title compound (2.848 g, 97%) as a pale orange solid.

$^1$H NMR (CD$_3$OD, 400 MHz) δ: 4.13 and 4.45 (two isomers, 1:2) (2 s, 2H), 7.28-7-48 (m, 5H).

N-Benzyl-3-(2-chlorophenyl)-4,5-dihydro-1H-pyrazole-1-carboximidamide

Prepared by the method described for Example 1 using N-benzylylhydrazinecarboximidamide hydroiodide and 1-(2-chlorophenyl)-ethanone as starting materials.

$^1$H NMR ((CD$_3$)$_2$SO, 400 MHz) δ: 3.42 (t, 2H), 4.05 (t, 2H), 4.46 (s, 2H), 7.34-7.44 (m, 8H), 7.62 (m, 1H).

Example 22

N-Benzyl-3-(2-hydroxyphenyl)-4,5-dihydro-1H-pyrazole-1-carboximidamide Exemplified by its 2,2,2-trifluoroacetate Salt

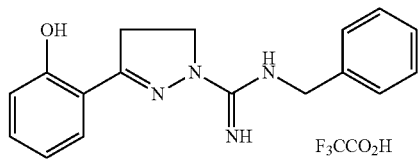

Prepared by the method described above.
$^1$H NMR ((CD$_3$)$_2$SO, 400 MHz) δ: 2.83 (t, 2H), 4.30 (t, 2H), 4.60 (d, 2H), 6.93 (d, 1H), 7.00 (t, 1H), 7.30-7.44 (m, 6H), 8.10 (s, 2H), 8.34 (d, 1H), 8.50 (s, 1H), 10.56 (s, 1H).

Example 23

5-methyl-3-(naphthalen-1-yl)-4,5-dihydro-1H-pyrazole-1-carboximidamide Exemplified by its Hydrochloride Salt

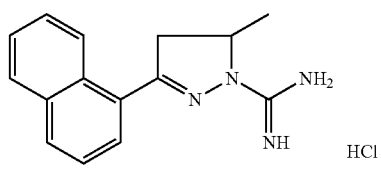 [SMILES: CC1CC(c2cccc3ccccc23)=NN1C(=N)N ; Cl]

Aq. 5 M NaOH (0.2 mL, 1 eq) was added to a solution of 1-(naphthalen-1-yl)but-2-en-1-one (196 mg, 1.0 mmol) and aminoguanidine hydrochloride 111 mg, 1.0 mmol) in 96% EtOH (2 mL). The reaction mixture was stirred at 80-90° C. for 1 h and was then cooled to room temperature, acidified with 1.5 eq HCl/EtOH (1 M, 1.5 mL), and then heated again at boiling point to reduce the volume to approx. 2 mL. The product was purified by column chromatography (SiO2, EtOAc—AcOH, 99:1, then EtOAc-MeOH—AcOH, 99:99:2) and crystallized from MeOH-EtOAc to give the title compound (175 mg, 61%).

$^1$H NMR (CD$_3$OD, 400 MHz) δ: 1.43 (d, 3H), 3.37 (dd, 1H), 4.00 (dd, 2H), 4.76 (m, 1H), 7.55-7.62 (m, 2H), 7.67 (t, 1H), 7.83 (d, 1H), 7.96 (d, 1H), 8.03 (d, 1H), 9.02 (d, 1H).

The following compounds were prepared from the corresponding α,β-unsaturated aryl-ketone derivatives by the same method as described above.

Example 24

4-Methyl-3-(naphthalen-1-yl)-4,5-dihydro-1H-pyrazole-1-carboximidamide Exemplified by its Hydrochloride Salt

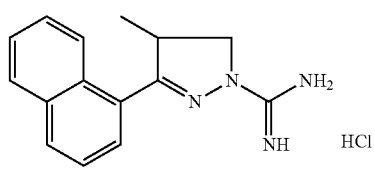 [SMILES: CC1CN(C(=N)N)N=C1c1cccc2ccccc12 ; Cl]

¹H NMR (CD₃OD, 400 MHz) δ: 1.24 (d, 3H), 3.79 (m, 1H), 4.25-4.36 (m, 2H), 7.54-7.64 (m, 3H), 7.76 (d, 1H), 7.95 (d, 1H), 8.01 (d, 1H).

Example 25

3-(2-Chlorophenyl)-5-methyl-4,5-dihydro-1H-pyrazole-1-carboximidamide Exemplified by its Hydrochloride Salt

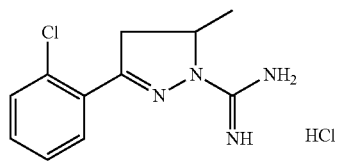 [SMILES: CC1CC(c2ccccc2Cl)=NN1C(=N)N ; Cl]

Methyl dimethylphosphonate (682 mg, 5.5 mmol) was added to a solution of LiHMDS in THF (11 mL, 1.0 M, 11.0 mmol) at 0° C. Methyl 2-chlorobenzoate (853 mg, 5.0 mmol) was then added dropwise maintaining the internal temperature of the reaction below 5° C. The reaction mixture was stirred at 0° C. for 2 h and then partitioned between NH₄Cl (aq., sat.) and EtOAc. The aqueous layer was extracted with EtOAc and the combined organic phases were dried over sodium sulfate and concentrated to get the crude dimethyl (2-(2-chlorophenyl)-2-oxoethyl)phosphonate (1.2 g), which was used in the next step without further purification.

K₂CO₃ (276 mg, 2.0 mmol) was added to a solution of the crude phosphonate (279 mg, 1.0 mmol) and acetaldehyde (88 mg, 2.0 mmol) in THF-water. The reaction mixture was stirred for 2 h and was then partitioned between diluted with Et₂O and NH₄Cl (aq., sat.). The organic layer was separated and the aqueous layer was extracted with Et₂O. The combined organic layers were dried over sodium sulfate and concentrated to get the crude 1-(2-chlorophenyl)but-2-en-1-one (150 mg), which was used in the next step without further purification. Aq. 5M NaOH (0.1 mL, 0.5 mmol) was added to a solution of the crude 1-(2-chlorophenyl)but-2-en-1-one (90 mg, 0.5 mmol) and aminoguanidine hydrochloride 55 mg, 0.5 mmol) in 96% EtOH (2 mL). The reaction mixture was stirred at 80-90° C. for 1 h and was then cooled to room temperature, acidified with 1.2 eq HCl/EtOH (1 M, 0.6 mL), and then heated again at boiling point to reduce the volume to approx. 2 mL. The product was purified by column chromatography (SiO₂, EtOAc—AcOH, 99:1, then EtOAc-MeOH—AcOH, 99:99:2) to give the title compound (27 mg, 20%).

¹H NMR ((CD₃)₂SO, 400 MHz) δ: 1.25 (d, 3H), 3.21 (d, 2H), 3.81 (dd, 1H), 4.83 (m, 1H), 7.46 (t, 1H), 7.52 (t, 1H), 7.59 (d, 1H), 7.87 (d, 1H), 7.96 (s, 4H).

The following compounds were prepared from the corresponding aromatic Me-ester derivatives by the same method as described above.

Example 26

3-(2,6-Difluorophenyl)-5-methyl-4,5-dihydro-1H-pyrazole-1-carboximidamide Exemplified by its Hydrochloride Salt

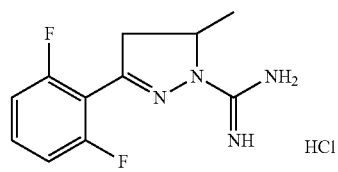 [SMILES: CC1CC(c2c(F)cccc2F)=NN1C(=N)N ; Cl]

¹H NMR (CD₃OD, 400 MHz) δ: 1.36 (d, 3H), 3.18 (d, 2H), 3.81 (dd, 1H), 4.74 (m, 1H), 7.14 (t, 2H), 7.55 (m, 1H).

Example 27

3-(2-Chlorophenyl)-5-ethyl-4,5-dihydro-1H-pyrazole-1-carboximidamide Exemplified by its Hydrochloride Salt

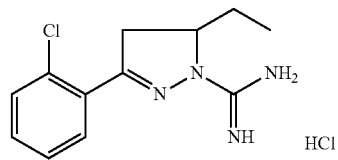 [SMILES: CCC1CC(c2ccccc2Cl)=NN1C(=N)N ; Cl]

¹H NMR (CD₃OD, 400 MHz) δ: 0.95 (t, 3H), 1.77 (m, 2H), 3.41 (d, 2H), 3.84 (dd, 1H), 4.69 (m, 1H), 7.42 (t, 1H), 7.48 (t, 1H), 7.53 (d, 1H), 7.81 (d, 1H).

Example 28

5-Methyl-3-(3-methylbenzofuran-2-yl)-4,5-dihydro-1H-pyrazole-1-carboximidamide Exemplified by its Hydrochloride Salt

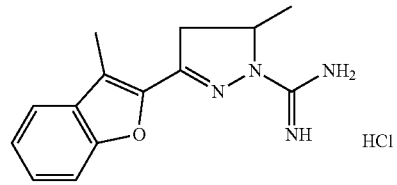 [SMILES: Cc1c(C2=NN(C(=N)N)C(C)C2)oc2ccccc12 ; Cl]

¹H NMR (CD₃OD, 400 MHz) δ: 1.39 (d, 3H), 2.59 (s, 3H), 3.33 (d, 2H), 3.82 (dd, 1H), 4.74 (m, 1H), 7.33 (t, 1H), 7.43 (t, 1H), 7.50 (d, 1H), 7.69 (d, 1H).

Example 29

5-Methyl-3-(3-methylbenzo[b]thiophen-2-yl)-4,5-dihydro-1H-pyrazole-1-carboximidamide Exemplified by its Hydrochloride Salt

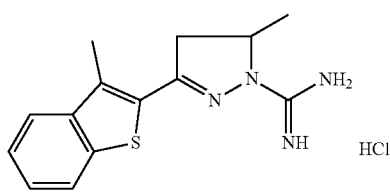

$^1$H NMR ((CD$_3$)$_2$SO, 400 MHz) δ: 1.27 (d, 3H), 2.63 (s, 3H), 3.27 (d, 1H), 3.86 (dd, 1H), 4.84 (m, 1H), 7.46 (m, 2H), 7.88-78.00 (m, 6H).

Example 30

3-(2-Chlorophenyl)-4,5,6,6a-tetrahydrocyclopenta[c]pyrazole-1(3aH)-carboximidamide Exemplified by its Hydrochloride Salt

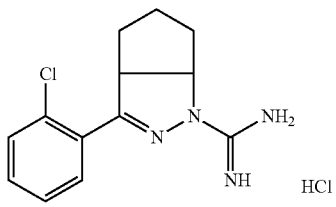 [SMILES: N=C(N)N1N=C(c2ccccc2Cl)C2CCCC21 ; Cl]

(2-Chlorophenyl)(cyclopent-1-en-1-yl)methanone

2-Chlorobenzoyl chloride 5 (8.47 g, 48.4 mmol) was added to aluminium chloride 7.10 g, 53.2 mmol) suspended in dry CH$_2$Cl$_2$ (50 mL) After 5 min the resulting complex was decanted from the excess AlCl$_3$ and cooled to 0° C. A solution of cyclopentene (3.30 g, 48.4 mmol) in dry CH$_2$Cl$_2$ (50 mL) was then added dropwise over a period of 0.5 hr. Upon completion of the addition, the mixture was added to crushed ice with vigorously stirring. After separation of the phases, the aqueous phase was extracted several times with CH$_2$Cl$_2$. The combined organic fractions were washed with NaHCO$_3$, (aq. sat.) water, and brine and dried. Removal of the solvent yielded an oil to which was immediately added triethylamine (30 mL). The resultant mixture was then heated at reflux for 48 hr. Concentration at reduced pressure yielded an oil which was diluted with ether and washed with HCl (aq., 1M), NaHCO$_3$, (aq. sat.) and brine. After drying, concentration at reduced pressure yielded crude (2-chlorophenyl)(cyclopent-1-en-1-yl)methanone (4.5 g, 45%), which was used in the next step without further purification.

3-(2-Chlorophenyl)-4,5,6,6a-tetrahydrocyclopenta[c]pyrazole-1(3aH)-carboximidamide Hydrochloride Aminoguanidine hydrochloride (0.92 g, 8.4 mmol) was added to a solution of crude (2-chlorophenyl)(cyclopent-1-en-1-yl)methanone (1.72 g, 8.4 mmol) in EtOH (95%, 20 mL) was added and then 5 M aq. NaOH (1.7 mL, 1 eq.) (NaCl precipitates). The reaction mixture was stirred at 80-90° C. (reflux) for 30-60 min, TLC (EtOAc—AcOH, 99:1, EtOAc-MeOH—AcOH, 99:99:2). The reaction mixture was cooled to room temperature and acidified with 1.1 eq. HCl/EtOH (1 M, 11 mL), and then heated again under reflux to reduce water content and volume to about 2 mL. After cooling the product was purified by column chromatography (SiO$_2$, EtOAc—AcOH, 99:1, then EtOAc-MeOH—AcOH, 99:99:2) to give the title compound (80 mg, 3.2%).

$^1$H NMR ((CD$_3$)$_2$SO, 400 MHz) δ: 1.30 (m, 1H), 1.57 (m, 1H), 1.68 (m, 1H), 1.84 (m, 1H), 1.90 (m, 2H), 4.60 (t, 1H), 4.93 (m, 1H), 7.47 (t, 1H), 7.53 (t, 1H), 7.60 (d, 1H), 7.74 (d, 1H), 7.91 (s, 4H).

Example 31

3-(2-Aminophenyl)-4,5-dihydro-1H-pyrazole-1-carboximidamide Exemplified by its Hydrochloride Salt

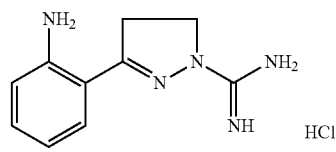 [SMILES: N=C(N)N1CCC(c2ccccc2N)=N1 ; Cl]

3-(Dimethylamino)-1-(2-nitrophenyl)propan-1-one

HCl (35% aq., 0.2 mL) was added to a solution of paraformaldehyde (1.43 g, 48 mmol), dimethylamine hydrochloride (11.64 g, 143 mmol) and 2-nitro-acetophenone (18.17 g, 110 mmol) in ethanol (10 mL). The reaction mixture was refluxed for 5 hours. The yellowish solution was diluted with cold acetone (50 mL) and chilled for several hours at 0° C. The crystals were filtrated, washed with acetone (2×20 mL), dissolved in water (20 mL), and then extracted in ethyl acetate (2×35 mL). The aqueous layer was treated with potassium carbonate (pH=10) and extracted in ethyl acetate (5×35 mL). The organic phases were dried over sodium sulfate and concentrated at reduced pressure to give the crude title compound as oil (8.7 g, 77%), which was used in the next step without further purification.

3-(2-Aminophenyl)-4,5-dihydro-1H-pyrazole-1-carboximidamide Hydrochloride

Aminoguanidine hydrochloride (0.70 g, 6.3 mmol) was added to a solution of 3-(dimethylamino)-1-(2-nitrophenyl)propan-1-one (1.40 g, 6.3 mmol) in EtOH (95%, 20 mL). NaOH (aq. 5M, 1.26 mL, 6.3 mmol) was then added (NaCl precipitates) and the reaction mixture was stirred at 80-90° C. for 60 min. After cooling to room temperature the reaction mixture was acidified with 1.1 eq HCl/EtOH (1 M, 7 mL), heated again under reflux for 0.5 hr, and then concentrated at reduced pressure. The residue was dissolved in EtOH (30 ml) and then NH$_4$Cl (1.32 g, 25.2 mmol) and iron (3.53 g, 63.0 mmol) were added. The reaction mixture was stirred at reflux for 5 h, cooled to room temperature, filtered through celite, and evaporated to dryness. The product was purified by column chromatography to give the title compound (150 mg, 10%).

¹H NMR (CD₃OD, 400 MHz) δ: 3.61 (t, 2H), 3.95 (t, 2H), 6.76 (t, 1H), 6.91 (d, 1H), 7.24 (t, 1H), 7.36 (d, 1H).

Example 32

3-(2-Hydroxyphenyl)-4,4-dimethyl-4,5-dihydro-1H-pyrazole-1-carboximidamide Exemplified by its 3,3,3-trifluoroacetate Salt

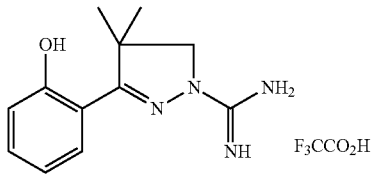

2-(4,4-Dimethyl-4,5-dihydro-1H-pyrazol-3-yl)phenol

Hydrazine hydrate (647 mg, 12.9 mmol) was added to a solution of 3-chloro-1-(2-hydroxyphenyl)-2,2-dimethylpropan-1-one (550 mg, 2.59 mmol) and NEt₃ (522 mg, 5.16 mmol) in EtOH (abs., 20 mL). The reaction mixture was stirred in a sealed vial at 130° C. for 22 h. After cooling, the reaction mixture was concentrated at reduced pressure and partitioned between water and Et₂O. The organic phase was concentrated at reduced pressure and the residue (0.52 g) was purified by silica column chromatography (heptane-EtOAc, 5:1) to give the title compound as pale yellow crystals (180 mg, 37%).

¹H NMR (CDCl₃, 400 MHz) δ: 1.50 (s, 6H), 3.30 (s, 2H), 6.86 (t, 1H), 7.01 (d, 1H), 7.23 (t, 1H), 7.54 (d, 1H).

tert-Butyl (((tert-butoxycarbonyl)imino)(3-(2-hydroxyphenyl)-4,4-dimethyl-4,5-dihydro-1H-pyrazol-1-yl)methyl)carbamate tert-Butyl (((tert-butoxycarbonyl)imino)(1H-pyrazol-1-yl)methyl)-carbamate (260 mg, 8.41 mmol) was added to a solution of 2-(4,4-dimethyl-4,5-dihydro-1H-pyrazol-3-yl)phenol (160 mg, 8.41 mmol) in THF (1.2 mL). The reaction mixture was stirred overnight and then concentrated at reduced pressure. The residue was purified by silica column chromatography (heptane-EtOAc, 10:1, 5:1) to give the title compound (136 mg, 37%).

¹H NMR (CDCl₃, 400 MHz) δ: 1.52 (s, 18H), 1.57 (s, 6H), 3.94 (s, 2H), 6.88 (t, 1H), 7.02 (d, 1H), 7.30 (t, 1H), 7.58 (d, 1H), 9.92 (broad s, 1H), 10.33 (s, 1H).

3-(2-Hydroxyphenyl)-4,4-dimethyl-4,5-dihydro-1H-pyrazole-1-carboximidamide Hydrochloride Trifluoroacetic acid (1.8 mL) was added to a solution of tert-butyl (((tert-butoxycarbonyl)imino) (3-(2-hydroxyphenyl)-4,4-dimethyl-4,5-dihydro-1H-pyrazol-1-yl)methyl)carbamate (136 mg, 3.14 mmol) in CH₂Cl₂ (1.8 mL). The reaction mixture was stirred at room temperature for 2.5 h and was then concentrated at reduced pressure. The residue was triturated with Et₂O (5 mL) to crystallize the material, which was collected by filtration, washed with Et₂O and dried to give the title compound as off-white crystals (99 mg, 91%).

¹H NMR ((CD₃)₂SO, 400 MHz) δ: 1.34 (s, 6H), 3.83 (s, 2H), 6.90 (t, 1H), 6.97 (d, 1H), 7.30-7.39 (m, 2H), 7.89 (s, 4H), 9.90 (s, 1H).

Example 33

3-(2-Chloro-6-methoxyphenyl)-4,5-dihydro-1H-pyrazole-1-carboximidamide Exemplified by its Hydrochloride Salt

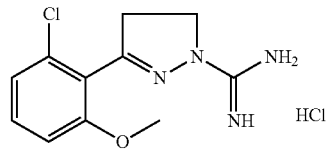 [SMILES: COc1cccc(Cl)c1C1=NN(C(=N)N)CC1 ; Cl]

1-(2-chloro-6-methoxyphenyl)-3-(dimethylamino)propan-1-one

Prepared (240 mg, 41%) by the method as described for Example 1.

¹H NMR (CDCl₃, 400 MHz) δ: 2.27 (s, 6H), 2.75 (t, 2H), 2.99 (t, 2H), 3.82 (s, 3H), 6.82 (d, 1H), 6.98 (t, 1H), 7.26 (t, 1H).

3-(2-Chloro-6-methoxyphenyl)-4,5-dihydro-1H-pyrazole

Hydrazine hydrate (0.25 mL, 5.12 mmol) was added to a solution of 1-(2-chloro-6-methoxyphenyl)-3-(dimethylamino)propan-1-one (240 mg, 8.83 mmol) in EtOH (95% 4 mL). The reaction mixture was stirred at reflux temperature for 5 h. After cooling, the reaction mixture was concentrated at reduced pressure to give the crude product as an oil (210 mg) which was used in the next step without further purification.

3-(2-Chloro-6-methoxyphenyl)-4,5-dihydro-1H-pyrazole-1-carboximidamide Hydrochloride Methyl carbamimidothioate hydroiodide (260 mg, 1.19 mmol) was added to a solution of 3-(2-chloro-6-methoxyphenyl)-4,5-dihydro-1H-pyrazole (210 mg, 1.00 mmol) in pyridine (1 mL) under argon. The reaction mixture was stirred at 110° C. for 1.5 h. After cooling, the reaction mixture was concentrated at reduced pressure and the residue was partitioned between CH₂Cl₂ and water. NaOH (aq. 1M) was added to basic reaction and the product was extracted with CH₂Cl₂. The organic phase was washed with water, dried (Na₂SO₄) and concentrated at reduced pressure. The residue (210 mg) was dissolved in EtOAc (5 mL) and HCl/MeOH (1M, 0.91 mL) was added to precipitate the product as the HCl-salt. Additional EtOAc (5 mL) was added and after stirring for 5 min the crystals were collected by filtration, washed with EtOAc and dried to give the title compound as white crystals (200 mg, 69%).

¹H NMR ((CD₃)₂SO, 400 MHz) δ: 3.34 (t, 2H), 3.83 (s, 3H), 4.07 (t, 2H), 7.16 (d, 1H), 7.18 (d, 1H), 7.49 (t, 1H), 7.87 (s, 4H).

Example 34

3-(2-Chloro-6-hydroxyphenyl)-4,5-dihydro-1H-pyrazole-1-carboximidamide Exemplified by its Hydrochloride Salt

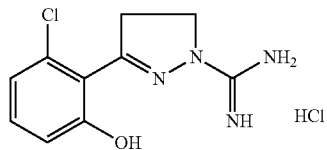 [SMILES: N=C(N)N1CCC(c2c(O)cccc2Cl)=N1 ; Cl]

A solution of 1M BBr$_3$ in MeOH (2.63 mL, 2.63 mmol) was added to a solution of 3-(2-chloro-6-methoxoxyphenyl)-4,5-dihydro-1H-pyrazole-1-carboximidamide hydrochloride (190 mg, 0.66 mmol) in CH$_2$Cl$_2$ (10 mL) under Ar. The reaction mixture was stirred at room temperature overnight. MeOH (20 mL) was added and after 10 min stirring the reaction mixture was concentrated at reduced pressure. Water (10 mL) and EtOAc (20 mL) was added to the residue and after adding KHCO$_3$ (aq., sat.) to basify the mixture, the product was extracted into the organic phase. The phases were separated and the aqueous phase was extracted with EtOAc (2×15 mL). The combined organic phases were dried (Na$_2$SO$_4$) and concentrated at reduced pressure. The residue was dissolved in MeOH (1 mL), 1M HCl in MeOH (0.5 mL) was added and the product was precipitated by addition of EtOAc (10 mL). The product was collected by filtration, washed with EtOAc and dried to give the title compound as beige crystals (95 mg, 52%).
$^1$H NMR ((CD$_3$)$_2$SO, 400 MHz) δ: 3.61 (t, 2H), 4.05 (t, 2H), 6.98 (d, 1H), 7.00 (d, 1H), 7.30 (t, 1H), 7.82 (s, 4H), 10.64 (s, 1H).

Example 35

(S)-3-(2-Hydroxyphenyl)-4-methyl-4,5-dihydro-1H-pyrazole-1-carboximidamide (Isomer 1)

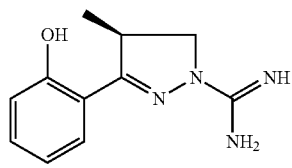 [SMILES: C[C@H]1CN(C(=N)N)N=C1c1ccccc1O]

and

Example 36

(R)-3-(2-Hydroxyphenyl)-4-methyl-4,5-dihydro-1H-pyrazole-1-carboximidamide (Isomer 2)

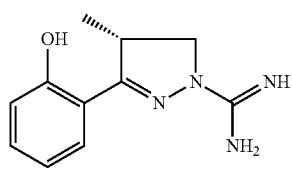 [SMILES: C[C@@H]1CN(C(=N)N)N=C1c1ccccc1O]

The enantiomers were separated and purified by SFC (Supercritical Fluid Chromatography) using an Amy-C column (20 mm×250 mm, 5 um) with MeOH/CO$_2$ (40%) as eluent (DEA was added as a modifier) with 50 mL/min flow rate and UV-detection at 280 nm wavelength.

The racemate compound HCl-salt (8.43 g) was dissolved in methanol (50 mg/mL) and injected in 0.8 mL (40 mg) volumes. The combined fractions of each enantiomer (isomer 1 at 1.22 min and isomer 2 at 1.77 min) were concentrated at reduced pressure and dried in a vacuum oven at 40° C. to give the title products as off-white crystals.

The final analysis was performed by SFC (Amy-C column, 4.6 mm×250 mm, 5 um). The eluent was MeOH/CO$_2$ (40%) (DEA was added as a modifier) with 4 mL/min flow rate.

For isomer 1:
(S)-configuration (determined by X-ray crystallography, see Ex. 37);
Yield 3.90 g (46%).
Chemical (purity 220 nm): 100%
Enantiomeric excess: 100

For isomer 2:
(R)-configuration (determined by X-ray crystallography, see Ex. 38);
Yield 3.50 g (41%).
Chemical (purity 220 nm): 100%
Enantiomeric excess: 99.8
$^1$H NMR ((CD$_3$)$_2$SO, 400 MHz) δ: 1.16 (d, 3H), 3.56 (dd, 1H), 3.89 (t, 1H), 4.14 (m, 1H), 6.14 (broad s, 4H), 6.59 (t, 1H), 6.77 (d, 1H), 7.12 (t, 1H), 7.54 (d, 1H).

Example 37

(S)-3-(2-Hydroxyphenyl)-4-methyl-4,5-dihydro-1H-pyrazole-1-carboximidamide Exemplified by its Hydrochloride Salt

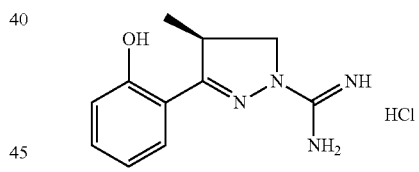

and

Example 38

(R)-3-(2-Hydroxyphenyl)-4-methyl-4,5-dihydro-1H-pyrazole-1-carboximidamide Exemplified by its Hydrochloride Salt

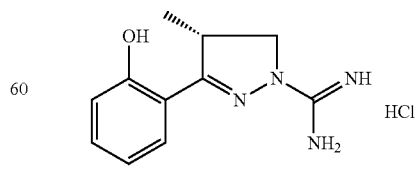

The isolated enantiomers isomer-1 and isomer-2, respectively, were dissolved in EtOH and the HCl-salts were precipitated by addition of HCL/Et$_2$O (sat.). The solvents were then removed at 40° C. under a nitrogen stream to leave the final material as off-white solid. Samples of each enantiomer were recrystallized from i-PrOH to give crystals suitable for X-ray crystallography.

Data Collection

For both isomers, plate-shaped crystals measuring approx. 0.1×0.1×0.02 mm were mounted in nylon loops using paraffin oil at room temperature. The paraffin oil was used to help the crystal to stick to the loop. Data were collected at 100 K at station 1911-3 of MAX-lab ($\lambda$=0.8 Å), equipped with a 225 mm marCCD detector. All data were integrated using the program XDS and scaled using XSCALE.

| isomer | S (isomer-1) | R (isomer-2) |
|---|---|---|
| unit cell | 7.58, 8.30, 18.86 | 7.57, 8.29, 18.86 |
| resolution (Å) | 0.75 (0.77-0.75) | 0.78 (0.81-0.78) |
| # observations, | 6820 | 5622 |
| # unique reflections, | 2694 | 2344 |
| # possible | 2944 | 2611 |
| completeness | 91.5 (60.0) | 89.8 (91.1) |
| multiplicity | 2.5 | 2.4 |
| $R_{merge}$(I) (%) | 8.4 (5.4) | 6.4 (6.5) |

The statistics take into account that Friedel pairs were not merged before refinement.

Structure Solution and Refinement

For both isomers the space group was identified as primitive orthorhombic by XDS and more specifically identified as $P2_12_12_1$ using the program XPREP (Bruker AXS). Both structures were solved using SHELXS[3] and refined using SHELXL[3] in combination with the graphical user interface SHELXLE[4]. For the S isomer (isomer-1) the R configuration of the compound together with one chloride ion was found using the atom peaks from direct methods in SHELXS. The Flack parameter from SHELXL was around 1 (0.9±0.1) after refining the R conformation, which indicates that the absolute configuration was wrong. Thus the S isomer was built instead (Flack parameter of −0.1±0.1). The final R-factor is 4.6% for 2540 Fo>4σ (Fo) and 5.0% for all 2590 reflections to 0.77 Å resolution.

For the R isomer (isomer-2) the space group $P2_12_12_1$ was given to XPREP, since this space group had been found for the previous isomer and the cell dimensions were identical. The R conformation of the compound together with one chloride ion was correctly found by SHELXS from the start. The Flack parameter from SHELXL was around 0 (−0.1±0.2) after refining the R conformation, which indicates that the absolute structure is correct. The final R-factor is 7.5% for 2268 Fo>4 σ (Fo) and 10.2% for all 2410 reflections to 0.78 Å resolution.

$^1$H NMR ((CD$_3$)$_2$SO, 400 MHz) δ: 1.18 (d, 3H), 3.70 (dd, 1H), 4.10 (t, 1H), 4.13 (m, 1H), 6.92 (t, 1H), 7.01 (d, 1H), 7.35 (t, 1H), 7.68 (d, 1H), 7.87 (s, 4H), 9.95 (s, 1H).

Example 39

3-(2-Methoxyphenyl)-N,4-dimethyl-4,5-dihydro-1H-pyrazole-1-carboximidamide Exemplified by its Hydroiodide Salt

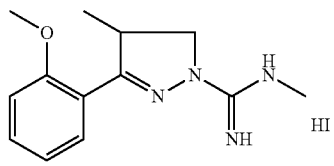

3-(Dimethylamino)-1-(2-methoxyphenyl)-2-methyl-propan-1-one

HCl (aq. conc., 0.85 mL) was added to a mixture of 1-(2-methoxyphenyl)propan-1-one (23.6 g, 144 mmol), 1,3-dioxolane (42.8 g, 578 mmol), and dimethylamine hydrochloride (14.7 g, 180 mmol). The reaction mixture was stirred at 85° C. in a sealed vial for 4 h. After cooling, the reaction mixture was mixed with EtOAc (300 mL) and stirred for 30 min to precipitate the Mannich-base as an HCl-salt. The crystals were collected by filtration, washed with EtOAc and Et$_2$O and dried to give 31 g (84%) of white crystals. The crystals were partitioned in water (250 mL) and CH$_2$Cl$_2$ (250 mL) and extracted into the organic phase after addition of NaOH (aq., 5M, 50 mL). The aqueous phase was extracted with CH$_2$Cl$_2$ (100 mL) and the combined organic phases were washed with water, dried (Na$_2$SO$_4$) and concentrated at reduced pressure to give the title compound as a pale yellow oil (23.2 g, 73%), which was used without further purification in the next step.

$^1$H NMR (CDCl$_3$, 400 MHz) δ: 1.15 (d, 3H), 2.20 (s, 6H), 2.29 (dd, 1H), 2.68 (dd, 1H), 3.67 (m, 1H), 3.88 (s, 3H), 6.94 (d, 1H), 6.98 (t, 1H), 7.42 (t, 1H), 7.55 (d, 1H).

3-(2-Methoxyphenyl)-4-methyl-4,5-dihydro-1H-pyrazole-1-carbothioamide

NaOH (aq. 50%, 1.7 mL, ca 32 mmol) was added to a solution of thiosemicarbazide (440 mg, 4.82 mmol) and 3-(dimethylamino)-1-(2-methoxyphenyl)propan-1-one (1.07 g mg, 4.82 mmol) in MeOH (60 mL) under Ar. The reaction mixture was stirred at reflux temperature for 1.5 h and was then concentrated at reduced pressure. The residue was partitioned in water and CH$_2$Cl$_2$. The organic phase was washed with water and concentrated at reduced pressure to give the crude product (1.1 g) which was purified by silica column chromatography (heptane-EtOAc, 10:4) to give the title compound as a yellow oil (940 mg, 78%).

$^1$H NMR (CDCl$_3$, 400 MHz) δ: 1.16 (d, 3H), 3.87 (s, 3H), 3.93-4.07 (m, 2H), 4.47 (t, 1H), 6.96 (d, 1H), 7.00 (t, 1H), 7.42 (t, 1H), 7.65 (d, 1H).

Methyl 3-(2-methoxyphenyl)-4-methyl-4,5-dihydro-1H-pyrazole-1-carbimidothioate Hydroiodide Methyl iodide (MeI) (1.06 g, 7.50 mmol) was added to a solution of 3-(2-methoxyphenyl)-4-methyl-4,5-dihydro-1H-pyrazole-1-carbothioamide (930 mg, 3.73 mmol) in MeOH (5 mL). The reaction mixture was stirred in a sealed vial at 70° C. for 4 h. After cooling, the solvent was evaporated at reduced pressure to give a final volume of approx. 1 mL. Et₂O (10 mL) was added and the mixture was stirred vigorously for 1 h to precipitate the product, which were collected by filtration, washed with Et₂O, and dried to give the title compound (S-methylisothiouronium derivative iodide salt) as beige crystals (1.32 g, 90%). This material was used without further purification in the next step.

3-(2-Methoxyphenyl)-N,4-dimethyl-4,5-dihydro-1H-pyrazole-1-carboximidamide Hydroiodide MeNH₂ (2.0 M in MeOH, 1.6 mL, 3.2 mmol) was added to a solution of methyl 3-(2-methoxyphenyl)-4-methyl-4,5-dihydro-1H-pyrazole-1-carbimidothioate hydroiodide (0.42 g, 1.07 mmol) in MeOH (3 mL). The reaction mixture was stirred at 70° C. in a seal vial for 3.5 h. After cooling, the reaction mixture was concentrated at reduced pressure to give the title compound (0.40 g, quant.).
¹H NMR (CDCl₃, 400 MHz) δ: 1.20 (d, 3H), 3.23 (d, 3H), 3.87 (s, 3H), 3.97 (m, 1H), 4.20 (m, 1H), 4.53 (t, 1H), 6.96 (d, 1H), 7.01 (t, 1H), 7.45 (t, 1H), 7.65 (d, 1H)).

Example 40

3-(2-Hydroxyphenyl)-N,4-dimethyl-4,5-dihydro-1H-pyrazole-1-carboximidamide

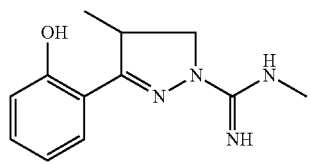 [SMILES: CNC(=N)N1CC(C)C(c2ccccc2O)=N1]

BBr₃ in CH₂Cl₂ (4.28 mL, 1M, 4.28 mmol) was added to a solution of 3-(2-methoxyphenyl)-N,4-dimethyl-4,5-dihydro-1H-pyrazole-1-carboximidamide hydroiodide (0.40 g, 1.07 mmol) in CH₂Cl₂ (10 mL). The reaction mixture was stirred at room temperature for 20 h. After addition of MeOH (50 mL) and stirring for 10 min, the solution was concentrated at reduced pressure. The residue was dissolved in water, basified with KHCO₃ (aq., sat.), and concentrated at reduced pressure. The residue was purified by silica column chromatography (CH₂Cl₂:MeOH:NH₃ (aq.), 30:5:1) to give the title compound (0.15 g, 60%).
¹H NMR ((CD₃)₂SO, 400 MHz) δ: 1.17 (d, 3H), 2.83 (s, 3H), 3.64 (dd, 1H), 3.97 (t, 1H), 4.09 (m, 1H), 6.85 (t, 1H), 6.94 (d, 1H), 7.29 (t, 1H), 7.65 (d, 1H), ca 8 (very broad s, 3H).

Example 41

N-Benzyl-3-(2-methoxyphenyl)-4-methyl-4,5-dihydro-1H-pyrazole-1-carboximidamide

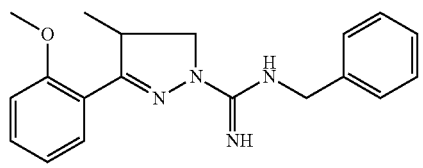 [SMILES: COc1ccccc1C1=NN(C(=N)NCc2ccccc2)CC1C]

Benzylamine (132 mg, 1.23 mmol) was added to a solution of methyl 3-(2-methoxyphenyl)-4-methyl-4,5-dihydro-1H-pyrazole-1-carbimidothioate hydroiodide (0.400 mg, 1.02 mmol) in MeOH (3 mL). The reaction mixture was stirred at reflux for 2.5 h. After cooling, the reaction mixture was partioned in NaOH (aq., 1M, 10 mL) and CH₂Cl₂ (20 mL). The organic phase was washed with water and concentrated at reduced pressure. The residue was purified by silica column chromatography (CH₂Cl₂:MeOH:NH₃ (aq.), 45:5:1) to give the title compound (235 mg, 71%).
¹H NMR (CDCl₃, 400 MHz) δ: 1.14 (d, 3H), 3.66 (dd, 1H), 3.86 (s, 3H), 3.97 (m, 1H), 4.14 (dd, 1H), 4.46 (s, 2H), 6.93 (d, 1H), 6.97 (t, 1H), 7.26 (t, 1H), 7.32-7.41 (m, 5H), 7.62 (d, 1H).

Example 42

N-Benzyl-3-(2-hydroxyphenyl)-4-methyl-4,5-dihydro-1H-pyrazole-1-carboximidamide

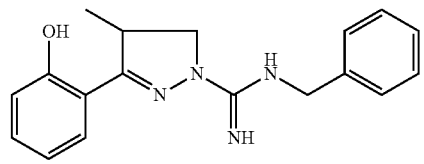 [SMILES: CC1CN(C(=N)NCc2ccccc2)N=C1c1ccccc1O]

BBr₃ in CH₂Cl₂ (2.92 mL, 1M, 2.92 mmol) was added to a solution of N-benzyl-3-(2-methoxyphenyl)-4-methyl-4,5-dihydro-1H-pyrazole-1-carboximidamide (235 mg, 1.07 mmol) in CH₂Cl₂ (10 mL). The reaction mixture was stirred at room temperature for 20 h. After addition of MeOH (30 mL) and the solution was concentrated at reduced pressure. The residue was partitioned in water (10 mL) and CH₂Cl₂ (10 mL), basified with KHCO₃ (aq., sat.) and separated. The aqueous phase was extracted with CH₂Cl₂ (10 mL) and the combined organic phases were washed with water (10 mL), dried (Na₂SO₄), and concentrated at reduced pressure. The residue was purified by silica column chromatography (CH₂Cl₂:MeOH:NH₃ (aq.), 40:5:1) to give the title compound (0.15 g, 67%).
¹H NMR (CDCl₃, 400 MHz) δ: 1.35 (d, 3H), 3.75 (m, 1H), 3.86 (dd, 1H), 3.97 (t, 1H), 4.46 (s, 2H), 6.95 (t, 1H), 7.01 (d, 1H), 7.26-7.40 (m, 7H).

Example 43

N-Hydroxy-3-(2-methoxyphenyl)-4-methyl-4,5-dihydro-1H-pyrazole-1-carboximidamide

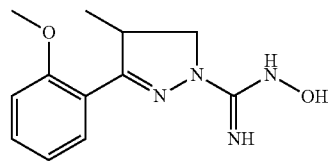 [SMILES: COc1ccccc1C1=NN(C(=N)NO)CC1C]

3-(2-Methoxyphenyl)-4-methyl-N-((tetrahydro-2H-pyran-2-yl)oxy)-4,5-dihydro-1H-pyrazole-1-carboximidamide Prepared by the method described in Example 41 using O-(tetrahydro-2H-pyran-2-yl)hydroxylamine instead of methylamine. The crude product was purified by silica column chromatography (CH$_2$Cl$_2$:MeOH, 50:1) to give the title compound (295 mg, 75%).

$^1$H NMR (CDCl$_3$, 400 MHz) δ: 1.10 (2d, 3H), 1.52-1.90 (m, 6H), 3.37-4.05 (m, 5H), 3.85 (s, 3H), 5.04 (m, 1H), 6.92 (d, 1H), 6.96 (t, 1H), 7.34 (t, 1H), 7.62 (d, 1H).

N-Hydroxy-3-(2-methoxyphenyl)-4-methyl-4,5-dihydro-1H-pyrazole-1-carboximidamide Dowex 50×8-400 (H form, 1.7 meq/mL, 250 mg) was added to a solution of 3-(2-methoxyphenyl)-4-methyl-N-((tetrahydro-2H-pyran-2-yl)oxy)-4,5-dihydro-1H-pyrazole-1-carboximidamide (295 mg, 0.89 mmol) in CH$_2$Cl$_2$ (5 mL). The reaction mixture was stirred at room temperature for 20 h. NH$_3$ in EtOH (5M, 5 mL) was added and after 15 min stirring the solution is separated by filtration and concentrated at reduced pressure. The residue was purified by silica column chromatography (CH$_2$Cl$_2$:MeOH, 10:1) to give the title compound (80 mg, 36%).

$^1$H NMR (CDCl$_3$, 400 MHz) δ: 1.12 (d, 3H), 3.45 (m, 1H), 3.86 (s, 3H), 3.87-3.98 (m, 2H), 6.93 (d, 1H), 6.98 (t, 1H), 7.36 (t, 1H), 7.64 (d, 1H).

Example 44

N-Hydroxy-3-(2-hydroxyphenyl)-4-methyl-4,5-dihydro-1H-pyrazole-1-carboximidamide Exemplified by its Hydrobromide Salt

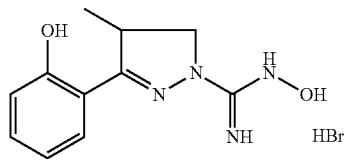 [SMILES: CC1CN(C(=N)NO)N=C1c1ccccc1O ; Br]

Prepared by the method described in Example 40. After concentrating the reaction mixture in MeOH the crude product HBr-salt was purified by silica column chromatography (EtOAc:MeOH:AcOH, 100:10:1) to give the title compound (62 mg, 61%).

$^1$H NMR ((CD$_3$)$_2$SO, 400 MHz) δ: 1.18 (d, 3H), 3.65 (dd, 1H), 4.00 (t, 1H), 4.09 (m, 1H), 6.93 (t, 1H), 6.98 (d, 1H), 7.35 (t, 1H), 7.67 (d, 1H), 8.18 (s, 2H), 9.80 (s, 1H), 10.04 (s, 1H), 11.17 (s, 1H).

Example 45

3-(5-Fluoro-2-methoxyphenyl)-4-methyl-4,5-dihydro-1H-pyrazole-1-carboximidamide

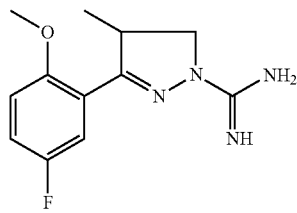 [SMILES: COc1ccc(F)cc1C1=NN(C(=N)N)CC1C]

1-(5-Fluoro-2-methoxyphenyl)propan-1-one

MeI (1.12 g, 7.88 mmol) was added to a mixture of 1-(5-fluoro-2-hydroxyphenyl)propan-1-one (1.02 g, 6.06 mmol) and K$_2$CO$_3$ (1.26 g, 9.09 mmol) in DMF (10 mL). The reaction mixture was stirred at room temperature for 20 min and was then partitioned in water (30 mL) and Et$_2$O (40 mL). The organic phase was washed with water (2×20 mL), dried (Na$_2$SO$_4$), and concentrated at reduced pressure to give the crude title compound as an oil (1.04 g, 91%).

$^1$H NMR (CDCl$_3$, 400 MHz) δ: 1.16 (t, 3H), 2.99 (q, 2H), 3.89 (s, 3H), 6.91 (dd, 1H), 7.14 (ddd, 1H), 7.41 (dd, 1H).

3-(Dimethylamino)-1-(5-fluoro-2-methoxyphenyl)-2-methylpropan-1-one

HCl (aq. conc., 0.052 mL) was added to a mixture of 1-(5-fluoro-2-methoxyphenyl)propan-1-one (1.58 g, 8.67 mmol), 1,3-dioxolane (2.58 g, 34.8 mmol), and dimethylamine hydrochloride (0.883 g, 10.8 mmol). The reaction mixture was stirred at 85° C. in a sealed vial for 4 h. After cooling, the reaction mixture was mixed with EtOAc (40 mL) and stirred for 2 h to precipitate the crude product HCl-salt, which was collected by filtration, washed with EtOAc, and dried. The solid material (1.95 g) was partitioned in water (30 mL) and CH$_2$Cl$_2$ (50 mL). The mixture was basified by addition of KHCO$_3$ (aq., sat.) and the product was extracted into the organic phase. The aqueous phase was extracted with CH$_2$Cl$_2$ (25 mL) and the combined organic phases were washed with water (30 mL), dried (Na$_2$SO$_4$), and concentrated at reduced pressure to give the title compound as an oil (1.45 g, 70%).

$^1$H NMR (CDCl$_3$, 400 MHz) δ: 1.15 (d, 3H), 2.21 (s, 6H), 2.29 (dd, 1H), 2.72 (dd, 1H), 3.69 (m, 1H), 6.90 (dd, 1H), 7.13 (ddd, 1H), 7.29 (dd, 1H).

3-(5-Fluoro-2-methoxyphenyl)-4-methyl-4,5-dihydro-1H-pyrazole-1-carboximidamide

Aminoguanidine hydrochloride (673 mg, 6.06 mmol) was added to a solution of 3-(dimethylamino)-1-(5-fluoro-2-methoxyphenyl)-2-methylpropan-1-one (1.45 g, 6.06 mmol) in EtOH (96%, 12 mL). The reaction mixture was stirred at reflux temperature for 20 h and was then concentrated to a volume of approx. 3.5 mL. EtOAc (35 mL) was added and the reaction mixture was stirred for 15 min to precipitate the crude product HCl-salt, which was collected by filtration, washed with EtOAc, and dried. The solid material (0.92 g) was dissolved in water (25 mL) and was basified by addition of KHCO$_3$ (aq., sat.) and concentrated to dryness at reduced pressure. CH$_2$Cl$_2$ (40 mL) was added to the residue and after 5 min stirring the mixture was filtered. The filtrate was concentrated at reduced pressure to give the title compound as an orange foam (0.60 g, 40%).

$^1$H NMR (CDCl$_3$, 400 MHz) δ: 1.15 (d, 3H), 3.66 (dd, 1H), 3.84 (s, 3H), 4.00 (m, 1H), 4.14 (dd, 1H), 6.86 (dd, 1H), 7.05 (ddd, 1H), 7.40 (dd, 1H).

Example 46

3-(5-Fluoro-2-hydroxyphenyl)-4-methyl-4,5-di-hydro-1H-pyrazole-1-carboximidamide Exemplified by its Hydrobromide Salt

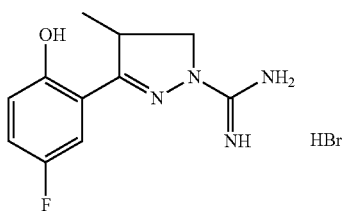 [SMILES: CC1CN(C(=N)N)N=C1c1cc(F)ccc1O ; Br]

BBr₃ in CH₂Cl₂ (4.0 mL, 1M, 4 mmol) was added to a solution of 3-(5-fluoro-2-methoxyphenyl)-4-methyl-4,5-di-hydro-1H-pyrazole-1-carboximidamide (0.25 g, 1.0 mmol) in CH₂Cl₂ (12 mL). The reaction mixture was stirred at room temperature for 20 h. After addition of MeOH (10 mL) the solution was concentrated at reduced pressure. MeOH (10 mL) was again added. The solution was concentrated at reduced pressure and the residue was recrystallized at 0° C. from MeOH (3 mL). The yellowish crystals were collected by filtration, washed with Et₂O, and dried to give the title compound (60 mg, 19%).
¹H NMR ((CD₃)₂SO, 400 MHz) δ: 1.18 (d, 3H), 3.69 (dd, 1H), 4.05-4.18 (m, 2H), 6.98 (dd, 1H), 7.21 (dt, 1H), 7.62 (dd, 1H), 7.75 (s, 4H), 10.01 (s, 1H).

Example 47

3-(3-Fluoro-2-methoxyphenyl)-4-methyl-4,5-di-hydro-1H-pyrazole-1-carboximidamide

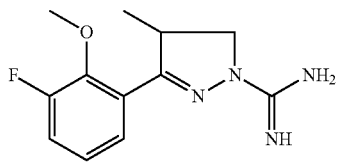 [SMILES: COc1c(F)cccc1C1=NN(C(=N)N)CC1C]

Prepared by the method described in Example 45.
Yield: 500 mg (55%).
¹H NMR (CDCl₃, 400 MHz) δ: 1.20 (d, 3H), 3.82 (dd, 1H), 3.96 (d, 3H), 4.00 (m, 1H), 4.38 (t, 1H), 6.61 (s, 3H), 7.04 (dt, 1H), 7.17 (ddd, 1H), 7.41 (d, 1H).

Example 48

3-(3-Fluoro-2-hydroxyphenyl)-4-methyl-4,5-di-hydro-1H-pyrazole-1-carboximidamide Exemplified by its Hydrobromide Salt

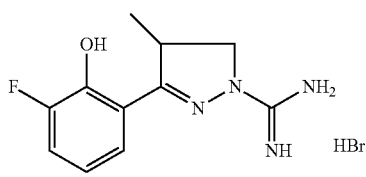 [SMILES: CC1CN(C(=N)N)N=C1c1cccc(F)c1O ; Br]

Prepared by the method described in Example 46.
Yield: 156 mg (42%).
¹H NMR ((CD₃)₂SO, 400 MHz) δ: 1.19 (d, 3H), 3.71 (dd, 1H), 4.05-4.18 (m, 2H), 6.94 (dt, 1H), 7.36 (ddd, 1H), 7.50 (d, 1H), 7.80 (s, 4H), 9.92 (s, 1H).

Example 49

3-(4-Fluoro-2-methoxyphenyl)-4-methyl-4,5-di-hydro-1H-pyrazole-1-carboximidamide

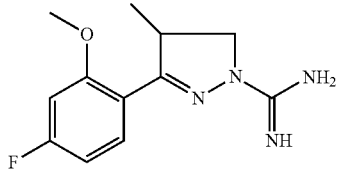 [SMILES: COc1cc(F)ccc1C1=NN(C(=N)N)CC1C]

Prepared by the method described in Example 45.
Yield: 470 mg (75%).
¹H NMR (CDCl₃, 400 MHz) δ: 1.14 (d, 3H), 3.73 (dd, 1H), 3.85 (s, 3H), 4.02 (m, 1H), 4.26 (t, 1H), 6.13 (s, 3H), 6.66 (dd, 1H), 6.70 (dt, 1H), 7.64 (dd, 1H).

Example 50

3-(4-Fluoro-2-hydroxyphenyl)-4-methyl-4,5-di-hydro-1H-pyrazole-1-carboximidamide Exemplified by its Hydrobromide Salt

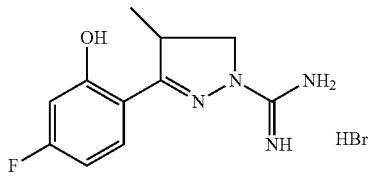 [SMILES: CC1CN(C(=N)N)N=C1c1ccc(F)cc1O ; Br]

Prepared by the method described in Example 46.
Yield: 90 mg (25%).
¹H NMR ((CD₃)₂SO, 400 MHz) δ: 1.17 (d, 3H), 3.67 (dd, 1H), 4.03-4.17 (m, 2H), 6.77-6.83 (m, 2H), 7.65-7.80 (m, 5H), 10.36 (s, 1H).

Example 51

3-(5-Chloro-2-methoxyphenyl)-4-methyl-4,5-di-hydro-1H-pyrazole-1-carboximidamide

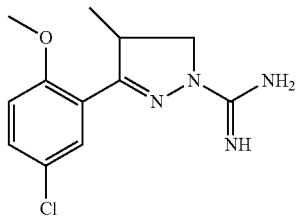 [SMILES: COc1ccc(Cl)cc1C1=NN(C(=N)N)CC1C]

Prepared by the method described in Example 45.
Yield: 520 mg (27%).
¹H NMR ((CD₃)₂SO, 400 MHz) δ: 1.05 (d, 3H), 3.51 (dd, 1H), 3.85 (s, 3H), 3.88 (m, 1H), 4.00 (t, 1H), 7.1-7.7 (broad s, 3H), 7.15 (d, 1H), 7.45 (d, 1H), 7.79 (d, 1H).

Example 52

3-(5-Chloro-2-hydroxyphenyl)-4-methyl-4,5-dihydro-1H-pyrazole-1-carboximidamide Exemplified by its Hydrobromide Salt

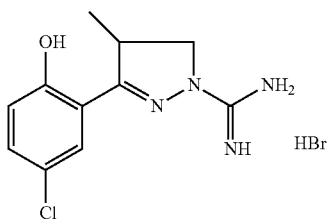 [SMILES: CC1CN(C(=N)N)N=C1c1cc(Cl)ccc1O ; Br]

Prepared by the method described in Example 46.
Yield: 90 mg (38%).
$^1$H NMR ((CD$_3$)$_2$SO, 400 MHz) δ: 1.16 (d, 3H), 3.66 (dd, 1H), 4.05-4.22 (m, 2H), 6.97 (d, 1H), 7.35 (d, 1H), 7.77 (s, 4H), 10.5 (broad s, 1H).

Example 53

3-(3-Chloro-2-methoxyphenyl)-4-methyl-4,5-dihydro-1H-pyrazole-1-carboximidamide

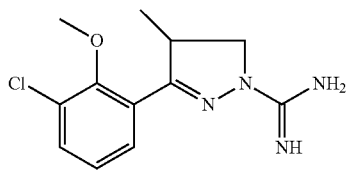 [SMILES: COc1c(Cl)cccc1C1=NN(C(=N)N)CC1C]

Prepared by the method described in Example 45.
Yield: 520 mg (54%).
$^1$H NMR (CDCl$_3$, 400 MHz) δ: 1.17 (d, 3H), 3.71 (dd, 1H), 3.82 (s, 3H), 3.92 (m, 1H), 4.24 (t, 1H), 5.25 (s, 3H), 7.10 (t, 1H), 7.44 (dd, 1H), 7.51 (dd, 1H).

Example 54

3-(3-Chloro-2-hydroxyphenyl)-4-methyl-4,5-dihydro-1H-pyrazole-1-carboximidamide Exemplified by its Hydrobromide Salt

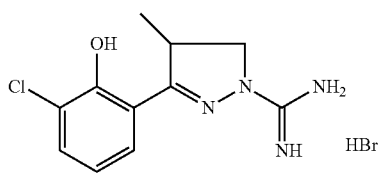 [SMILES: CC1CN(C(=N)N)N=C1c1cccc(Cl)c1O ; Br]

Prepared by the method described in Example 46.
Yield: 135 mg (36%).
$^1$H NMR ((CD$_3$)$_2$SO, 400 MHz) δ: 1.21 (d, 3H), 3.77 (dd, 1H), 4.05 (t, 1H), 4.13 (m, 1H), 7.02 (t, 1H), 7.59 (m, 2H), 7.90 (s, 4H), 9.89 (s, 1H).

Example 55

N-(4-Chlorobenzyl)-3-(2-hydroxyphenyl)-4-methyl-4,5-dihydro-1H-pyrazole-1-carboximidamide Exemplified by its Hydrochloride Salt

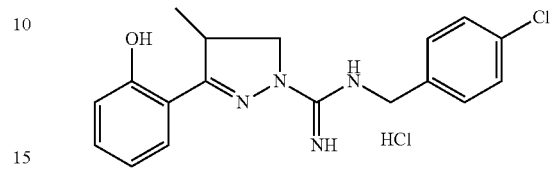

3-(2-Hydroxyphenyl)-4-methyl-4,5-dihydro-1H-pyrazole-1-carbothioamide

BBr$_3$ in CH$_2$Cl$_2$ (87 mL, 1M, 87 mmol) was added during 30 min to a solution of methyl 3-(2-methoxyphenyl)-4-methyl-4,5-dihydro-1H-pyrazole-1-carbothioamide (7.20 g, 28.9 mmol) in CH$_2$Cl$_2$ (80 mL). The reaction mixture was stirred at room temperature for 20 h. The reaction mixture was cooled to 5° C. and then MeOH (80 mL) was added during 30 min. The mixture was concentrated at reduced pressure to dryness. MeOH (100 mL) was again added and the mixture was concentrated at reduced pressure. The residue was stirred in MeOH (60 mL) for 30 min to give a suspension. The solid material was collected by filtration, washed with cold MeOH and dried to give the title compound (4.1 g, 60%).
$^1$H NMR ((CD$_3$)$_2$SO, 400 MHz) δ: 1.16 (d, 3H), 3.86-3.97 (m, 2H), 4.15 (t, 1H), 6.91 (t, 1H), 6.95 (d, 1H), 7.32 (t, 1H), 7.63 (d, 1H), 9.75 (s, 1H).

Methyl 3-(2-hydroxyphenyl)-4-methyl-4,5-dihydro-1H-pyrazole-1-carbimidothioate Hydroiodide MeI (0.724 g, 5.10 mmol) was added to a solution of 3-(2-methoxyphenyl)-4-methyl-4,5-dihydro-1H-pyrazole-1-carbothioamide (1.00 g, 4.25 mmol) in MeOH (6 mL). The reaction mixture was stirred in a sealed vial at 70° C. for 4 h and was then allowed to cool to room temperature to give a suspension. MeOH (6 mL) was added and the mixture was stirred for 10 min. The solid material was collected by filtration, washed with cold MeOH (5 mL) and dried to give the title compound (1.00 g, 64%).
$^1$H NMR ((CD$_3$)$_2$SO, 400 MHz) δ: 1.21 (d, 3H), 2.69 (s, 3H), 3.79 (dd, 1H), 4.20-4.33 (m, 2H), 6.94 (t, 1H), 6.99 (d, 1H), 7.40 (t, 1H), 7.67 (broad s, 1H), 10.22 (s, 1H).

N-(4-Chlorobenzyl)-3-(2-hydroxyphenyl)-4-methyl-4,5-dihydro-1H-pyrazole-1-carboximidamide Hydrochloride 4-Chlorobenzylamine (0.156 g, 1.10 mmol) was added to a solution of methyl 3-(2-hydroxyphenyl)-4-methyl-4,5-dihydro-1H-pyrazole-1-carbimidothioate hydroiodide (0.400 g, 1.06 mmol) in MeOH (3 mL). The reaction mixture was stirred at reflux for 2.5 h. After cooling, the reaction mixture was partitioned in CH$_2$Cl$_2$ (20 mL) and water (10 mL) and the mixture was basified by addition of KHCO₃ (aq., sat.). The organic phase was washed with water and the aqueous phase was extracted with CH₂Cl₂ (10 mL). The combined organic phases were concentrated at reduced pressure. The residue was purified by silica column chromatography (CH₂Cl₂:MeOH:NH₃ (aq.), 45:5:1) to give the base product (0.21 g, 61%) as a glass. This was dissolved in MeOH (2 mL) and HCl in MeOH (1.75 mL, 0.55 M, 1.0 mmol) was added followed by addition of EtOAc (10 mL) and Et₂O (10 mL) to precipitate the HCl-salt, which was collected by filtration, washed with Et₂O and dried to give the title compound (0.13 g, 34%).

$^1$H NMR ((CD₃)₂SO, 400 MHz) δ: 1.19 (d, 3H), 3.77 (dd, 1H), 4.10-4.21 (m, 2H), 4.59 (s, 2H), 6.91 (t, 1H), 7.02 (d, 1H), 7.34 (t, 1H), 7.44 (q$_{AB}$, 4H), 7.72 (d, 1H), 8.22 (s, 2H), 8.79 (s, 1H), 10.03 (s, 11-1).

Example 56

N-(2-Chlorobenzyl)-3-(2-hydroxyphenyl)-4-methyl-4,5-dihydro-1H-pyrazole-1-carboximidamide Exemplified by its Hydrochloride Salt

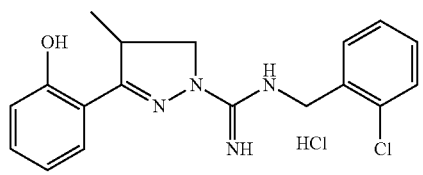 [SMILES: CC1CN(C(=N)NCc2ccccc2Cl)N=C1c1ccccc1O ; Cl]

Prepared by the method described in Example 55. The salt-formation by addition of HCl/MeOH was performed in CH₂Cl₂ followed by repeated evaporation of the solvents to dryness at reduced pressure.

Yield: 0.18 g (47%).

$^1$H NMR ((CD₃)₂SO, 400 MHz) δ: 1.21 (d, 3H), 3.81 (dd, 1H), 4.13-4.25 (m, 2H), 4.63 (d, 2H), 6.92 (t, 1H), 7.04 (d, 1H), 7.32-7.43 (m, 4H), 7.51 (d, 1H), 8.25 (s, 2H), 8.68 (t, 1H), 10.06 (s, 1H).

Example 57

N-(2,4-Dichlorobenzyl)-3-(2-hydroxyphenyl)-4-methyl-4,5-dihydro-1H-pyrazole-1-carboximidamide

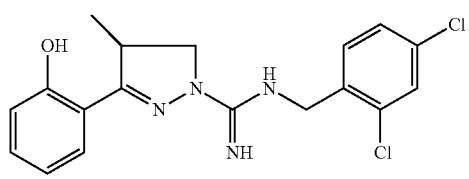 [SMILES: CC1CN(C(=N)NCc2ccc(Cl)cc2Cl)N=C1c1ccccc1O]

Prepared by the method described in Example 55 without salt-formation.

Yield: 0.183 g (49%).

$^1$H NMR (CDCl₃, 400 MHz) δ: 1.37 (d, 3H), 3.80 (m, 1H), 3.94 (dd, 1H), 4.02 (t, 1H), 4.57 (s, 2H), 6.96 (t, 1H), 7.03 (d, 1H), 7.26 (dd, 1H), 7.30-7.37 (m, 2H), 7.40 (d, 1H), 7.58 (d, 1H).

Example 58

N-(3,4-Dichlorobenzyl)-3-(2-hydroxyphenyl)-4-methyl-4,5-dihydro-1H-pyrazole-1-carboximidamide Exemplified by its Hydrochloride Salt

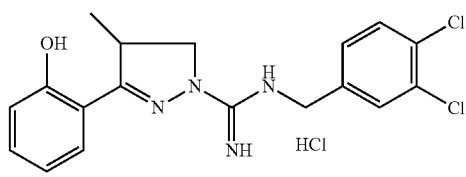 [SMILES: CC1CN(C(=N)NCc2ccc(Cl)c(Cl)c2)N=C1c1ccccc1O ; Cl]

Prepared by the method described in Example 55.
Yield: 0.17 g (41%).

$^1$H NMR ((CD₃)₂SO, 400 MHz) δ: 1.19 (d, 3H), 3.76 (m, 1H), 4.10-4.22 (m, 2H), 4.59 (s, 2H), 6.92 (t, 1H), 7.02 (d, 1H), 7.35 (t, 1H), 7.41 (d, 1H), 7.64-7.75 (m, 3H), 8.22 (s, 2H), 8.80 (s, 1H), 10.02 (s, 1H).

Example 59

3-(2-Hydroxyphenyl)-N-(4-methoxybenzyl)-4-methyl-4,5-dihydro-1H-pyrazole-1-carboximidamide Exemplified by its Hydrochloride Salt

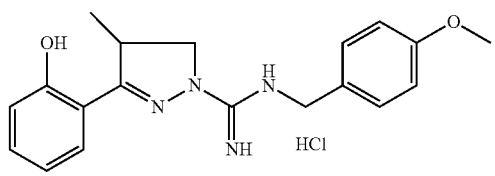 [SMILES: COc1ccc(CNC(=N)N2CC(C)C(c3ccccc3O)=N2)cc1 ; Cl]

Prepared by the method described in Example 55.
Yield: 0.11 g (29%).

$^1$H NMR (CD₃OD, 400 MHz) δ: 1.32 (d, 3H), 3.74-3.80 (m, 1H), 3.79 (s, 3H), 4.12 (t, 1H), 4.23 (m, 1H), 4.52 (s, 2H), 6.90-7.00 (m, 4H), 7.28-7.40 (m, 3H), 7.66 (d, 1H).

Example 60

N-(3,4-Dimethoxybenzyl)-3-(2-hydroxyphenyl)-4-methyl-4,5-dihydro-1H-pyrazole-1-carboximidamide Exemplified by its Hydrochloride Salt

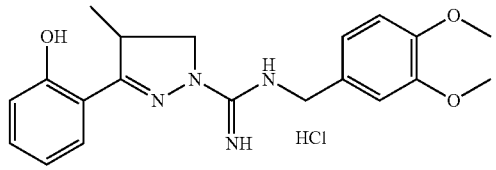 [SMILES: COc1ccc(CNC(=N)N2CC(C)C(c3ccccc3O)=N2)cc1OC ; Cl]

Prepared by the method described in Example 56.
Yield: 0.25 g (62%).

$^1$H NMR ((CD₃)₂SO, 400 MHz) δ: 1.18 (d, 3H), 3.73 (s, 3H), 3.73-3.78 (m, 1H), 3.76 (s, 3H), 4.09-4.20 (m, 2H), 4.48 (d, 2H), 6.89-6.95 (m, 3H), 7.01 (d, 1H), 7.07 (s, 1H), 7.34 (t, 1H), 7.71 (d, 1H), 8.14 (s, 2H), 8.68 (t, 1H), 9.99 (s, 1H).

Example 61

N-(3,5-Dimethoxybenzyl)-3-(2-hydroxyphenyl)-4-methyl-4,5-dihydro-1H-pyrazole-1-carboximidamide Exemplified by its Hydrochloride Salt

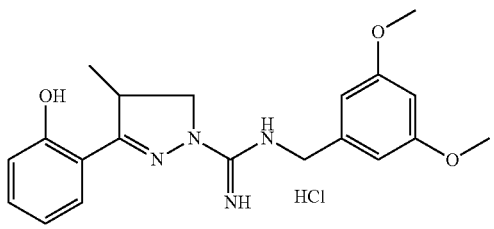 [SMILES: COc1cc(CNC(=N)N2CC(C)C(c3ccccc3O)=N2)cc(OC)c1 ; Cl]

Prepared by the method described in Example 56.
Yield: 0.24 g (60%).
$^1$H NMR ((CD$_3$)$_2$SO, 400 MHz) δ: 1.19 (d, 3H), 3.70-3.80 (m, 1H), 3.74 (s, 6H), 4.10-4.20 (m, 2H), 4.50 (d, 2H), 6.44 (s, 1H), 6.58 (s, 2H), 6.92 (t, 1H), 7.01 (d, 1H), 7.34 (t, 1H), 7.71 (d, 1H), 8.14 (s, 2H), 8.71 (t, 1H), 9.98 (s, 1H).

Example 62

N-(3-chloro-4-methoxybenzyl)-3-(2-hydroxyphenyl)-4-methyl-4,5-dihydro-1H-pyrazole-1-carboximidamide

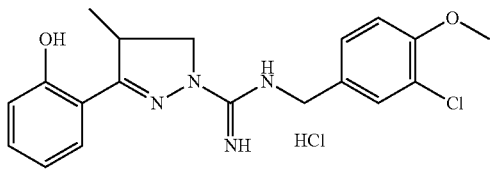 [SMILES: COc1ccc(CNC(=N)N2CC(C)C(c3ccccc3O)=N2)cc1Cl ; Cl]

Prepared by the method described in Example 55 without salt-formation.
Yield: 0.20 g (54%).
$^1$H NMR (CDCl$_3$, 400 MHz) δ: 1.34 (d, 3H), 3.80 (m, 1H), 3.92 (d, 1H), 4.03 (t, 1H), 4.47 (s, 2H), 6.88 (d, 1H), 6.94 (t, 1H), 7.00 (d, 1H), 7.25-7.35 (m, 3H), 7.41 (s, 1H).

Example 63

3-(2-Hydroxyphenyl)-4-methyl-N—((R)-1-phenylethyl)-4,5-dihydro-1H-pyrazole-1-carboximidamide Exemplified by its Hydrochloride Salt

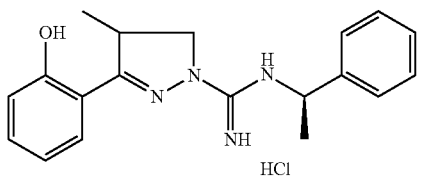 [SMILES: CC1CN(C(=N)N[C@H](C)c2ccccc2)N=C1c1ccccc1O ; Cl]

Prepared by the method described in Example 56.
Yield: 0.040 g (11%).
$^1$H NMR (CDCl$_3$, 400 MHz) δ: (diastereomeric mixture, 1:1) 1.23 and 1.35 (broad s and d, 3H), 1.71 (d, 3H), 1.87 (broad s, 1H), 3.88 and 3.96 (2m, 1H), 4.20-4.43 (m, 2H), 5.35-5.49 (m, 1H), 6.95 (t, 1H), 7.08 (d, 1H), 7.23-7.40 (m, 5H), 7.46 (d, 1H), 7.51 (d, 1H), 8.29 (broad s, 2H), 9.26 and 9.36 (2s, 1H).

Example 64

3-(2-Hydroxyphenyl)-4-methyl-N—((S)-1-phenylethyl)-4,5-dihydro-1H-pyrazole-1-carboximidamide Exemplified by its Hydrochloride Salt

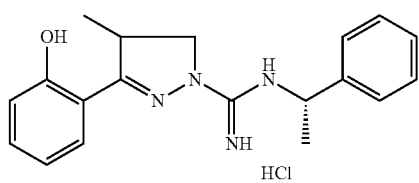 [SMILES: CC1CN(C(=N)N[C@@H](C)c2ccccc2)N=C1c1ccccc1O ; Cl]

Prepared by the method described in Example 56.
Yield: 0.036 g (10%).
$^1$H NMR (CD$_3$OD, 400 MHz) δ: (diastereomeric mixture, 1:1) 1.32 (d, 3H), 1.66 and 1.66 (2d, 3H), 3.80 (m, 1H), 4.14 (t, 1H), 4.23 (m, 1H), 4.93 (m, 1H), 6.93-6.99 (m, 2H), 7.28-7.46 (m, 6H), 7.67 (d, 1H).

Example 65

3-(2-hydroxyphenyl)-4-methyl-N-phenethyl-4,5-dihydro-1H-pyrazole-1-carboximidamide Exemplified by its Hydrochloride Salt

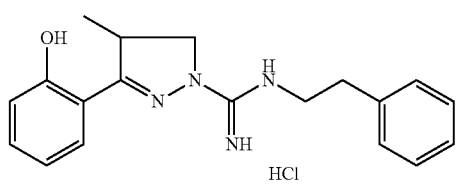 [SMILES: CC1CN(C(=N)NCCc2ccccc2)N=C1c1ccccc1O ; Cl]

Prepared by the method described in Example 56.
Yield: 0.105 g (29%).
$^1$H NMR ((CD$_3$)$_2$SO, 400 MHz) δ: 1.17 (d, 3H), 2.89 (t, 2H), 3.55 (m, 2H), 3.73 (m, 1H), 4.03-4.19 (m, 2H), 6.92 (t, 1H), 7.04 (d, 1H), 7.23 (m, 1H), 7.27-7.37 (m, 5H), 7.71 (d, 1H), 8.18 (s, 2H), 8.26 (t, 1H), 10.04 (s, 1H).

Example 66

3-(2,4-Dimethoxyphenyl)-4-methyl-4,5-dihydro-1H-pyrazole-1-carboximidamide

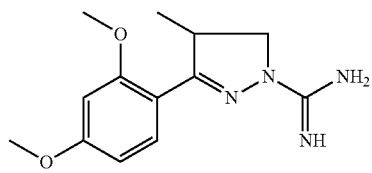 [SMILES: COc1ccc(C2=NN(C(=N)N)CC2C)c(OC)c1]

Prepared by the method described in Example 45.
Yield: 1.10 g (69%).
$^1$H NMR (CDCl$_3$, 400 MHz) δ: 1.14 (d, 3H), 3.66 (dd, 1H), 3.84 (s, 3H), 3.84 (s, 3H), 3.99 (m, 1H), 4.16 (t, 1H), 5.69 (s, 3H), 6.47 (d, 1H), 6.52 (dd, 1H), 7.60 (d, 1H).

Example 67

3-(2,4-Dihydroxyphenyl)-4-methyl-4,5-dihydro-1H-pyrazole-1-carboximidamide Exemplified by its Hydrobromide Salt

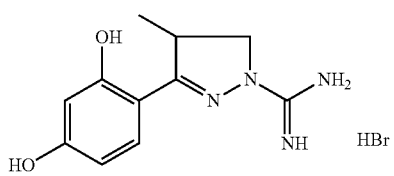 [SMILES: CC1CN(C(=N)N)N=C1c1ccc(O)cc1O ; Br]

Prepared by the method described in Example 46 using 8 eq. of BBr$_3$.
The crude product was purified by silica column chromatography (EtOAc:MeOH:AcOH, 80:20:1) and then recrystallized from EtOH (abs.).
Yield: 47 mg (12%).
$^1$H NMR (CD$_3$OD, 400 MHz) δ: 1.34 (d, 3H), 3.74 (dd, 1H), 4.01 (t, 1H), 4.11 (m, 1H), 6.39 (s, 1H), 6.43 (d, 1H), 7.45 (d, 1H).

Example 68

3-(2-Methoxy-4-(trifluoromethyl)phenyl)-4-methyl-4,5-dihydro-1H-pyrazole-1-carboximidamide Exemplified by its Hydrochloride Salt

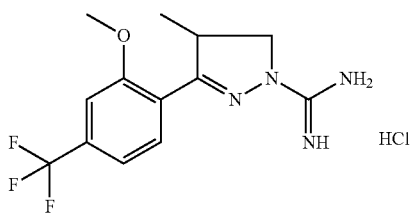 [SMILES: COc1cc(C(F)(F)F)ccc1C1=NN(C(=N)N)CC1C ; Cl]

Prepared by the method described in Example 45 isolated as the HCl-salt without free-basing.
Yield: 0.34 g (36%).
$^1$H NMR ((CD$_3$)$_2$SO, 400 MHz) δ: 1.10 (d, 3H), 3.66 (dd, 1H), 3.96 (s, 3H), 4.11 (m, 1H), 4.22 (t, 1H), 7.41 (d, 1H), 7.46 (s, 1H), 7.94 (s, 4H), 7.99 (d, 1H).

Example 69

3-(2-Hydroxy-4-(trifluoromethyl)phenyl)-4-methyl-4,5-dihydro-1H-pyrazole-1-carboximidamide Exemplified by its Hydrochloride Salt

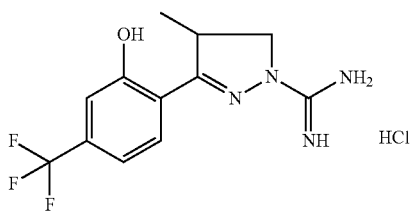 [SMILES: CC1CN(C(=N)N)N=C1c1ccc(C(F)(F)F)cc1O ; Cl]

Prepared by the method described in Example 46.
Yield: 0.22 g (53%).
$^1$H NMR ((CD$_3$)$_2$SO, 400 MHz) δ: 1.17 (d, 3H), 3.69 (m, 1H), 4.10-4.23 (m, 2H), 7.26 (d, 1H), 7.28 (s, 1H), 7.79 (s, 4H), 7.95 (d, 1H), 10.63 (s, 1H).

Example 70

3-(1H-Indol-3-yl)-4-methyl-4,5-dihydro-1H-pyrazole-1-carboximidamide Exemplified by its Hydrochloride Salt

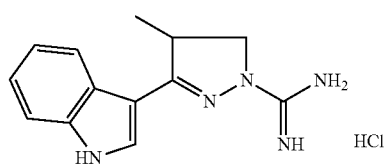 [SMILES: CC1CN(C(=N)N)N=C1c1c[nH]c2ccccc12 ; Cl]

Prepared from 1-(1H-indol-3-yl)-2-methylprop-2-en-1-one by the method described in Example 23.
Yield: 0.23 g (36%).
$^1$H NMR ((CD$_3$)$_2$SO, 400 MHz) δ: 1.33 (d, 3H), 3.72 (d, 1H), 3.90-4.02 (m, 2H), 7.14 (t, 1H), 7.21 (t, 1H), 7.46 (d, 1H), 7.87 (s, 4H), 8.03 (s, 1H), 8.37 (d, 1H), 11.99 (s, 1H).

Example 71

4-Methyl-3-(quinolin-4-yl)-4,5-dihydro-1H-pyrazole-1-carboximidamide

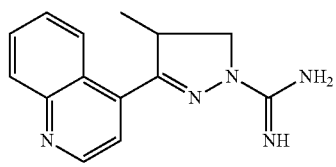 [SMILES: CC1CN(C(=N)N)N=C1c1ccnc2ccccc12]

Prepared from 2-methyl-1-(quinolin-4-yl)prop-2-en-1-one by the method described in Example 23. After completing the reaction the reaction mixture was concentrated at reduced pressure and the residue was stirred with CH$_2$Cl$_2$ (25 mL) for 5 min. The product was isolated by filtration and concentration of the filtrate at reduced pressure followed by crystallization from EtOAc (20 mL). The crystals were collected by filtration, washed with Et$_2$O and dried to give the title compound (0.29 g, 56%).

$^1$H NMR (CDCl$_3$, 400 MHz) δ: 1.34 (d, 3H), 3.63 (m, 1H), 3.90 (dd, 1H), 4.04 (t, 1H), 6.48 (broad s, 1H), 7.30 (m, 2H), 7.45 (d, 1H), 7.51 (m, 1H), 8.19 (d, 1H), 8.75 (broad s, 1H), 9.06 (s, 1H).

Example 72

(S)*-3-(3-chloro-2-hydroxyphenyl)-4-methyl-4,5-dihydro-1H-pyrazole-1-carboximidamide Exemplified by its Hydrochloride Salt

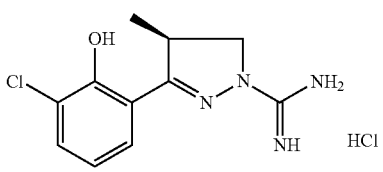 [SMILES: C[C@H]1CN(C(=N)N)N=C1c1cccc(Cl)c1O ; Cl]

and

Example 73

(R)*-3-(3-chloro-2-hydroxyphenyl)-4-methyl-4,5-dihydro-1H-pyrazole-1-carboximidamide Exemplified by its Hydrochloride Salt

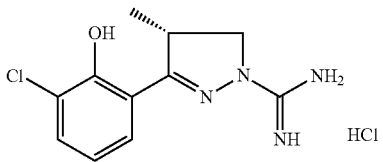 [SMILES: C[C@@H]1CN(C(=N)N)N=C1c1cccc(Cl)c1O ; Cl]

The enantiomers were separated and purified by SFC (Supercritical Fluid Chromatography) using an Amy-C column (20 mm×250 mm, 5 um) with EtOH/CO$_2$ (40%) as eluent (NH$_3$ 0.1% was added as a modifier) with 50 mL/min flow rate and UV-detection at 215 nm wavelength.

The racemate compound HBr-salt (154 mg) was dissolved in methanol (50 mg/mL) and injected in 0.4 mL (20 mg) volumes. The combined fractions of each enantiomer (isomer 1 at 2.47 min and isomer 2 at 3.05 min) were concentrated at reduced pressure and then redissolved in EtOH. The HCl-salt of each enantiomer was precipitated by addition of a saturated solution of HCl in EtOH, followed by evaporation of the solvent and drying in a vacuum oven at 40° C. to give the title product.

The final chiral analysis was performed by SFC (Amy-C column, 4.6 mm×250 mm, 5 um). The eluent was EtOH/CO$_2$ (40%) (NH$_3$ 0.1% was added as a modifier) with 4 mL/min flow rate.

The chemical purity was determined by HPLC (C18, water/MeCN, 0.1% TFA).

For isomer 1:
(S)*-configuration (based on biological activity and absolute configuration of Ex. 37);
Yield 62 mg;
Chemical purity (240 nm): 99.3%;
Enantiomeric excess: 97.2.
For isomer 2:
(R)*-configuration (based on biological activity and absolute configuration of Ex. 38);
Yield 65 mg;
Chemical purity (240 nm): 99.4%;
Enantiomeric excess: 98.8.

Example 74

N-Benzyl-3-(3-chloro-2-methoxyphenyl)-4-methyl-4,5-dihydro-1H-pyrazole-1-carboximidamide

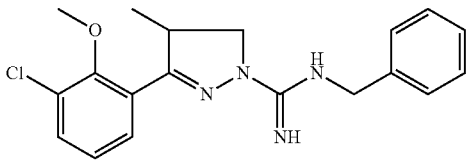 [SMILES: COc1c(Cl)cccc1C1=NN(C(=N)NCc2ccccc2)CC1C]

Prepared by essentially the same methods as described in Example 39 and Example 41.

1-(3-chloro-2-methoxyphenyl)-3-(dimethylamino)-2-methylpropan-1-one

For the starting material 1-(3-chloro-2-methoxyphenyl)propan-1-one, see DE 102005014089 A1.
Yield: 45.3 g (68%).
$^1$H NMR (CDCl$_3$, 400 MHz) δ: 1.16 (d, 3H), 2.20 (s, 6H), 2.28 (dd, 1H), 2.70 (dd, 1H), 3.54 (m, 1H), 3.88 (s, 3H), 7.11 (t, 1H), 7.35 (dd, 1H), 7.48 (dd, 1H).

3-(3-Chloro-2-methoxyphenyl)-4-methyl-4,5-dihydro-1H-pyrazole-1-carbothioamide

Yield: 27.5 g (99%).
$^1$H NMR (CDCl$_3$, 400 MHz) δ: 1.18 (d, 3H), 3.83 (s, 3H), 3.89 (m, 1H), 3.99 (dd, 1H), 4.52 (dd, 1H), 7.12 (t, 1H), 7.48 (dd, 1H), 7.50 (dd, 1H).

Methyl 3-(3-chloro-2-methoxyphenyl)-4-methyl-4,5-dihydro-1H-pyrazole-1-carbimidothioate Hydroiodide Yield: 33.0 g (80%).
$^1$H NMR ((CD$_3$)$_2$SO, 400 MHz) δ: 1.14 (d, 3H), 2.64 (s, 3H), 3.83 (s, 3H), 3.73-3.88 (m, 1H), 3.83 (s, 3H), 4.17 (m, 1H), 4.39 (t, 1H), 7.32 (t, 1H), 7.58-7.82 (m, 2H), 9.1-9.7 (2 broad s, 2H).

N-Benzyl-3-(3-chloro-2-methoxyphenyl)-4-methyl-4,5-dihydro-1H-pyrazole-1-carboximidamide Yield: 2.80 g (77%).
$^1$H NMR (CDCl$_3$, 400 MHz) δ: 1.17 (d, 3H), 3.74 (dd, 1H), 3.81 (s, 3H), 3.86 (m, 1H), 4.22 (t, 1H), 4.48 (s, 2H), 7.08 (t, 1H), 7.28 (tt, 1H), 7.32-7.43 (m, 5H), 7.49 (dd, 1H).

Example 75

N-Benzyl-3-(3-chloro-2-hydroxyphenyl)-4-methyl-4,5-dihydro-1H-pyrazole-1-carboximidamide Exemplified by its Hydrochloride Salt

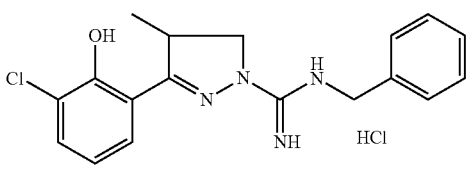 [SMILES: CC1CN(C(=N)NCc2ccccc2)N=C1c1cccc(Cl)c1O ; Cl]

Prepared by the method described in Example 40, followed by HCl-salt precipitation.

Yield: 1.20 g (40%).

$^1$H NMR (CD$_3$)$_2$SO, 400 MHz) δ: 1.22 (d, 3H), 3.89 (m, 1H), 4.08-4.20 (m, 2H), 4.62 (s, 2H), 7.01 (t, 1H), 7.31 (m, 1H), 7.36-7.43 (m, 4H), 7.55-7.63 (m, 2H).

Example 76

(R)*—N-Benzyl-3-(3-chloro-2-hydroxyphenyl)-4-methyl-4,5-dihydro-1H-pyrazole-1-carboximidamide Exemplified by its Hydrochloride Salt

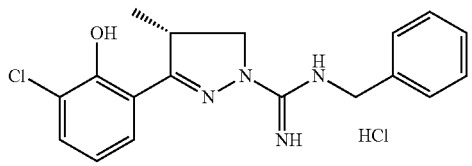 [SMILES: C[C@@H]1CN(C(=N)NCc2ccccc2)N=C1c1cccc(Cl)c1O ; Cl]

and

Example 77

(S)*—N-Benzyl-3-(3-chloro-2-hydroxyphenyl)-4-methyl-4,5-dihydro-1H-pyrazole-1-carboximidamide Exemplified by its Hydrochloride Salt

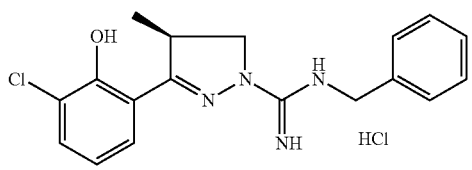 [SMILES: C[C@H]1CN(C(=N)NCc2ccccc2)N=C1c1cccc(Cl)c1O ; Cl]

The enantiomers were separated and purified by SFC (Supercritical Fluid Chromatography) using an Amy-C column (20 mm×250 mm, 5 um) with EtOH/CO$_2$ (40%) as eluent (NH$_3$ 0.1% was added as a modifier) with 50 mL/min flow rate and UV-detection at 210 nm wavelength.

The racemate compound HCl-salt (1.00 g) was dissolved in methanol (27 mg/mL) and injected in 0.3 mL (8 mg) volumes. The combined fractions of each enantiomer (isomer 1 at 1.82 min and isomer 2 at 2.38 min) were concentrated at reduced pressure and then redissolved in EtOH. The HCl-salt of each enantiomer was precipitated by addition of a saturated solution of HCl in EtOH, followed by evaporation of the solvent and drying in a vacuum oven at 40° C. to give the title product.

The final chiral analysis was performed by SFC (Amy-C column, 4.6 mm×250 mm, 5 um). The eluent was EtOH/CO$_2$ (35%) (NH$_3$ 0.1% was added as a modifier) with 4 mL/min flow rate.

The chemical purity was determined by HPLC (C18, water/MeCN, 0.1% TFA).

For isomer 1:
(R)*-configuration (based on biological activity and absolute configuration of Ex. 38);
Yield 404 mg;
Chemical purity (240 nm): 98.3%;
Enantiomeric excess: >95.

For isomer 2:
(S)*-configuration (based on biological activity and absolute configuration of Ex. 37);
Yield 364 mg;
Chemical purity (240 nm): 99.4%;
Enantiomeric excess: 99.6.

The following compounds (Examples 78-91) were prepared by the methods described in Example 74 using the corresponding amines or aniline as nucleophiles. Demethylations to give phenol derivatives were performed using the method described in Example 40, optionally followed by HCl-salt precipitation.

Example 78

N-butyl-3-(3-chloro-2-methoxyphenyl)-4-methyl-4,5-dihydro-1H-pyrazole-1-carboximidamide Exemplified by its Hydrochloride Salt

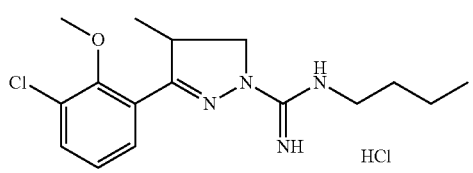 [SMILES: CCCCNC(=N)N1CC(C)C(c2cccc(Cl)c2OC)=N1 ; Cl]

Yield: 0.34 g (81%).

$^1$H NMR ((CD$_3$)$_2$SO, 400 MHz) δ: 0.90 (t, 3H), 1.10 (d, 3H), 1.33 (m, 2H), 1.52 (m, 2H), 3.29 (t, 2H), 3.72 (dd, 1H), 3.79 (s, 3H), 4.02 (m, 1H), 4.27 (t, 1H), 7.27 (t, 1H), 7.66 (dd, 1H), 7.78 (dd, 1H), 8.14 (s, 3H).

Example 79

N-Butyl-3-(3-chloro-2-hydroxyphenyl)-4-methyl-4,5-dihydro-1H-pyrazole-1-carboximidamide Exemplified by its Hydrochloride Salt

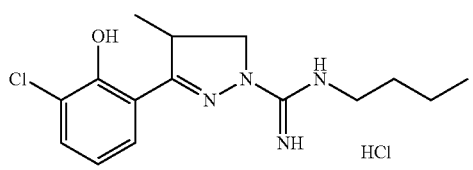 [SMILES: CCCCNC(=N)N1CC(C)C(c2cccc(Cl)c2O)=N1 ; Cl]

Yield: 0.13 g (40%).

$^1$H NMR (CD$_3$OD, 400 MHz) δ: 0.99 (t, 3H), 1.24 (d, 3H), 1.43 (m, 2H), 1.64 (m, 2H), 3.3 (t, 2H, in solvent peak), 3.62 (dd, 1H), 4.02 (t, 1H), 4.31 (m, 1H), 6.45 (t, 1H), 7.28 (d, 1H), 7.36 (d, 1H).

Example 80

3-(3-Chloro-2-methoxyphenyl)-N-hexyl-4-methyl-4,5-dihydro-1H-pyrazole-1-carboximidamide

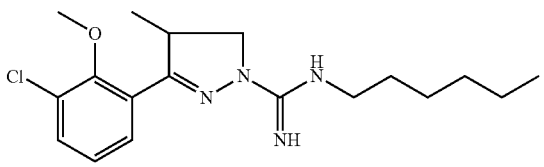 [SMILES: CCCCCCNC(=N)N1CC(C)C(c2cccc(Cl)c2OC)=N1]

Yield: 0.30 g (91%).
¹H NMR (CDCl₃, 400 MHz) δ: 0.89 (t, 3H), 1.24 (d, 3H), 1.26-1.38 (m, 4H), 1.43 (m, 2H), 1.65-1.84 (m, 2H), 3.63 (q, 2H), 3.85 (s, 3H), 4.05-4.16 (m, 2H), 4.71 (t, 1H), 6.32 (broad s, 1H), 7.15 (t, 1H), 7.51 (broad d, 1H), 7.52 (dd, 1H), 7.72 (broad s, 2H).

Example 81

3-(3-Chloro-2-hydroxyphenyl)-N-hexyl-4-methyl-4,5-dihydro-1H-pyrazole-1-carboximidamide Exemplified by its Hydrochloride Salt

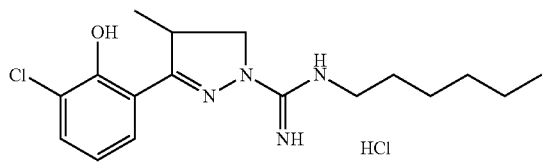 [SMILES: CCCCCCNC(=N)N1CC(C)C(c2cccc(Cl)c2O)=N1 ; Cl]

Yield: 82 mg (30%).
¹H NMR (CD₃OD, 400 MHz) δ: 0.93 (t, 3H), 1.26 (d, 3H), 1.32-1.46 (m, 6H), 1.66 (m, 2H), 3.31 (t, 2H, in solvent peak), 3.66 (dd, 1H), 4.04 (t, 1H), 4.28 (m, 1H), 6.58 (t, 1H), 7.33 (d, 1H), 7.41 (d, 1H).

Example 82

3-(3-Chloro-2-methoxyphenyl)-N-dodecyl-4-methyl-4,5-dihydro-1H-pyrazole-1-carboximidamide Exemplified by its Hydrochloride Salt

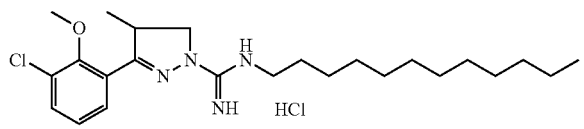 [SMILES: CCCCCCCCCCCCNC(=N)N1CC(C)C(c2cccc(Cl)c2OC)=N1 ; Cl]

Yield: 0.31 g (70%).
¹H NMR (CD₃OD, 400 MHz) δ: 0.90 (t, 3H), 1.21 (d, 3H), 1.23-1.45 (m, 18H), 1.67 (m, 2H), 3.34 (t, 2H, partly in solvent peak), 3.71 (dd, 1H), 3.86 (s, 3H), 4.15 (m, 1H), 4.27 (t, 1H), 7.22 (t, 1H), 7.59 (d, 1H), 7.71 (d, 1H).

Example 83

3-(3-Chloro-2-hydroxyphenyl)-N-dodecyl-4-methyl-4,5-dihydro-1H-pyrazole-1-carboximidamide Exemplified by its Hydrochloride Salt

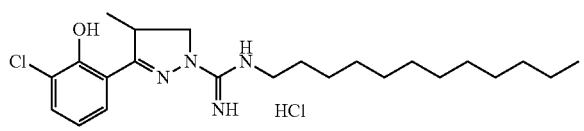 [SMILES: CCCCCCCCCCCCNC(=N)N1CC(C)C(c2cccc(Cl)c2O)=N1 ; Cl]

Yield: 135 mg (40%).
¹H NMR (CD₃OD, 400 MHz) δ: 0.90 (t, 3H), 1.21 (d, 3H), 1.22-1.45 (m, 18H), 1.65 (m, 2H), 3.28 (t, 2H, partly in solvent peak), 3.57 (dd, 1H), 4.00 (t, 1H), 4.35 (m, 1H), 6.32 (t, 1H), 7.23 (d, 1H), 7.30 (d, 1H).

Example 84

3-(3-Chloro-2-methoxyphenyl)-N-cyclohexyl-4-methyl-4,5-dihydro-1H-pyrazole-1-carboximidamide

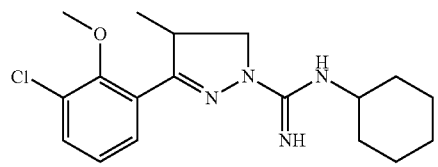 [SMILES: COc1c(Cl)cccc1C1=NN(C(=N)NC2CCCCC2)CC1C]

Yield: 0.16 g (44%).
¹H NMR (CDCl₃, 400 MHz) δ: 1.10-1.35 (m, 3H), 1.17 (d, 3H), 1.50 (m, 2H), 1.64 (m, 1H), 1.73 (m, 2H), 2.06 (t, 2H), 3.75 (m, 1H), 3.31-3.95 (m, 2H), 3.83 (s, 3H), 4.39 (t, 1H), 7.11 (t, 1H), 7.45 (dd, 1H), 7.49 (dd, 1H).

Example 85

3-(3-Chloro-2-hydroxyphenyl)-N-cyclohexyl-4-methyl-4,5-dihydro-1H-pyrazole-1-carboximidamide

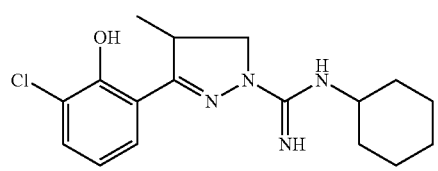 [SMILES: CC1CN(C(=N)NC2CCCCC2)N=C1c1cccc(Cl)c1O]

Yield: 90 mg (59%).
¹H NMR (CD₃OD, 400 MHz) δ: 1.18-1.30 (m, 1H), 1.23 (d, 3H), 1.42 (m, 4H), 1.69 (m, 1H), 1.83 (m, 2H), 1.98 (m, 2H), 3.47 (m, 1H), 3.62 (dd, 1H), 4.01 (t, 1H), 4.29 (m, 1H), 6.42 (t, 1H), 7.27 (d, 1H), 7.32 (d, 1H).

Example 86

3-(3-Chloro-2-methoxyphenyl)-N-cyclopropyl-4-methyl-4,5-dihydro-1H-pyrazole-1-carboximidamide Exemplified by its Hydrochloride Salt

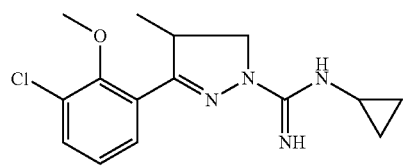

Yield: 0.35 g (87%).
¹H NMR (CD₃OD, 400 MHz) δ: 0.78 (m, 2H), 0.95 (m, 2H), 1.20 (d, 3H), 2.65 (m, 1H), 3.67 (dd, 1H), 3.85 (s, 3H), 4.14 (m, 1H), 4.25 (dd, 1H), 7.22 (t, 1H), 7.58 (dd, 1H), 7.70 (dd, 1H).

Example 87

3-(3-Chloro-2-hydroxyphenyl)-N-cyclopropyl-4-methyl-4,5-dihydro-1H-pyrazole-1-carboximidamide Exemplified by its Hydrochloride Salt

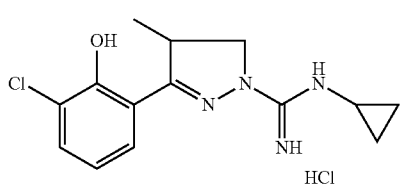 [SMILES: CC1CN(C(=N)NC2CC2)N=C1c1cccc(Cl)c1O ; Cl]

Yield: 65 mg (20%).

$^1$H NMR (CD$_3$OD, 400 MHz) δ: 0.76 (m, 2H), 0.93 (m, 2H), 1.25 (d, 3H), 2.62 (m, 1H), 3.62 (dd, 1H), 4.00 (t, 1H), 4.26 (m, 1H), 6.56 (t, 1H), 7.33 (dd, 1H), 7.39 (dd, 1H).

Example 88

3-(3-Chloro-2-methoxyphenyl)-4-methyl-N-phenyl-4,5-dihydro-1H-pyrazole-1-carboximidamide Exemplified by its Hydrochloride Salt

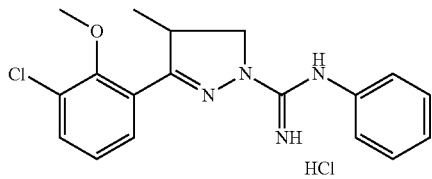 [SMILES: COc1c(Cl)cccc1C1=NN(C(=N)Nc2ccccc2)CC1C ; Cl]

Yield: 30 mg (28%).

$^1$H NMR (CD$_3$OD, 400 MHz) δ: 1.26 (d, 3H), 3.84 (dd, 1H), 3.89 (s, 3H), 4.23 (m, 1H), 4.41 (t, 1H), 7.24 (t, 1H), 7.37-7.44 (m, 3H), 7.52 (t, 2H), 7.61 (d, 1H), 7.76 (d, 1H).

Example 89

3-(3-Chloro-2-hydroxyphenyl)-4-methyl-N-phenyl-4,5-dihydro-1H-pyrazole-1-carboximidamide Exemplified by its Hydrochloride Salt

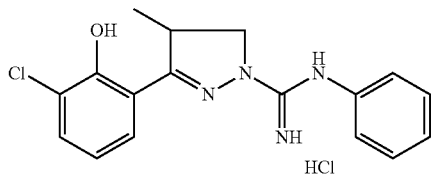 [SMILES: CC1CN(C(=N)Nc2ccccc2)N=C1c1cccc(Cl)c1O ; Cl]

Yield: 80 mg (37%).

$^1$H NMR (CD$_3$OD, 400 MHz) δ: 1.37 (d, 3H), 3.90 (dd, 1H), 4.22 (m, 2H), 6.93 (t, 1H), 7.33-7.40 (m, 3H), 7.46-7.53 (m, 3H), 7.59 (d, 1H).

Example 90

3-(3-Chloro-2-methoxyphenyl)-N-cyano-4-methyl-4,5-dihydro-1H-pyrazole-1-carboximidamide

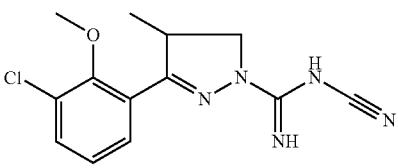 [SMILES: COc1c(Cl)cccc1C1=NN(C(=N)NC#N)CC1C]

Yield: 105 mg (36%).

$^1$H NMR ((CD$_3$)$_2$SO, 400 MHz) δ: 1.06 (d, 3H), 3.57 (dd, 1H), 3.78 (s, 3H), 3.86 (m, 1H), 4.10 (t, 1H), 7.23 (t, 1H), 7.53 (s, 2H), 7.61 (dd, 1H), 7.80 (dd, 1H).

Example 91

3-(3-Chloro-2-hydroxyphenyl)-N-cyano-4-methyl-4,5-dihydro-1H-pyrazole-1-carboximidamide

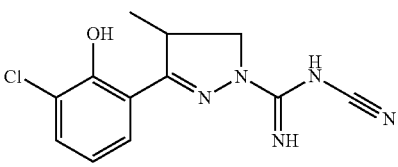 [SMILES: CC1CN(C(=N)NC#N)N=C1c1cccc(Cl)c1O]

Yield: 0.13 g (18%).

$^1$H NMR ((CD$_3$)$_2$SO, 400 MHz) δ: 1.17 (d, 3H), 3.67 (m, 1H), 3.85-3.96 (m, 2H), 6.98 (t, 1H), 7.51-7.57 (m, 2H), 7.96 (s, 2H), 9.97 (s, 1H).

Example 92

N-(2,2,3,3,4,4,4-Heptafluorobutyl)-3-(2-methoxyphenyl)-4-methyl-4,5-dihydro-1H-pyrazole-1-carboximidamide Exemplified by its Hydrochloride Salt

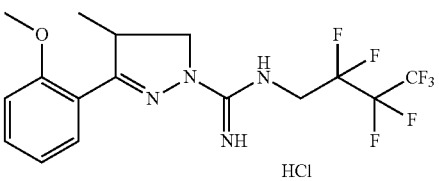 [SMILES: COc1ccccc1C1=NN(C(=N)NCC(F)(F)C(F)(F)C(F)(F)F)CC1C ; Cl]

N-((2,2,3,3,4,4,4-heptafluorobutyl)carbamothioyl)benzamide

A solution of benzoyl isothiocyanate (2.63 g, 16.1 mmol) in acetone (5 mL) was added to a solution of 2,2,3,3,4,4,4-heptafluorobutylamine (3.20 g, 16.1 mmol) in acetone (45 mL). After stirring at 50° C. for 8 h the reaction mixture was concentrated at reduced pressure to give the title compound as pale yellow crystals (5.9 g, quant.).

¹H NMR (CDCl₃, 400 MHz) δ: 4.59 (dt, 2H), 7.55 (t, 2H), 7.67 (t, 1H), 7.87 (d, 2H), 9.15 (s, 1H), 11.19 (s, 1H).

1-(2,2,3,3,4,4,4-Heptafluorobutyl)thiourea

A solution of aq. NaOH (16.2 mL, 2M) was added to a solution of N-((2,2,3,3,4,4,4-heptafluorobutyl)carbamothioyl)benzamide (5.83 g, 16.1 mmol) in MeOH (40 mL). The reaction mixture was stirred at 65° C. for 3 h. After cooling, the reaction mixture was neutralized with aq. HCl (conc., 2.7 mL) and concentrated at reduced pressure to approximately half the volume. The formed crystals were collected by filtration, washed with water, and dried to give the title compound (1.40 g, 34%).
¹H NMR (CD₃)₂SO, 400 MHz) δ: 4.50 (broad t, 2H), 7.23 (broad s, 1H), 7.82 (broad s, 1H), 8.01 (t, 1H).

1-(2,2,3,3,4,4,4-Heptafluorobutyl)-2-methylisothiouronium Iodide

A solution of 1-(2,2,3,3,4,4,4-heptafluorobutyl)thiourea (1.40 g, 5.42 mmol) and MeI (1.53 g, 10.8 mmol) in MeOH (10 mL) was stirred at 70° C. in a sealed vial for 4 h. After cooling, the reaction mixture was concentrated at reduced pressure to give the title compound as a brown solid (2.17 g, quant.).
¹H NMR (CD₃)₂SO, 400 MHz) δ: 2.66 (s, 3H), 4.43 (t, 2H), 9.50 (broad s, 1H), 9.75 (broad s, 1H), 10.07 (broad s, 1H).

((2,2,3,3,4,4,4-Heptafluorobutyl)amino)(hydrazinyl)methaniminium Iodide

A solution of 1-(2,2,3,3,4,4,4-heptafluorobutyl)-2-methylisothiouronium iodide (2.17 g, 5.42 mmol) and hydrazine hydrate (0.407 g, 8.13 mmol) in MeOH (20 mL) was stirred at reflux temperature for 3 h. After cooling, the reaction mixture was concentrated at reduced pressure to give the title compound as brown oil which solidifies on standing (2.10 g, quant.).
¹H NMR (CD₃)₂SO, 400 MHz) δ: 4.19 (t, 2H), 6.20 (broad s, 6H).

N-(2,2,3,3,4,4,4-Heptafluorobutyl)-3-(2-methoxyphenyl)-4-methyl-4,5-dihydro-1H-pyrazole-1-carboximidamide Hydrochloride NaOH (aq. 50%, 0.7 mL, ca 13 mmol) was added to a solution of ((2,2,3,3,4,4,4-heptafluorobutyl)amino)(hydrazinyl)methaniminium iodide (650 mg, 1.69 mmol) and 3-(dimethylamino)-1-(2-methoxyphenyl)-2-methylpropan-1-one (375 mg, 1.69 mmol) in MeOH (20 mL). The reaction mixture was stirred at reflux temperature for 3 h and was then concentrated at reduced pressure. The residue was partitioned in water and CH₂Cl₂. The organic phase was washed with water and concentrated at reduced pressure. The residue was purified by silica column chromatography (CH₂Cl₂-MeOH—NH₃, 160:10:1) to give the base of the title compound as a yellow oil (240 mg, 34%). This was dissolved in EtOAc (5 mL) and the HCl-salt was precipitated by addition of 2M HCl/Et₂O, collected by filtration, and dried to give the title compound (230 mg, 30%).
¹H NMR (CD₃)₂SO, 400 MHz) δ: 1.11 (d, 3H), 3.72 (dd, 1H), 3.87 (s, 3H), 4.13 (m, 1H), 4.29 (t, 1H), 4.41 (t, 2H), 7.06 (t, 1H), 7.18 (d, 1H), 7.52 (dt, 1H), 7.80 (dd, 1H), 8.55-8.70 (2 broad s, 3H).

Example 93

N-(2,2,3,3,4,4,4-Heptafluorobutyl)-3-(2-hydroxyphenyl)-4-methyl-4,5-dihydro-1H-pyrazole-1-carboximidamide Exemplified by its Hydrochloride Salt

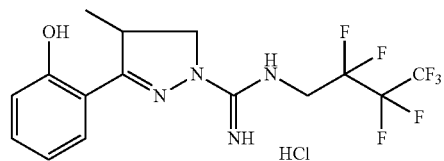 [SMILES: CC1CN(C(=N)NCC(F)(F)C(F)(F)C(F)(F)F)N=C1c1ccccc1O ; Cl]

Prepared by the method described in Example 40, followed by HCl-salt precipitation.
Yield: 140 mg (72%).
¹H NMR (CD₃)₂SO, 400 MHz) δ: 1.19 (d, 3H), 3.75 (m, 1H), 4.13-4.23 (m, 2H), 4.37 (dq, 2H), 6.93 (t, 1H), 7.02 (d, 1H), 7.36 (dt, 1H), 7.72 (dd, 1H), 8.55 (broad s, 2H), 8.63 (broad s, 1H), 10.09 (s, 1H).

Example 94

3-(2-Methoxyphenyl)-4-methyl-N-(2,2,2-trifluoroethyl)-4,5-dihydro-1H-pyrazole-1-carboximidamide Exemplified by its Hydrochloride Salt

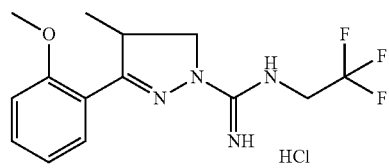 [SMILES: COc1ccccc1C1=NN(C(=N)NCC(F)(F)F)CC1C ; Cl]

Prepared by the methods described in Example 92 using 2,2,2-trifluoroethanamine as starting material.
Yield: 0.67 g (49%).
¹H NMR (CD₃)₂SO, 400 MHz) δ: 1.11 (d, 3H), 3.71 (dd, 1H), 3.87 (s, 3H), 4.12 (m, 1H), 4.23-4.37 (m, 3H), 7.05 (t, 1H), 7.17 (d, 1H), 7.51 (dt, 1H), 7.82 (dd, 1H), 8.60 (s, 2H), 8.72 (s, 1H).

Example 95

3-(2-Hydroxyphenyl)-4-methyl-N-(2,2,2-trifluoroethyl)-4,5-dihydro-1H-pyrazole-1-carboximidamide Exemplified by its Hydrochloride Salt

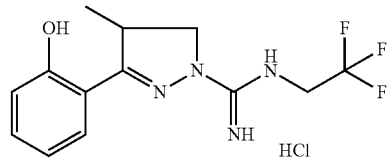 [SMILES: CC1CN(C(=N)NCC(F)(F)F)N=C1c1ccccc1O ; Cl]

Prepared by the method described in Example 40, followed by HCl-salt precipitation.
Yield: 180 mg (69%).
¹H NMR (CD₃)₂SO, 400 MHz) δ: 1.19 (d, 3H), 3.76 (m, 1H), 4.12-4.23 (m, 2H), 4.30 (q, 2H), 6.92 (t, 1H), 7.03 (d, 1H), 7.35 (dt, 1H), 7.73 (dd, 1H), 8.54 (s, 2H), 8.75 (s, 1H), 10.09 (s, 1H).

Example 96

3-(2-Methoxyphenyl)-4-methyl-N-phenyl-4,5-dihydro-1H-pyrazole-1-carboximidamide Exemplified by its Hydrochloride Salt

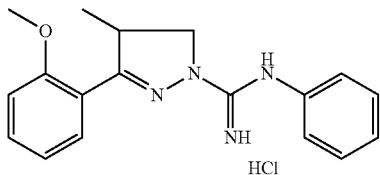 [SMILES: COc1ccccc1C1=NN(C(=N)Nc2ccccc2)CC1C ; Cl]

Prepared by the methods described in Example 92 using aniline as starting material.

Yield: 0.34 g (41%).

$^1$H NMR ((CD$_3$)$_2$SO, 400 MHz) δ: 1.15 (d, 3H), 3.83 (m, 1H), 3.88 (s, 3H), 4.15 (m, 1H), 4.36 (t, 1H), 7.05 (t, 1H), 7.19 (d, 1H), 7.32-7.38 (m, 3H), 7.46-7.54 (m, 3H), 7.89 (dd, 1H), 8.06 (s, 2H), 10.06 (s, 1H).

Example 97

3-(2-Hydroxyphenyl)-4-methyl-N-phenyl-4,5-dihydro-1H-pyrazole-1-carboximidamide

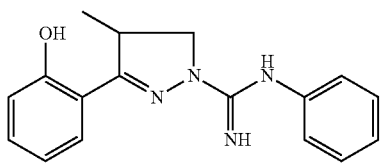 [SMILES: CC1CN(C(=N)Nc2ccccc2)N=C1c1ccccc1O]

Prepared by the method described in Example 40.

Yield: 0.13 g (58%).

$^1$H NMR (CDCl$_3$, 400 MHz) δ: 1.40 (d, 3H), 3.78 (m, 1H), 3.92 (dd, 1H), 4.06 (t, 1H), 4.73 (broad s, 2H), 6.94-7.07 (m, 5H), 7.29-7.37 (m, 4H), 10.00 (broad s, 1H).

Example 98

3-(2-Methoxyphenyl)-4-methyl-N-(4-(trifluoromethyl)phenyl)-4,5-dihydro-1H-pyrazole-1-carboximidamide Exemplified by its Hydrochloride Salt

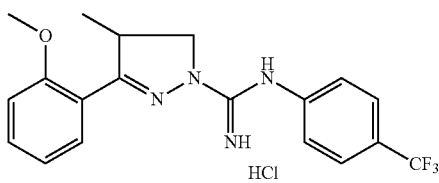 [SMILES: COc1ccccc1C1=NN(C(=N)Nc2ccc(C(F)(F)F)cc2)CC1C ; Cl]

Prepared by the methods described in Example 92 using 4-(trifluoromethyl)aniline as starting material.

Yield: 0.14 g (24%).

$^1$H NMR ((CD$_3$)$_2$SO, 400 MHz) δ: 1.15 (d, 3H), 3.83-3.94 (m, 1H), 3.89 (s, 3H), 4.16 (m, 1H), 4.41 (broad t, 1H), 7.05 (t, 1H), 7.19 (d, 1H), 7.52 (dt, 1H), 7.57 (d, 2H), 7.81-7.88 (m, 3H), 8.37 (s, 2H), 10.43 (broad s, 1H).

Example 99

3-(2-Hydroxyphenyl)-4-methyl-N-(4-(trifluoromethyl)phenyl)-4,5-dihydro-1H-pyrazole-1-carboximidamide Exemplified by its Hydrochloride Salt

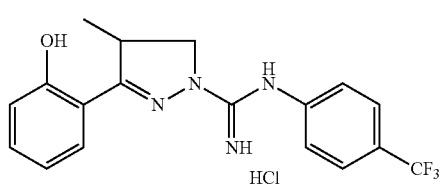 [SMILES: CC1CN(C(=N)Nc2ccc(C(F)(F)F)cc2)N=C1c1ccccc1O ; Cl]

Prepared by the method described in Example 40, followed by HCl-salt precipitation.

Yield: 95 mg (41%).

$^1$H NMR (CD$_3$OD, 400 MHz) δ: 1.38 (d, 3H), 3.90 (m, 1H), 4.24-4.36 (m, 2H), 6.95-7.00 (m, 2H), 7.38 (t, 1H), 7.58 (d, 2H), 7.71 (d, 1H), 7.81 (d, 2H).

Example 100

N-(4-Fluorophenyl)-3-(2-methoxyphenyl)-4-methyl-4,5-dihydro-1H-pyrazole-1-carboximidamide Exemplified by its Hydrochloride Salt

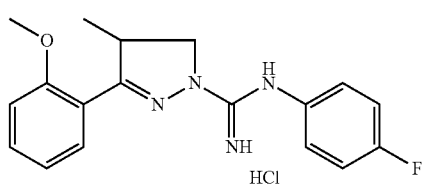 [SMILES: COc1ccccc1C1=NN(C(=N)Nc2ccc(F)cc2)CC1C ; Cl]

Prepared by the methods described in Example 92 using 4-fluoroaniline as starting material.

Yield: 0.16 g (50%).

$^1$H NMR ((CD$_3$)$_2$SO, 400 MHz) δ: 1.14 (d, 3H), 3.83 (m, 1H), 3.88 (s, 3H), 4.14 (m, 1H), 4.36 (t, 1H), 7.05 (t, 1H), 7.18 (d, 1H), 7.32 (t, 2H), 7.40 (dd, 2H), 7.51 (dt, 1H), 7.88 (dd, 1H), 8.03 (s, 2H), 10.09 (s, 1H).

Example 101

N-(4-Fluorophenyl)-3-(2-hydroxyphenyl)-4-methyl-4,5-dihydro-1H-pyrazole-1-carboximidamide

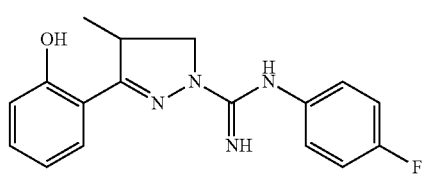 [SMILES: CC1CN(C(=N)Nc2ccc(F)cc2)N=C1c1ccccc1O]

Prepared by the method described in Example 40.
Yield: 165 mg (56%).
¹H NMR ((CD₃)₂SO, 400 MHz) δ: 1.19 (d, 3H), 3.65 (dd, 1H), 3.79-3.88 (m, 1H), 3.89 (t, 1H), 5.89 (s, 2H), 6.82 (dd, 2H), 6.92 (t, 1H), 6.94 (d, 1H), 7.04 (t, 2H), 7.27 (dt, 1H), 7.53 (dd, 1H), 9.85 (s, 1H).

Example 102

N-(4-Chlorophenyl)-3-(2-methoxyphenyl)-4-methyl-4,5-dihydro-1H-pyrazole-1-carboximidamide Exemplified by its Hydrochloride Salt

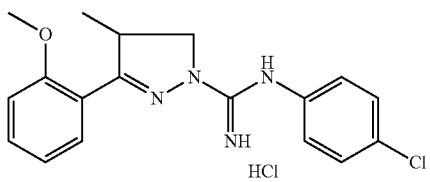 [SMILES: COc1ccccc1C1=NN(C(=N)Nc2ccc(Cl)cc2)CC1C ; Cl]

Prepared by the methods described in Example 92 using 4-chloroaniline as starting material.
Yield: 0.25 g (43%).
¹H NMR ((CD₃)₂SO, 400 MHz) δ: 1.14 (d, 3H), 3.85 (m, 1H), 3.88 (s, 3H), 4.15 (m, 1H), 4.36 (t, 1H), 7.05 (t, 1H), 7.18 (d, 1H), 7.38 (d, 2H), 7.48-7.56 (m, 3H), 7.87 (dd, 1H), 8.12 (s, 2H), 10.15 (s, 1H).

Example 103

N-(4-Chlorophenyl)-3-(2-hydroxyphenyl)-4-methyl-4,5-dihydro-1H-pyrazole-1-carboximidamide

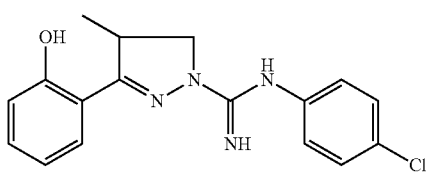 [SMILES: CC1CN(C(=N)Nc2ccc(Cl)cc2)N=C1c1ccccc1O]

Prepared by the method described in Example 40.
Yield: 155 mg (77%).
¹H NMR ((CD₃)₂SO, 400 MHz) δ: 1.19 (d, 3H), 3.65 (dd, 1H), 3.79-3.88 (m, 1H), 3.90 (t, 1H), 6.02 (s, 2H), 6.84 (d, 2H), 6.92 (t, 1H), 6.94 (d, 1H), 7.25 (d, 2H), 7.27 (dt, 1H), 7.54 (dd, 1H), 9.83 (s, 1H).

Example 104

3-(2-(Benzyloxy)phenyl)-N-(4-methoxyphenyl)-4-methyl-4,5-dihydro-1H-pyrazole-1-carboximidamide

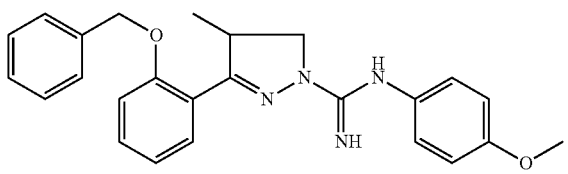 [SMILES: COc1ccc(NC(=N)N2CC(C)C(c3ccccc3OCc3ccccc3)=N2)cc1]

1-(2-(Benzyloxy)phenyl)propan-1-one

Benzyl bromide (68.4 g, 400 mmol) is added to a solution of 1-(2-hydroxyphenyl)propan-1-one (60.0 g, 400 mmol) and K₂CO₃ (111.0 g, 800 mmol) in DMF (400 mL). The reaction mixture is stirred at room temperature for 20 h and is then partitioned in Et2O (1 L) and water (1 L). The organic phase is washed by water (2×300 mL), dried (Na₂SO₄), and concentrated at reduced pressure to give the title compound as a yellow oil (94.0 g, 98%).
¹H NMR (CDCl₃, 400 MHz) δ: 1.13 (t, 3H), 3.00 (q, 2H), 5.17 (s, 2H), 7.00-7.05 (m, 2H), 7.33-7.46 (m, 6H), 7.70 (dd, 1H).

1-(2-(Benzyloxy)phenyl)-3-(dimethyl amino)-2-methylpropan-1-one

Prepared by the method described in Example 1 using 1-(2-(benzyloxy)phenyl)propan-1-one as starting material.
Yield: 39.0 g (66%).
¹H NMR (CDCl₃, 400 MHz) δ: 1.09 (d, 3H), 2.08 (s, 6H), 2.31 (dd, 1H), 2.63 (dd, 1H), 3.69 (m, 1H), 5.15 (s, 2H), 7.00-7.05 (m, 2H), 7.33-7.46 (m, 6H), 7.59 (dd, 1H).

3-(2-(Benzyloxy)phenyl)-N-(4-methoxyphenyl)-4-methyl-4,5-dihydro-1H-pyrazole-1-carboximidamide Prepared by the methods described in Example 92 using 4-methoxyaniline (to give hydrazinyl((4-methoxyphenyl)amino)methaniminium iodide) and 1-(2-(benzyloxy)phenyl)-3-(dimethylamino)-2-methylpropan-1-one as starting materials.
Yield: 0.51 g (45%).
¹H NMR (CDCl₃, 400 MHz) δ: 1.17 (d, 3H), 3.72 (m, 1H), 3.80 (s, 3H), 3.93 (m, 1H), 4.17 (t, 1H), 4.90 (broad s, 2H), 5.13 (s, 2H), 6.87 (d, 2H), 6.93-7.04 (m, 4H), 7.34-7.45 (m, 6H), 7.67 (dd, 1H).

Example 105

3-(2-Hydroxyphenyl)-N-(4-methoxyphenyl)-4-methyl-4,5-dihydro-1H-pyrazole-1-carboximidamide

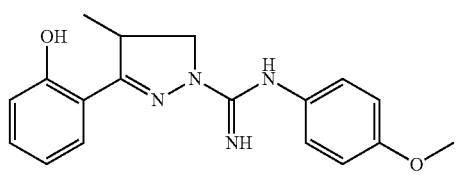 [SMILES: COc1ccc(NC(=N)N2CC(C)C(c3ccccc3O)=N2)cc1]

Hydrogenation of 3-(2-(benzyloxy)phenyl)-N-(4-methoxyphenyl)-4-methyl-4,5-dihydro-1H-pyrazole-1-carboximidamide (480 mg, 1.16 mmol) in MeOH (25 mL) was performed at atm. H₂ with Pd/C (50 mg, 10%) as catalyst for 1 h (26 mL H₂ consumed). The reaction mixture was filtered and the filtrate was concentrated at reduced pressure to give the title compound (0.37 g, 98%).
¹H NMR (CDCl₃, 400 MHz) δ: 1.38 (d, 3H), 3.73-3.85 (m, 1H), 3.80 (s, 3H), 3.95 (dd, 1H), 4.08 (t, 1H), 6.89 (d, 2H), 6.93-6.98 (m, 3H), 7.03 (d, 1H), 7.31 (dt, 1H), 7.35 (dd, 1H).

The following compounds (Examples 106-117) were prepared by the methods described in Example 92 using 1-(3-chloro-2-methoxyphenyl)-3-(dimethylamino)-2-methylpropan-1-one and the corresponding amine or aniline derivatives as starting materials. Demethylations to give phenol derivatives were performed using the method described in Example 40, optionally followed by HCl-salt precipitation.

Example 106

3-(3-Chloro-2-methoxyphenyl)-N-(2,2,3,3,4,4,4-heptafluorobutyl)-4-methyl-4,5-dihydro-1H-pyrazole-1-carboximidamide Exemplified by its Hydrochloride Salt

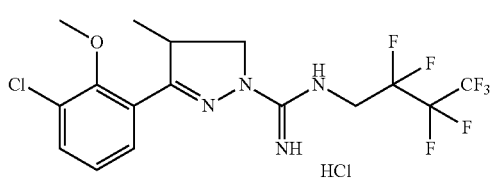 [SMILES: COc1c(Cl)cccc1C1=NN(C(=N)NCC(F)(F)C(F)(F)C(F)(F)F)CC1C ; Cl]

Yield: 0.27 g (38%).
$^1$H NMR (CD$_3$OD, 400 MHz) δ: 1.23 (d, 3H), 3.76 (dd, 1H), 3.87 (s, 3H), 4.15-4.38 (m, 4H), 7.24 (t, 1H), 7.61 (dd, 1H), 7.72 (dd, 1H).

Example 107

3-(3-Chloro-2-hydroxyphenyl)-N-(2,2,3,3,4,4,4-heptafluorobutyl)-4-methyl-4,5-dihydro-1H-pyrazole-1-carboximidamide Exemplified by its Hydrochloride Salt

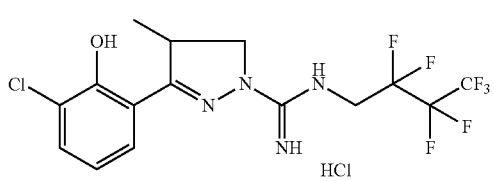 [SMILES: CC1CN(C(=N)NCC(F)(F)C(F)(F)C(F)(F)F)N=C1c1cccc(Cl)c1O ; Cl]

Yield: 0.12 g (51%).
$^1$H NMR (CD$_3$OD, 400 MHz) δ: 1.35 (d, 3H), 3.83 (dd, 1H), 4.17-4.35 (m, 4H), 6.99 (t, 1H), 7.52 (d, 1H), 7.63 (d, 1H).

Example 108

3-(3-Chloro-2-methoxyphenyl)-N-(4-fluorophenyl)-4-methyl-4,5-dihydro-1H-pyrazole-1-carboximidamide

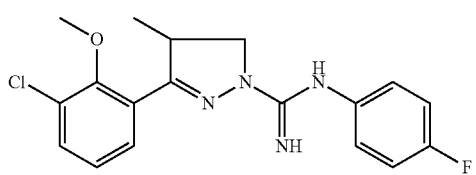 [SMILES: COc1c(Cl)cccc1C1=NN(C(=N)Nc2ccc(F)cc2)CC1C]

Yield: 0.33 g (42%).
$^1$H NMR (CDCl$_3$, 400 MHz) δ: 1.21 (d, 3H), 3.77 (dd, 1H), 3.86 (s, 3H), 3.88 (m, 1H), 4.25 (t, 1H), 4.90 (s, 2H), 6.92-7.04 (m, 4H), 7.10 (t, 1H), 7.44 (dd, 1H), 7.54 (dd, 1H).

Example 109

3-(3-Chloro-2-hydroxyphenyl)-N-(4-fluorophenyl)-4-methyl-4,5-dihydro-1H-pyrazole-1-carboximidamide

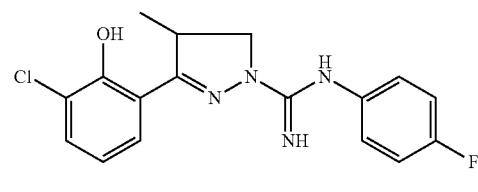 [SMILES: CC1CN(C(=N)Nc2ccc(F)cc2)N=C1c1cccc(Cl)c1O]

Yield: 0.14 g (49%).
$^1$H NMR (CDCl$_3$, 400 MHz) δ: 1.39 (d, 3H), 3.77 (m, 1H), 3.92 (dd, 1H), 4.07 (t, 1H), 4.66 (s, 2H), 6.89-6.95 (m, 3H), 7.02 (t, 2H), 7.27 (dd, 1H), 7.40 (dd, 1H), 10.64 (s, 1H).

Example 110

3-(3-Chloro-2-methoxyphenyl)-N-(4-chlorophenyl)-4-methyl-4,5-dihydro-1H-pyrazole-1-carboximidamide Exemplified by its Hydrochloride Salt

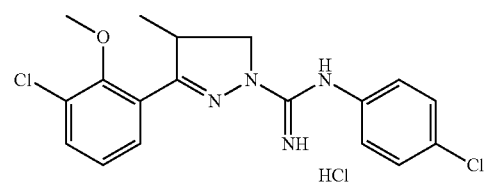 [SMILES: COc1c(Cl)cccc1C1=NN(C(=N)Nc2ccc(Cl)cc2)CC1C ; Cl]

Yield: 197 mg (40%).
$^1$H NMR (CD$_3$OD, 400 MHz) δ: 1.26 (d, 3H), 3.84 (dd, 1H), 3.89 (s, 3H), 4.23 (m, 1H), 4.41 (t, 1H), 7.24 (t, 1H), 7.39 (d, 2H), 7.52 (d, 2H), 7.61 (dd, 1H), 7.75 (dd, 1H).

Example 111

3-(3-Chloro-2-hydroxyphenyl)-N-(4-chlorophenyl)-4-methyl-4,5-dihydro-1H-pyrazole-1-carboximidamide

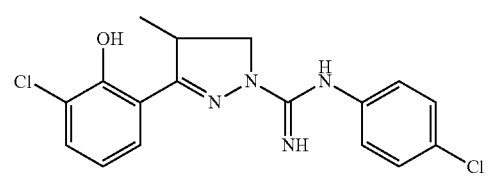 [SMILES: CC1CN(C(=N)Nc2ccc(Cl)cc2)N=C1c1cccc(Cl)c1O]

Yield: 0.12 g (74%).
$^1$H NMR (CDCl$_3$, 400 MHz) δ: 1.39 (d, 3H), 3.77 (m, 1H), 3.91 (dd, 1H), 4.06 (t, 1H), 4.67 (s, 2H), 6.89-6.94 (m, 3H), 7.26-7.30 (m, 3H), 7.40 (dd, 1H), 10.60 (s, 1H).

Example 112

3-(3-Chloro-2-methoxyphenyl)-4-methyl-N-(4-(trifluoromethyl)phenyl)-4,5-dihydro-1H-pyrazole-1-carboximidamide

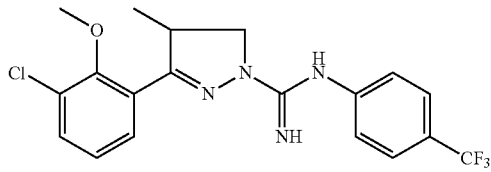 [SMILES: COc1c(Cl)cccc1C1=NN(C(=N)Nc2ccc(C(F)(F)F)cc2)CC1C]

Yield: 0.27 g (27%).

$^1$H NMR (CDCl$_3$, 400 MHz) δ: 1.22 (d, 3H), 3.78 (dd, 1H), 3.86 (s, 3H), 3.90 (m, 1H), 4.27 (t, 1H), 4.96 (s, 2H), 7.09 (d, 2H), 7.11 (t, 1H), 7.45 (dd, 1H), 7.54 (dd, 1H), 7.56 (d, 2H).

Example 113

3-(3-Chloro-2-hydroxyphenyl)-4-methyl-N-(4-(trifluoromethyl)phenyl)-4,5-dihydro-1H-pyrazole-1-carboximidamide

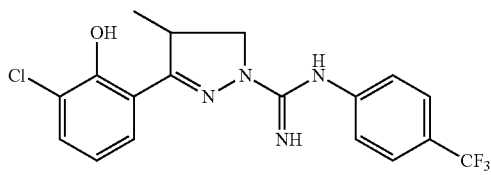 [SMILES: CC1CN(C(=N)Nc2ccc(C(F)(F)F)cc2)N=C1c1cccc(Cl)c1O]

Yield: 0.17 g (72%).

$^1$H NMR (CDCl$_3$, 400 MHz) δ: 1.40 (d, 3H), 3.79 (m, 1H), 3.94 (dd, 1H), 4.09 (t, 1H), 4.75 (broad s, 2H), 6.93 (t, 1H), 7.08 (d, 2H), 7.29 (dd, 1H), 7.42 (dd, 1H), 7.58 (d, 2H), 10.55 (broad s, 1H).

Example 114

3-(3-Chloro-2-methoxyphenyl)-N-(2-chlorophenyl)-4-methyl-4,5-dihydro-1H-pyrazole-1-carboximidamide Exemplified by its Hydrochloride Salt

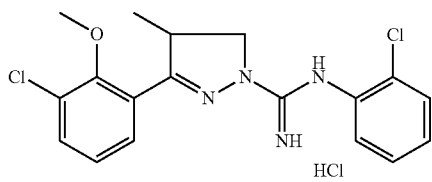 [SMILES: COc1c(Cl)cccc1C1=NN(C(=N)Nc2ccccc2Cl)CC1C ; Cl]

Yield: 0.18 g (22%).

$^1$H NMR (CD$_3$OD, 400 MHz) δ: 1.27 (d, 3H), 3.84 (dd, 1H), 3.90 (s, 3H), 4.24 (m, 1H), 4.42 (t, 1H), 7.24 (t, 1H), 7.45-7.54 (m, 3H), 7.59-7.66 (m, 2H), 7.76 (dd, 1H).

Example 115

3-(3-Chloro-2-hydroxyphenyl)-N-(2-chlorophenyl)-4-methyl-4,5-dihydro-1H-pyrazole-1-carboximidamide

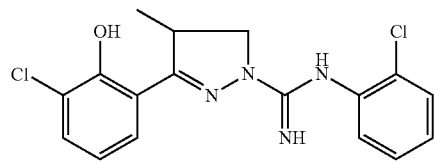 [SMILES: CC1CN(C(=N)Nc2ccccc2Cl)N=C1c1cccc(Cl)c1O]

Yield: 80 mg (67%).

$^1$H NMR (CDCl$_3$, 400 MHz) δ: 1.41 (d, 3H), 3.80 (m, 1H), 4.00 (dd, 1H), 4.16 (t, 1H), 4.67 (broad s, 2H), 6.92 (t, 1H), 7.00 (dt, 1H), 7.05 (dd, 1H), 7.23 (dt, 1H), 7.28 (dd, 1H), 7.39-7.43 (m, 2H), 10.58 (broad s, 1H).

Example 116

3-(3-Chloro-2-methoxyphenyl)-N-(4-fluorobenzyl)-4-methyl-4,5-dihydro-1H-pyrazole-1-carboximidamide Exemplified by its Hydrochloride Salt

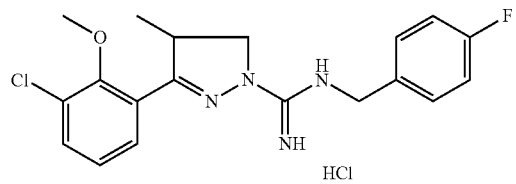 [SMILES: COc1c(Cl)cccc1C1=NN(C(=N)NCc2ccc(F)cc2)CC1C ; Cl]

Yield: 0.40 g (49%).

$^1$H NMR (CD$_3$OD, 400 MHz) δ: 1.22 (d, 3H), 3.75 (dd, 1H), 3.86 (s, 3H), 4.17 (m, 1H), 4.32 (dd, 1H), 4.58 (s, 2H), 7.13 (t, 2H), 7.22 (t, 1H), 7.42 (dd, 2H), 7.59 (dd, 1H), 7.72 (dd, 1H).

Example 117

3-(3-Chloro-2-hydroxyphenyl)-N-(4-fluorobenzyl)-4-methyl-4,5-dihydro-1H-pyrazole-1-carboximidamide

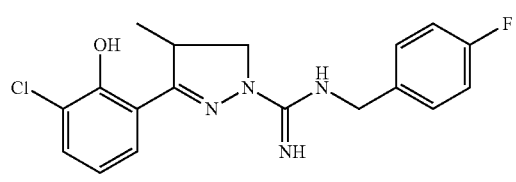 [SMILES: CC1CN(C(=N)NCc2ccc(F)cc2)N=C1c1cccc(Cl)c1O]

Yield: 0.15 g (51%).

$^1$H NMR (CD$_3$OD, 400 MHz) δ: 1.23 (d, 3H), 3.63 (dd, 1H), 4.05 (t, 1H), 4.35 (m, 1H), 4.52 (s, 2H), 6.37 (t, 1H), 7.11 (t, 2H), 7.25 (dd, 1H), 7.34 (dd, 1H), 7.40 (dd, 2H).

Example 118

Ethyl ((3-(3-chloro-2-((ethoxycarbonyl)oxy)phenyl)-4-methyl-4,5-dihydro-1H-pyrazol-1-yl)(imino)methyl)carbamate

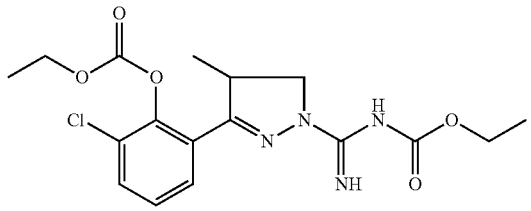 [SMILES: CCOC(=O)NC(=N)N1CC(C)C(c2cccc(Cl)c2OC(=O)OCC)=N1]

A solution of EtOC(O)Cl (250 mg, 2.31 mmol) in $CH_2CL_2$ (5 mL) was added to a solution of 3-(3-chloro-2-hydroxyphenyl)-4-methyl-4,5-dihydro-1H-pyrazole-1-carboximidamide hydrobromide (700 mg, 2.10 mmol) and $NEt_3$ (470 mg, 4.62 mmol) in $CH_2CL_2$ (25 mL). The reaction mixture was stirred at room temperature overnight and was then concentrated at reduced pressure. The residue was purified by silica column chromatography ($CH_2Cl_2$, then $CH_2Cl_2$-MeOH 20:1) to give the title compound (380 mg, 46%).

$^1$H NMR ($CDCl_3$, 400 MHz) δ: 1.24 (d, 3H), 1.33 (t, 3H), 1.36 (t, 3H), 3.72 (m, 1H), 3.93 (dd, 1H), 4.12 (t, 1H), 4.15 (q, 2H), 4.33 (q, 2H), 6.60 (s, 1H), 7.30 (t, 1H), 7.45 (dd, 1H), 7.53 (dd, 1H), 8.70 (s, 1H).

Example 119

Ethyl ((3-(3-chloro-2-hydroxyphenyl)-4-methyl-4,5-dihydro-1H-pyrazol-1-yl)(imino)methyl)carbamate

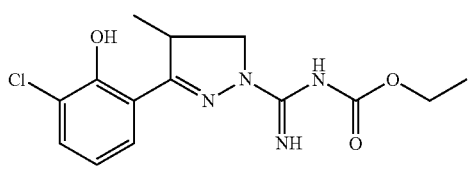 [SMILES: CCOC(=O)NC(=N)N1CC(C)C(c2cccc(Cl)c2O)=N1]

Ethyl((3-(3-chloro-2-((ethoxycarbonyl)oxy)phenyl)-4-methyl-4,5-dihydro-1H-pyrazol-1-yl)(imino)methyl)carbamate (120 mg, 0.30 mmol) was dissolved in MeONa/MeOH (0.03 M, 10 mL, 0.30 mmol) and the reaction mixture was stirred at room temperature overnight. The reaction mixture was neutralized with 2 M HCl/$Et_2O$ and then concentrated at reduced pressure. The residue was purified by silica column chromatography (heptane:EtOAc, 2:1) to give the title compound (85 mg, 87%) as a white solid.

$^1$H NMR ($CDCl_3$, 400 MHz) δ: 1.34 (t, 3H), 1.36 (d, 3H), 3.79 (m, 1H), 4.03-4.11 (m, 2H), 4.18 (m, 2H), 5.96, (broad s, 1H), 6.94 (t, 1H), 7.29 (dd, 1H), 7.45 (dd, 1H), 8.91 (broad s, 1H), 10.30 (s, 1H).

Example 120

5-$HT_{2B}$ receptor binding (performed at Eurofins Panlabs Taiwan, Ltd.) to human receptor protein expressed in CHO-K1 cells was determined in a ligand displacement assay using $^3$H-lysergic acid diethylamide (LSD) as radioligand and ketanserine as a standard reference compound. Data is presented as % displacement of radioligand at indicated compound concentrations, see Table 1 and Table 2.

TABLE 1

| Compound (Ex. No) | 5-$HT_{2B}$ receptor binding (% displacement)) | | | | |
|---|---|---|---|---|---|
| | 0.001 uM | 0.01 uM | 0.1 uM | 1 uM | 10 uM |
| 1 | | | | 76 | 97 |
| 3 | | | | 90 | 99 |
| 4 | | | | 89 | 101 |
| 5 | | | | 95 | 100 |
| 6 | | | | 89 | 99 |
| 7 | | | | 47 | 94 |
| 8 | | | 80 | 95 | |
| 9 | | | 81 | 99 | |
| 10 | | | 75 | 95 | |
| 11 | | | 10 | 53 | |
| 13 | | | 34 | 82 | |
| 14 | | | 40 | 88 | |
| 17 | | 54 | 91 | 100 | 100 |
| 18 | | | | 89 | 101 |
| 19 | | | 34 | 79 | |
| 20 | | | 41 | 89 | |
| 21 | | | 59 | 96 | |
| 22 | | | 89 | 102 | |
| 23 | | | 68 | 97 | |
| 24 | | 39 | 86 | 102 | |
| 25 | | | 54 | 91 | |
| 26 | | | 7 | 55 | |
| 27 | | | 25 | 76 | |
| 28 | | | 63 | 95 | |
| 29 | | | 69 | 97 | |
| 30 | | | 44 | 88 | |
| 31 | | | 21 | 69 | |
| 32 | | | 28 | 79 | |
| 33 | | | 5 | 37 | |
| 34 | | | 23 | 52 | |
| 37 | | -1 | 35 | 72 | 99 |
| 38 | 19 | 76 | 98 | 102 | 104 |
| 40 | 1 | 42 | 92 | 99 | |
| 42 | 49 | 97 | 98 | 99 | |
| 44 | 12 | 30 | 85 | 94 | |
| 45 | | 26 | 54 | 86 | |
| 46 | | 22 | 54 | 89 | |
| 47 | | 15 | 68 | 92 | |
| 48 | | 54 | 85 | 95 | |
| 49 | | 11 | 28 | 78 | |
| 50 | | 42 | 87 | 96 | |
| 51 | | 7 | 31 | 76 | |
| 52 | | 34 | 72 | 95 | |
| 53 | | 40 | 87 | 100 | |
| 54 | | 81 | 95 | 101 | |
| 55 | 16 | 67 | | | |
| 56 | 52 | 95 | | | |
| 57 | 21 | 78 | | | |
| 58 | 2 | 52 | | | |
| 59 | 20 | 74 | | | |
| 60 | 6 | 28 | | | |
| 61 | 13 | 36 | | | |
| 62 | 27 | 72 | | | |
| 63 | 36 | 81 | | | |
| 64 | 23 | 43 | | | |
| 65 | 48 | 89 | | | |
| 66 | | 5 | 12 | 41 | |
| 67 | | 9 | 31 | 72 | |
| 68 | | | 32 | 86 | |
| 69 | | | 70 | 97 | |
| 70 | | 38 | 84 | 98 | |
| 71 | | 11 | 20 | 43 | |
| 72 | -1 | 21 | 69 | | |
| 73 | 49 | 83 | 99 | | |
| 75 | 76 | 97 | | | |
| 76 | 91 | 101 | 103 | | |
| 77 | 2 | 28 | 88 | | |
| 78 | 49 | 85 | 98 | | |

TABLE 1-continued

| Compound (Ex. No) | 5-HT$_{2B}$ receptor binding (% displacement) | | | | |
|---|---|---|---|---|---|
| | 0.001 uM | 0.01 uM | 0.1 uM | 1 uM | 10 uM |
| 79 | 79 | 91 | 94 | | |
| 80 | 13 | 68 | 97 | | |
| 81 | 62 | 96 | 97 | | |
| 82 | 0 | −4 | 51 | | |
| 83 | 3 | 23 | 82 | | |
| 84 | 11 | 63 | 94 | | |
| 85 | 47 | 93 | 101 | | |
| 86 | −14 | 29 | 83 | | |
| 87 | 24 | 84 | 100 | | |
| 88 | 53 | 92 | 97 | | |
| 89 | 88 | 100 | 97 | | |
| 90 | 3 | 1 | −2 | | |
| 91 | −15 | 27 | 74 | | |
| 92 | −3 | 22 | 78 | | |
| 93 | 21 | 80 | 98 | | |
| 94 | −12 | 17 | 77 | | |
| 95 | 12 | 70 | 96 | | |
| 96 | 19 | 43 | 93 | | |
| 97 | 62 | 99 | 105 | | |
| 98 | 5 | 41 | 86 | | |
| 99 | 48 | 89 | 103 | | |
| 100 | 19 | 27 | 78 | | |
| 101 | 55 | 91 | 102 | | |
| 102 | 17 | 44 | 92 | | |
| 103 | 42 | 90 | 99 | | |
| 104 | −9 | 33 | 77 | | |
| 105 | 46 | 95 | 106 | | |
| 106 | 16 | 57 | 93 | | |
| 107 | 51 | 91 | 100 | | |
| 108 | 29 | 83 | 101 | | |
| 109 | 72 | 99 | 104 | | |
| 110 | 41 | 83 | 97 | | |
| 111 | 80 | 99 | 101 | | |
| 112 | 1 | 77 | 97 | | |
| 113 | 59 | 95 | 99 | | |
| 118 | | | 0 | 54 | 91 |
| 119 | | | 50 | 89 | 99 |

TABLE 2

Comparative compounds.

| Compound (Ex. No) | 5-HT$_{2B}$ receptor binding (% displacement) | | | |
|---|---|---|---|---|
| | 0.01 uM | 0.1 uM | 1 uM | 10 uM |
| 2 | | | 38 | 88 |
| 12 | | 18 | 76 | |
| 15 | | | 13 | 56 |
| 16 | | | 6 | 42 |

The results show a clear positive effect of ortho-substituents in the aromatic ring on 5-HT$_{2B}$ receptor binding.

Example 121

5-HT$_{2B}$ receptor antagonism (performed at Eurofins Panlabs Taiwan, Ltd.) was determined in CHO-K1 cells expressing human receptor protein as inhibition of 5-HT (5 nM) stimulated IP-1 accumulation measured by HTRF quantitation. SB 206553 was used as a standard reference compound. The antagonistic response is expressed as % inhibition of the 5-HT induced effect.

The results demonstrated potent antagonistic effects in accordance with receptor binding potencies, see Table 3.

TABLE 3

| Ex. No | 5-HT$_{2B}$ antagonism (%) | | | | | |
|---|---|---|---|---|---|---|
| | 0.0001 uM | 0.001 uM | 0.01 uM | 0.1 uM | 1 uM | 10 uM |
| 1 | | | 2 | 0 | 72 | 107 |
| 3 | | | 14 | 38 | 96 | 103 |
| 9 | | 6 | 20 | 76 | 103 | 116 |
| 17 | | 31 | 70 | 96 | 100 | 103 |
| 21 | | −6 | 10 | 41 | 104 | 113 |
| 22 | | 14 | 28 | 88 | 108 | 110 |
| 38 | 23 | 27 | 75 | 100 | 102 | |
| 73 | 29 | 87 | 97 | 97 | 98 | |
| 76 | 79 | 95 | 99 | 99 | 95 | |

Example 122

5-HT$_{2B}$ receptor agonism (performed at Eurofins Panlabs Taiwan, Ltd.) was determined in the same model as described above in Ex. 117. without prior stimulation with 5-HT. The agonistic response is expressed as % of the IP-1 accumulation induced by 5-HT (1 uM) stimulation.

The results demonstrated the absence of agonistic effects of all the tested compounds at all concentrations tested, see Table 4.

TABLE 4

| Ex. No | 5-HT$_{2B}$ agonism (%) | | | | | |
|---|---|---|---|---|---|---|
| | 0.0001 uM | 0.001 uM | 0.01 uM | 0.1 uM | 1 uM | 10 uM |
| 1 | | | −1 | −8 | −5 | −1 |
| 3 | | | 1 | −2 | −2 | −7 |
| 9 | | −3 | −8 | −8 | −13 | −5 |
| 17 | | 1 | 3 | 7 | 2 | −2 |
| 21 | | 3 | −5 | −9 | −6 | −13 |
| 22 | | −5 | −10 | −1 | −3 | −2 |
| 38 | −2 | −1 | −2 | 0 | −2 | |
| 73 | 3 | 4 | 3 | 3 | | |
| 76 | 0 | 1 | 3 | −1 | | |

Example 123

Reduction of TNF-α plasma levels in the LPS-induced acute inflammation in mice was used to determine the in vivo anti-inflammatory properties of the compounds.

Method

Mice (BALB/c, female, approx. 20 g, 8 mice/group) were treated with the test compound perorally (10 or 30 mg/kg in water) 30 min prior to LPS treatment (10 ug in saline, intraperitoneally, serotype 055:B5). Alternatively, the test compound was administered subcutaneously in the neck (10 or 30 mg/kg in 10% PEG400 in saline) 15 min prior to LPS treatment. Blood samples were collected 90 min after LPS treatment and plasma TNF-α concentrations were determined in duplicates by ELISA.

Test Compounds

Compound 1: 3-(2-Hydroxyphenyl)-4,5-dihydro-1H-pyrazole-1-carboximidamide Hydrochloride (Ex 3)

Compound 2: 3-(2-Hydroxyphenyl)-4-methyl-4,5-dihydro-1H-pyrazole-1-carboximidamide Hydrochloride (Ex 17)

RS127445: as reference compound (5-HT$_{2B}$ selective antagonist)

Results

Anti-inflammatory effects determined as reduction of TNF-α plasma levels were demonstrated for both Compound 1 and Compound 2. Compound 1, administered per orally (p.o.), dose-dependently reduced TNF-α plasma levels. Compound 2 also reduced TNF-α levels with p.o. administration and demonstrated dose-dependent effects with subcutaneous (s.c.) administration. Compared with the reference compound RS127545, Compound 2 showed equal or higher anti-inflammatory effects. Results are shown in Table 5. SEM is to be understood as standard error mean.

TABLE 5

| Experiment No and admin. | Treatment | TNF-α (pg/mL) | SEM (pg/mL) |
|---|---|---|---|
| 1 | vehicle (control) | 9639 | 2211 |
| p.o. | Compound 1, 10 mg/kg | 5767 | 2658 |
| (water) | Compound 1, 30 mg/kg | 3992 | 1437 |
| 2 | vehicle (control) | 8866 | 2868 |
| p.o. | Compound 2, 10 mg/kg | 4139 | 907 |
| (water) | Compound 2, 30 mg/kg | 4062 | 2319 |
| 3 | vehicle (control) | 5749 | 1670 |
| s.c. | Compound 2, 10 mg/kg | 2708 | 1199 |
| (PEG400/saline) | Compound 2, 30 mg/kg | 1397 | 649 |
|  | RS127445, 10 mg/kg | 3215 | 1397 |

Example 124

Effects on Collagen Production in Normal Human Lung Fibroblasts.

Normal human lung fibroblasts (NHLF, Lonza) were cultured in FGM-2 full medium (+FBS) according to manufacturer's instructions. When confluent, cells were seeded onto 24-well tissue culture plates at 100.000 cells/well (4 wells per condition), until reaching confluence. Once cells were confluent they were serum starved overnight in serum free FGM-2 medium. After 16 hours the serum free medium was removed and cells were treated with (R)-3-(2-hydroxyphenyl)-4-methyl-4,5-dihydro-1H-pyrazole-1-carboximidamide (Example 36, Compound 3) at 1 and 10 µM (vehicle ddH$_2$O). The cells were then stimulated with 5 ng/mL human recombinant TGF-β1 alone or in combination with 1 µM or 10 µM 5-HT. All stimuli were prepared in serum free FGM-2 media (1 mL volume/well). Unstimulated cells received serum free FGM-2 medium alone. After 48 hours the supernatants were collected and stored at −80° C. Collagen production was analyzed in supernatants using procollagen type I C-peptide (PIP) ELISA (Takara Bio # MK1010). Cell viability was tested using a LDH assay (Abcam # Ab102526).

Results

Normal human lung fibroblasts increased the production of collagens upon stimulation with 5 ng/mL TGF-β1 and 5-HT. Treatment with Compound 3 significantly reduced the production of collagens. This result suggests an anti-fibrotic role for Compound 3. Results are presented in FIG. 1.

Example 125

Anti-Fibrotic Effects of in the Bleomycin-Induced Pulmonary Fibrosis Model in Mice.

Pulmonary fibrosis was induced in female C57BL/6 mice by intratracheal instillation of bleomycin in saline (50 uL, 0.5 mg/mL). Treatment was initiated at the day of intratracheal instillation and continued to day 28. The mice (8 animals/group) were orally treated twice daily with 25 or 75 mg/kg (R)-3-(2-Hydroxyphenyl)-4-methyl-4,5-dihydro-1H-pyrazole-1-carboximidamide (Example 36, Compound 3) dissolved in ddH$_2$O. Nintedanib at 30 mg/kg in ddH$_2$O, p.o., twice daily, was used as a positive control. Vehicle-treated bleomycin-challenged mice and vehicle-treated non-fibrotic mice served as controls. The animals were sacrificed after 28 days and the fibrotic area of the lung was determined by histological evaluation of Sirius Red-stained sections according to standard protocol. The collagen content of lung tissue was measured using the hydroxyproline collagen assay and the number of myofibroblasts was quantified by staining for α-smooth muscle actin (α-SMA) in paraffin embedded sections.

Results

Figure 2:
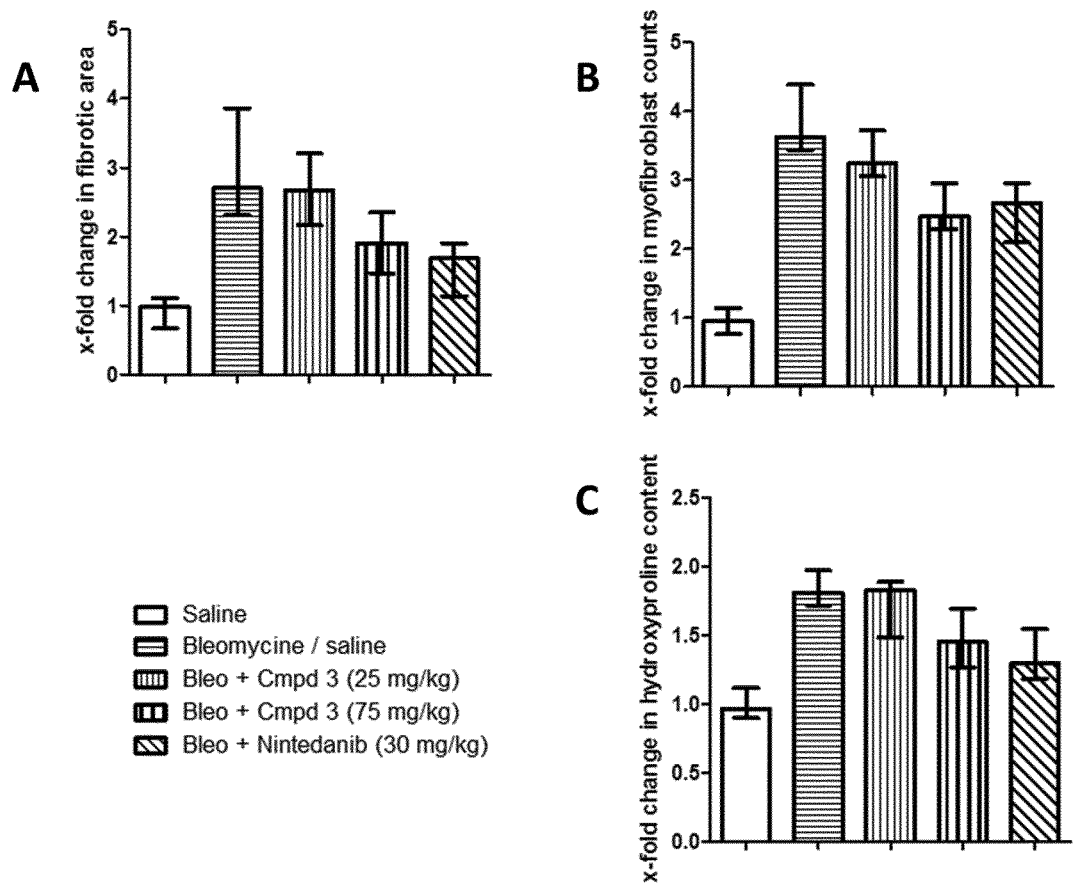
FIG. 2 provides a histogram with data showing anti-fibrotic effects by a compound of the invention in the bleomycin-induced pulmonary fibrosis model in mice. A compound of the invention in doses of 75 mg/kg bid and Nintedanib at doses of 30 mg/kg bid ameliorated bleomycin-induced pulmonary fibrosis and reduced the fibrotic area (A), inhibited myofibroblast differentiation (B), and reduced the hydroxyproline content (C).

Compound 3 in doses of 75 mg/kg bid and Nintedanib at doses of 30 mg/kg bid ameliorated bleomycin-induced pulmonary fibrosis and reduced the fibrotic area (A), inhibited myofibroblast differentiation (B), and reduced the hydroxyproline content (C). No statistically significant changes in any of the outcomes were observed with Compound 3 in doses of 25 mg/kg bid.

n=8 mice for all groups. * indicates significant changes with p<0.05 as compared to vehicle-treated, bleomycin-challenged mice. Results are presented in FIG. 2.

The invention claimed is:

1. A compound of the general formula I:

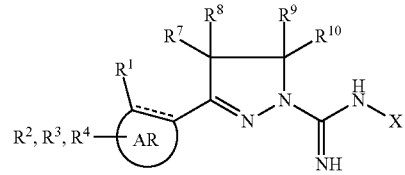

wherein

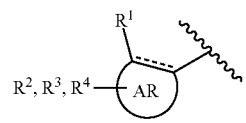

represents

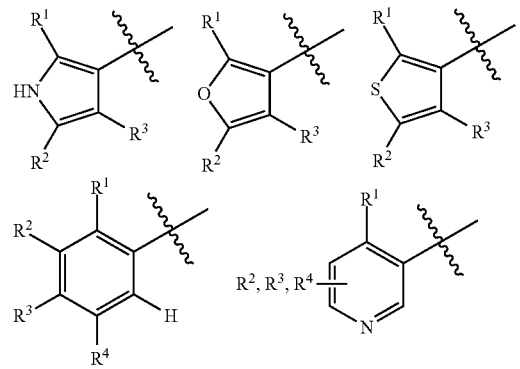

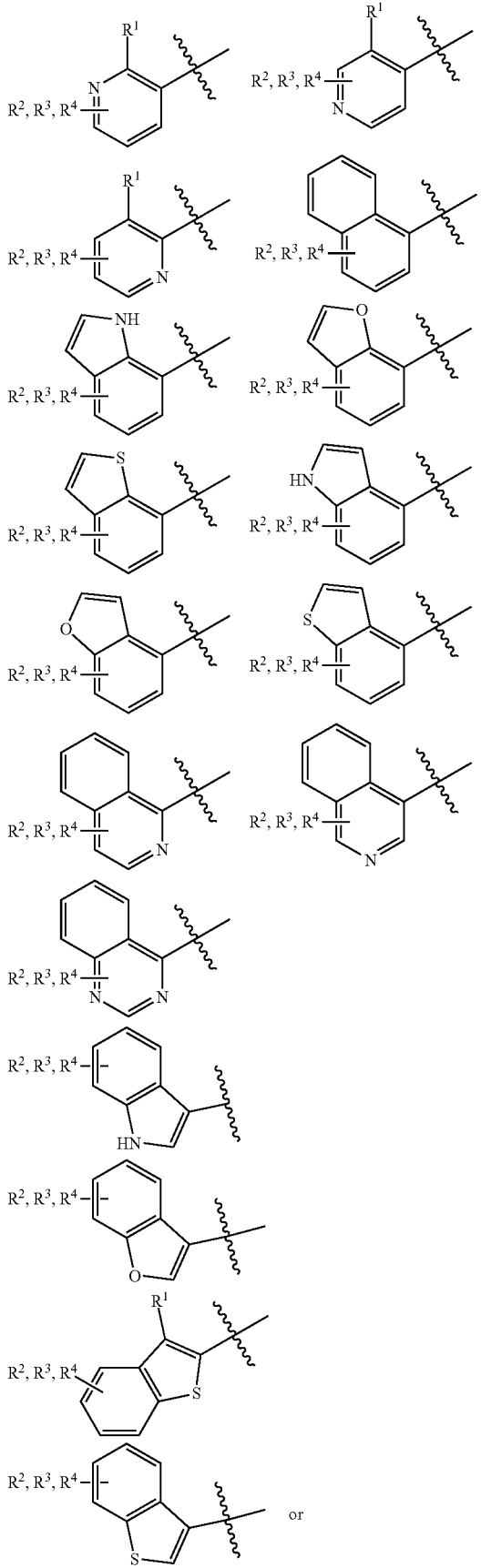

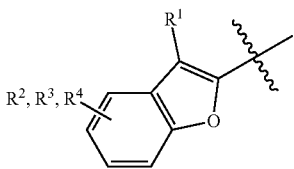

wherein

R[1] is selected from methyl, ethyl, iso-propyl, cyclopropyl, $CF_3$, hydroxy, methoxy, ethoxy, iso-propoxy, benzyloxy, $OC(O)OCH_2CH_3$, $OCF_3$, $SCH_3$, $S(O)_2CH_3$, $OC(O)OR^5$, $OC(O)R^5$, $NHCH_3$, $N(CH_3)_2$, $NHC(O)H$, $NHC(O)CH_3$, $NHC(O)NH_2$, $NHC(O)NHCH_3$, $NHC(O)N(CH_3)_2$, $C(O)CH_3$, $C(O)N(CH_3)_2$, Cl, Br, I, CN, and phenyl;

R[2] is selected from hydrogen, methyl, ethyl, iso-propyl, cyclopropyl, $CF_3$, hydroxy, methoxy, ethoxy, iso-propoxy, $OCF_3$, $SCH_3$, $S(O)_2CH_3$, $NH_2$, $NHCH_3$, $N(CH_3)_2$, $NHC(O)H$, $NHC(O)CH_3$, $NHC(O)NH_2$, $NHC(O)NHCH_3$, $NHC(O)N(CH_3)_2$, $C(O)CH_3$, $C(O)N(CH_3)_2$, F, Cl, Br, I, CN, and phenyl;

R[3] is selected from hydrogen, methyl, ethyl, iso-propyl, cyclopropyl, $CF_3$, ethoxy, iso-propoxy, $OCF_3$, $SCH_3$, $S(O)_2CH_3$, $NH_2$, $NHCH_3$, $N(CH_3)_2$, $NHC(O)H$, $NHC(O)CH_3$, $NHC(O)NH_2$, $NHC(O)NHCH_3$, $NHC(O)N(CH_3)_2$, $C(O)CH_3$, $C(O)N(CH_3)_2$, F, Cl, Br, I, CN, and phenyl;

R[4] is selected from hydrogen, methyl, ethyl, iso-propyl, cyclopropyl, $CF_3$, hydroxy, methoxy, ethoxy, iso-propoxy, $OCF_3$, $SCH_3$, $S(O)_2CH_3$, $NH_2$, $NHCH_3$, $N(CH_3)_2$, $NHC(O)H$, $NHC(O)CH_3$, $NHC(O)NH_2$, $NHC(O)NHCH_3$, $NHC(O)N(CH_3)_2$, $C(O)CH_3$, $C(O)N(CH_3)_2$, F, Br, I, CN, and phenyl;

R[5] represents $C_1$-$C_{15}$ alkyl or phenyl;

R[7], R[8], R[9], and R[19] are independently selected from hydrogen and methyl; and X is selected from hydrogen, $C_1$-$C_{12}$ alkyl, $C_3$-$C_6$ cycloalkyl, $C_1$-$C_4$ fluoroalkyl, phenyl, 2-phenylethyl, benzyl, $C(O)OCH_2CH_3$, and hydroxy; wherein said phenyl, 2-phenylethyl, and benzyl are optionally mono- or di-substituted by substituents independently selected from methyl, ethyl, methoxy, F, and Cl; and pharmaceutically acceptable salts, prodrugs, tautomers, and stereoisomers thereof, with the proviso that when R[7] is methyl and having the configuration as shown in formula Ib, Ib

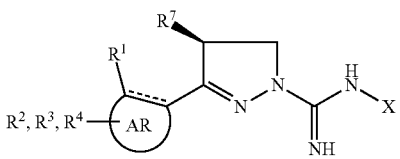

R[3] is not hydrogen; and when X, R[3], R[7] and R[8] are simultaneously hydrogen, R[1] is not methoxy.

2. A compound according to claim 1, wherein

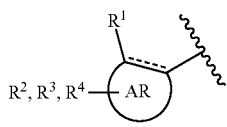

represents

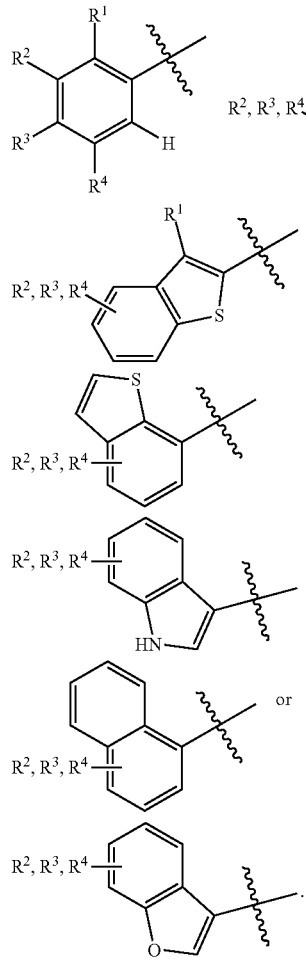

3. The compound according to claim 1, wherein $R^1$ is selected from methyl, ethyl, iso-propyl, $CF_3$, hydroxy, methoxy, benzyloxy, $OC(O)OCH_2CH_3$, Cl, and Br;

$R^2$ is selected from hydrogen, F, and Cl;

$R^3$ is selected from hydrogen, $CF_3$, and F; and $R^4$ is selected from hydrogen and F.

4. A compound according to claim 1, wherein

X is selected from hydrogen, $C_1$-$C_{12}$ alkyl, $C_3$-$C_6$ cycloalkyl, phenyl, $C_1$-$C_4$ fluoroalkyl, benzyl, 2-phenylethyl, $C(O)OCH_2CH_3$, and hydroxyl, wherein said phenyl, 2-phenylethyl, and benzyl are optionally mono- or di-substituted with substituents independently selected from methyl, methoxy, F, and Cl.

5. A compound according to claim 1, wherein

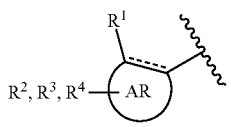

represents

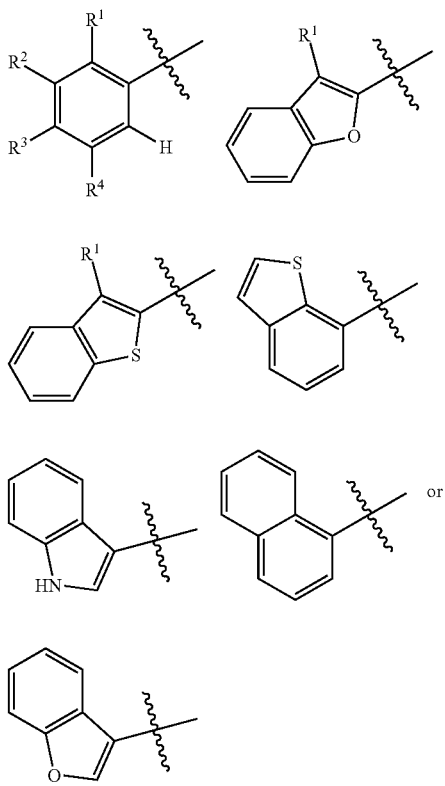

wherein $R^1$ is selected from methyl, isopropyl, $CF_3$, hydroxy, methoxy, benzyloxy, $OC(O)OCH_2CH_3$, Cl, and Br;

$R^2$ is selected from hydrogen, F, and Cl;

$R^3$ is selected from hydrogen, $CF_3$, and F;

$R^4$ is selected from hydrogen and F;

$R^7$, $R^8$, $R^9$, and $R^{10}$ are independently selected from hydrogen and methyl;

X is selected from hydrogen, methyl, butyl, hexyl, dodecyl, cyclohexyl, cyclopropyl, phenyl, 2,2,3,3,4,4,4-heptafluorobut-1-yl, 2,2,2-trifluoroeth-1-yl, 4-fluorophenyl, 2-chlorophenyl, 4-chlorophenyl, 4-methoxyphenyl, benzyl, $CHCH_3C_6H_5$, 4-chlorobenzyl, 4-fluorobenzyl, 2-chlorobenzyl, 2,4-dichlorobenzyl, 3,4-dichlorobenzyl, 4-methoxybenzyl, 3,5-dimethoxybenzyl, 3,4-dimethoxybenzyl, 3-chloro-4-methoxybenzyl, 2-phenylethyl, $C(O)OCH_2CH_3$, and hydroxy;

with the proviso that when $R^7$ is methyl and having the configuration as shown in formula Ib,

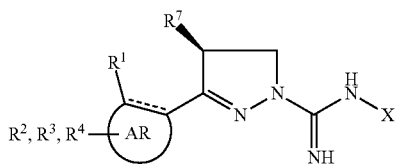

R³ is not hydrogen; and
when X, R³, R⁷ and R⁸ are simultaneously hydrogen, R¹ is not methoxy.

6. A compound according to claim 1, wherein
R⁷ is methyl; and
R⁸, R⁹, and R¹⁰ are hydrogen.

7. A compound according to claim 6, wherein
R⁷ is methyl and having the configuration as shown in formula Ia

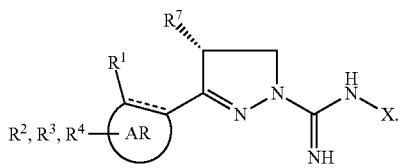

8. A compound according to claim 1, which is:
4-Methyl-3-(naphthalen-1-yl)-4,5-dihydro-1H-pyrazole-1-carboximidamide;
3-(2-Hydroxyphenyl)-4,5-dihydro-1H-pyrazole-1-carboximidamide;
3-(2-Bromophenyl)-4,5-dihydro-1H-pyrazole-1-carboximidamide;
3-(2-Chlorophenyl)-4,5-dihydro-1H-pyrazole-1-carboximidamide;
3-(2-Methylphenyl)-4,5-dihydro-1H-pyrazole-1-carboximidamide;
3-(2-Isopropylphenyl)-4,5-dihydro-1H-pyrazole-1-carboximidamide;
3-(Naphthalen-1-yl)-4,5-dihydro-1H-pyrazole-1-carboximidamide;
3-(Benzo[b]thiophen-7-yl)-4,5-dihydro-1H-pyrazole-1-carboximidamide;
3-(2-(Trifluoromethyl)phenyl)-4,5-dihydro-1H-pyrazole-1-carboximidamide;
3-(Benzofuran-3-yl)-4,5-dihydro-1H-pyrazole-1-carboximidamide;
3-(2-Hydroxyphenyl)-4-methyl-4,5-dihydro-1H-pyrazole-1-carboximidamide;
3-(2-Methoxyphenyl)-4-methyl-4,5-dihydro-1H-pyrazole-1-carboximidamide;
3-(2-Chlorophenyl)-N-methyl-4,5-dihydro-1H-pyrazole-1-carboximidamide;
3-(2-Hydroxyphenyl)-N-methyl-4,5-dihydro-1H-pyrazole-1-carboximidamide;
N-Benzyl-3-(2-chlorophenyl)-4,5-dihydro-1H-pyrazole-1-carboximidamide;
N-Benzyl-3-(2-hydroxyphenyl)-4,5-dihydro-1H-pyrazole-1-carboximidamide;
5-methyl-3-(naphthalen-1-yl)-4,5-dihydro-1H-pyrazole-1-carboximidamide;
3-(2-Chlorophenyl)-5-methyl-4,5-dihydro-1H-pyrazole-1-carboximidamide;
5-Methyl-3-(3-methylbenzofuran-2-yl)-4,5-dihydro-1H-pyrazole-1-carboximidamide;
5-Methyl-3-(3-methylbenzo[b]thiophen-2-yl)-4,5-dihydro-1H-pyrazole-1-carboximidamide;
(R)-3-(2-Hydroxyphenyl)-4-methyl-4,5-dihydro-1H-pyrazole-1-carboximidamide;
3-(2-Methoxyphenyl)-N,4-dimethyl-4,5-dihydro-1H-pyrazole-1-carboximidamide;
3-(2-Hydroxyphenyl)-N,4-dimethyl-4,5-dihydro-1H-pyrazole-1-carboximidamide;
N-Benzyl-3-(2-methoxyphenyl)-4-methyl-4,5-dihydro-1H-pyrazole-1-carboximidamide;
N-Benzyl-3-(2-hydroxyphenyl)-4-methyl-4,5-dihydro-1H-pyrazole-1-carboximidamide;
N-Hydroxy-3-(2-methoxyphenyl)-4-methyl-4,5-dihydro-1H-pyrazole-1-carboximidamide;
N-Hydroxy-3-(2-hydroxyphenyl)-4-methyl-4,5-dihydro-1H-pyrazole-1-carboximidamide;
3-(5-Fluoro-2-methoxyphenyl)-4-methyl-4,5-dihydro-1H-pyrazole-1-carboximidamide
3-(5-Fluoro-2-hydroxyphenyl)-4-methyl-4,5-dihydro-1H-pyrazole-1-carboximidamide;
3-(3-Fluoro-2-methoxyphenyl)-4-methyl-4,5-dihydro-1H-pyrazole-1-carboximidamide;
3-(3-Fluoro-2-hydroxyphenyl)-4-methyl-4,5-dihydro-1H-pyrazole-1-carboximidamide;
3-(4-Fluoro-2-methoxyphenyl)-4-methyl-4,5-dihydro-1H-pyrazole-1-carboximidamide;
3-(4-Fluoro-2-hydroxyphenyl)-4-methyl-4,5-dihydro-1H-pyrazole-1-carboximidamide;
3-(5-Chloro-2-hydroxyphenyl)-4-methyl-4,5-dihydro-1H-pyrazole-1-carboximidamide;
3-(3-Chloro-2-methoxyphenyl)-4-methyl-4,5-dihydro-1H-pyrazole-1-carboximidamide;
3-(3-Chloro-2-hydroxyphenyl)-4-methyl-4,5-dihydro-1H-pyrazole-1-carboximidamide;
N-(4-Chlorobenzyl)-3-(2-hydroxyphenyl)-4-methyl-4,5-dihydro-1H-pyrazole-1-carboximidamide;
N-(2-Chlorobenzyl)-3-(2-hydroxyphenyl)-4-methyl-4,5-dihydro-1H-pyrazole-1-carboximidamide;
N-(2,4-Dichlorobenzyl)-3-(2-hydroxyphenyl)-4-methyl-4,5-dihydro-1H-pyrazole-1-carboximidamide;
N-(3,4-Dichlorobenzyl)-3-(2-hydroxyphenyl)-4-methyl-4,5-dihydro-1H-pyrazole-1-carboximidamide;
3-(2-Hydroxyphenyl)-N-(4-methoxybenzyl)-4-methyl-4,5-dihydro-1H-pyrazole-1-carboximidamide;
N-(3,4-Dimethoxybenzyl)-3-(2-hydroxyphenyl)-4-methyl-4,5-dihydro-1H-pyrazole-1-carboximidamide;
N-(3,5-Dimethoxybenzyl)-3-(2-hydroxyphenyl)-4-methyl-4,5-dihydro-1H-pyrazole-1-carboximidamide;
N-(3-chloro-4-methoxybenzyl)-3-(2-hydroxyphenyl)-4-methyl-4,5-dihydro-1H-pyrazole-1-carboximidamide;
3-(2-Hydroxyphenyl)-4-methyl-N—((R)-1-phenylethyl)-4,5-dihydro-1H-pyrazole-1-carboximidamide;
3-(2-Hydroxyphenyl)-4-methyl-N—((S)-1-phenylethyl)-4,5-dihydro-1H-pyrazole-1-carboximidamide;
3-(2-hydroxyphenyl)-4-methyl-N-phenethyl-4,5-dihydro-1H-pyrazole-1-carboximidamide;
3-(2-Methoxy-4-(trifluoromethyl)phenyl)-4-methyl-4,5-dihydro-1H-pyrazole-1-carboximidamide;
3-(2-Hydroxy-4-(trifluoromethyl)phenyl)-4-methyl-4,5-dihydro-1H-pyrazole-1-carboximidamide;
3-(1H-Indol-3-yl)-4-methyl-4,5-dihydro-1H-pyrazole-1-carboximidamide;
(S)-3-(3-chloro-2-hydroxyphenyl)-4-methyl-1H-pyrazole-1-carboximidamide;

(R)-3-(3-chloro-2-hydroxyphenyl)-4-methyl-4,5-dihydro-1H-pyrazole-1-carboximidamide;
N-Benzyl-3-(3-chloro-2-methoxyphenyl)-4-methyl-4,5-dihydro-1H-pyrazole-1-carboximidamide;
N-Benzyl-3-(3-chloro-2-hydroxyphenyl)-4-methyl-4,5-dihydro-1H-pyrazole-1-carboximidamide;
(R)—N-Benzyl-3-(3-chloro-2-hydroxyphenyl)-4-methyl-4,5-dihydro-1H-pyrazole-1-carboximidamide;
(S)—N-Benzyl-3-(3-chloro-2-hydroxyphenyl)-4-methyl-4,5-dihydro-1H-pyrazole-1-carboximidamide;
N-butyl-3-(3-chloro-2-methoxyphenyl)-4-methyl-4,5-dihydro-1H-pyrazole-1-carboximidamide;
N-Butyl-3-(3-chloro-2-hydroxyphenyl)-4-methyl-4,5-dihydro-1H-pyrazole-1-carboximidamide;
3-(3-Chloro-2-methoxyphenyl)-N-hexyl-4-methyl-4,5-dihydro-1H-pyrazole-1-carboximidamide;
3-(3-Chloro-2-hydroxyphenyl)-N-hexyl-4-methyl-4,5-dihydro-1H-pyrazole-1-carboximidamide;
3-(3-Chloro-2-methoxyphenyl)-N-dodecyl-4-methyl-4,5-dihydro-1H-pyrazole-1-carboximidamide;
3-(3-Chloro-2-hydroxyphenyl)-N-dodecyl-4-methyl-4,5-dihydro-1H-pyrazole-1-carboximidamide;
3-(3-Chloro-2-methoxyphenyl)-N-cyclohexyl-4-methyl-4,5-dihydro-1H-pyrazole-1-carboximidamide;
3-(3-Chloro-2-hydroxyphenyl)-N-cyclohexyl-4-methyl-4,5-dihydro-1H-pyrazole-1-carboximidamide;
3-(3-Chloro-2-methoxyphenyl)-N-cyclopropyl-4-methyl-4,5-dihydro-1H-pyrazole-1-carboximidamide;
3-(3-Chloro-2-hydroxyphenyl)-N-cyclopropyl-4-methyl-4,5-dihydro-1H-pyrazole-1-carboximidamide;
3-(3-Chloro-2-methoxyphenyl)-4-methyl-N-phenyl-4,5-dihydro-1H-pyrazole-1-carboximidamide;
3-(3-Chloro-2-hydroxyphenyl)-4-methyl-N-phenyl-4,5-dihydro-1H-pyrazole-1-carboximidamide;
N-(2,2,3,3,4,4,4-Heptafluorobutyl)-3-(2-methoxyphenyl)-4-methyl-4,5-dihydro-1H-pyrazole-1-carboximidamide;
N-(2,2,3,3,4,4,4-Heptafluorobutyl)-3-(2-hydroxyphenyl)-4-methyl-4,5-dihydro-1H-pyrazole-1-carboximidamide;
3-(2-Methoxyphenyl)-4-methyl-N-(2,2,2-trifluoroethyl)-4,5-dihydro-1H-pyrazole-1-carboximidamide;
3-(2-Hydroxyphenyl)-4-methyl-N-(2,2,2-trifluoroethyl)-4,5-dihydro-1H-pyrazole-1-carboximidamide;
3-(2-Methoxyphenyl)-4-methyl-N-phenyl-4,5-dihydro-1H-pyrazole-1-carboximidamide;
3-(2-Hydroxyphenyl)-4-methyl-N-phenyl-4,5-dihydro-1H-pyrazole-1-carboximidamide;
N-(4-Fluorophenyl)-3-(2-methoxyphenyl)-4-methyl-4,5-dihydro-1H-pyrazole-1-carboximidamide;
N-(4-Fluorophenyl)-3-(2-hydroxyphenyl)-4-methyl-4,5-dihydro-1H-pyrazole-1-carboximidamide;
N-(4-Chlorophenyl)-3-(2-methoxyphenyl)-4-methyl-4,5-dihydro-1H-pyrazole-1-carboximidamide;
N-(4-Chlorophenyl)-3-(2-hydroxyphenyl)-4-methyl-4,5-dihydro-1H-pyrazole-1-carboximidamide;
3-(2-(Benzyloxy)phenyl)-N-(4-methoxyphenyl)-4-methyl-4,5-dihydro-1H-pyrazole-1-carboximidamide;
3-(2-Hydroxyphenyl)-N-(4-methoxyphenyl)-4-methyl-4,5-dihydro-1H-pyrazole-1-carboximidamide;
3-(3-Chloro-2-methoxyphenyl)-N-(2,2,3,3,4,4,4-heptafluorobutyl)-4-methyl-4,5-dihydro-1H-pyrazole-1-carboximidamide;
3-(3-Chloro-2-hydroxyphenyl)-N-(2,2,3,3,4,4,4-heptafluorobutyl)-4-methyl-4,5-dihydro-1H-pyrazole-1-carboximidamide;
3-(3-Chloro-2-methoxyphenyl)-N-(4-fluorophenyl)-4-methyl-4,5-dihydro-1H-pyrazole-1-carboximidamide;
3-(3-Chloro-2-hydroxyphenyl)-N-(4-fluorophenyl)-4-methyl-4,5-dihydro-1H-pyrazole-1-carboximidamide;
3-(3-Chloro-2-methoxyphenyl)-N-(4-chlorophenyl)-4-methyl-4,5-dihydro-1H-pyrazole-1-carboximidamide;
3-(3-Chloro-2-hydroxyphenyl)-N-(4-chlorophenyl)-4-methyl-4,5-dihydro-1H-pyrazole-1-carboximidamide;
3-(3-Chloro-2-methoxyphenyl)-N-(2-chlorophenyl)-4-methyl-4,5-dihydro-1H-pyrazole-1-carboximidamide;
3-(3-Chloro-2-hydroxyphenyl)-N-(2-chlorophenyl)-4-methyl-4,5-dihydro-1H-pyrazole-1-carboximidamide;
3-(3-Chloro-2-methoxyphenyl)-N-(4-fluorobenzyl)-4-methyl-4,5-dihydro-1H-pyrazole-1-carboximidamide;
3-(3-Chloro-2-hydroxyphenyl)-N-(4-fluorobenzyl)-4-methyl-4,5-dihydro-1H-pyrazole-1-carboximidamide;
Ethyl((3-(3-chloro-2-((ethoxycarbonyl)oxy)phenyl)-4-methyl-4,5-dihydro-1H-pyrazol-1-yl)(imino)methyl) carbamate; or
Ethyl ((3-(3-chloro-2-hydroxyphenyl)-4-methyl-4,5-dihydro-1H-pyrazol-1-yl)(imino)methyl)carbamate.

9. A method of treating fibrosis, comprising administering a therapeutically effective amount of a compound according to claim 1 to a patient in need thereof.

10. A method of treating fibrosis, wherein the fibrosis is selected from systemic sclerosis, skin fibrosis, liver fibrosis, heart fibrosis, kidney fibrosis, intestinal fibrosis, lung fibrosis, idiopathic pulmonary fibrosis (IPF), fibrosis associated with pulmonary arterial hypertension (PAH), and fibrosis associated with transplantation, surgery, stenosis, or keloid scarring,
the method comprising administering a therapeutically effective amount of a compound according to claim 1 to a patient in need thereof.

11. A pharmaceutical composition comprising a compound according to claim 1, admixed with one or more pharmaceutically acceptable excipients or carriers.

12. The composition according to claim 11, wherein the excipients are selected from the group comprising filling agents, lubricants, flavors, colorings, sweetenings, buffers, acidifying agents, diluents, and preservatives.

13. The composition according to claim 11, wherein the composition is formulated to be administered orally, by oral inhalation, intramuscularly, intravenously, intraperitoneally, or subcutaneously, via implants, rectally, intranasally, or transdermally.

14. The composition according to claim 11 comprising a further therapeutic agent.

* * * * *

UNITED STATES PATENT AND TRADEMARK OFFICE
CERTIFICATE OF CORRECTION

PATENT NO. : 10,544,103 B2
APPLICATION NO. : 15/737125
DATED : January 28, 2020
INVENTOR(S) : Lars Pettersson Page 1 of 1

It is certified that error appears in the above-identified patent and that said Letters Patent is hereby corrected as shown below:

In the Claims

Column 98, Line 41 reads $R^7$, $R^8$, $R^9$, and $R^{19}$, whereas it should read --$R^7$, $R^8$, $R^9$ and $R^{10}$--.

Signed and Sealed this
Twenty-fourth Day of March, 2020

Andrei Iancu
*Director of the United States Patent and Trademark Office*